United States Patent
Bettoun et al.

(10) Patent No.: US 12,091,437 B2
(45) Date of Patent: *Sep. 17, 2024

(54) MOLECULES FOR ORGANELLE-SPECIFIC PROTEIN DELIVERY

(71) Applicant: Larimar Therapeutics, Inc., Bala Cynwyd, PA (US)

(72) Inventors: Joan David Bettoun, Elkins Park, PA (US); Rebecca Wissner, Wayne, PA (US)

(73) Assignee: Larimar Therapeutics, Inc., Bala Cynwyd, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/390,884

(22) Filed: Dec. 20, 2023

(65) Prior Publication Data

US 2024/0228557 A1 Jul. 11, 2024

Related U.S. Application Data

(63) Continuation of application No. 17/214,757, filed on Mar. 26, 2021, now Pat. No. 11,891,420.

(60) Provisional application No. 63/000,138, filed on Mar. 26, 2020.

(51) Int. Cl.
| | |
|---|---|
| *C07K 14/47* | (2006.01) |
| *A61K 38/00* | (2006.01) |
| *A61K 47/64* | (2017.01) |
| *C07K 14/005* | (2006.01) |
| *C12N 9/10* | (2006.01) |

(52) U.S. Cl.
CPC .............. *C07K 14/47* (2013.01); *A61K 47/64* (2017.08); *C07K 14/005* (2013.01); *C12N 9/104* (2013.01); *C12Y 203/02* (2013.01); *A61K 38/00* (2013.01); *C07K 2319/02* (2013.01); *C07K 2319/07* (2013.01); *C07K 2319/50* (2013.01); *C12N 2740/16322* (2013.01)

(58) Field of Classification Search
None
See application file for complete search history.

(56) References Cited

U.S. PATENT DOCUMENTS

| | | |
|---|---|---|
| 11,459,363 B2 | 10/2022 | Payne |
| 2012/0196328 A1 | 8/2012 | Liu et al. |
| 2021/0355177 A1 | 11/2021 | Bettoun et al. |

FOREIGN PATENT DOCUMENTS

| | | |
|---|---|---|
| WO | 2012/050402 A2 | 4/2012 |
| WO | 2012/174452 A1 | 12/2012 |

OTHER PUBLICATIONS

Chauhan et al., The taming of the cell penetrating domain of the HIV Tat: myths and realities. J Control Release. Feb. 12, 2007;117(2):148-62.
Stauber et al., Intracellular trafficking and interactions of the HIV-1 Tat protein. Virology. Dec. 5, 1998;252(1):126-36.
Vitte et al., Intracellular delivery of peptides via association with ubiquitin or SUMO-1 coupled to protein transduction domains. BMC Biotechnol. Feb. 29, 2008;8:24, 11 pages.
Vyas et al., A TAT-frataxin fusion protein increases lifespan and cardiac function in a conditional Friedreich's ataxia mouse model. Hum Mol Genet. Mar. 15, 2012;21(6):1230-47.
International Search Report and Written Opinion for Application No. PCT/US2021/024534, dated Oct. 6, 2021, 15 pages.

*Primary Examiner* — Suzanne M Noakes
*Assistant Examiner* — Jae W Lee
(74) *Attorney, Agent, or Firm* — McCarter & English, LLP; Jill Mello; Yelena Margolin

(57) ABSTRACT

The present disclosure provides a fusion protein useful for treating a non-nuclear organelle associated disorder, such as a genetic disorder, e.g., Friedrich's Ataxia. The fusion protein may comprise a protein of interest to be delivered to a non-nuclear organelle; an organelle targeting sequence (OTS); a cell penetrating peptide (CPP); and a target enhancing sequence (TES); wherein the CPP is capable of interference with delivery of the protein of interest to the non-nuclear organelle; and wherein the TES prevents said interference by the CPP. The fusion protein may also comprise a protein of interest to be delivered to a non-nuclear organelle; a CPP and a TES. The present disclosure also provides methods for treating a non-nuclear organelle associated disorder by administering the fusion protein to a subject in need thereof.

13 Claims, 25 Drawing Sheets

Specification includes a Sequence Listing.

A.

B.

Frataxin and Mitochondrial Protein TOMM20 Immunolocalization Further to Transduction with TAT-GG-hFXN in Rat L6 Myoblasts Frataxin and Mitochondrial Protein TOMM20 Immunolocalization Further to Transfection with hFXN or TAT-GG-hFXN in Rat L6 Myoblasts

General Design of the Novel Variant hFXN Fusion Proteins

Frataxin and Mitochondrial Protein TOMM20 Immunolocalization in Rat L6 Myoblasts Further to Transfection with hFXN, or TAT-GG-hFXN, or a Novel hFXN Fusion Protein Panel a Panel b Panel c Panel d Panel e Panel f Panel g Panel h Panel i

Detection of hFXN in Cells Transfected with Novel hFXN Variants

MW: ~25KDa

MW: ~26KDa

MW: ~34KDa

MW: ~26KDa

Lane 1: hFXN (no TAT fusion)
Lane 2: TAT-GG-hFXN
Lane 3: TAT-GG-SUMO-hFXN
Lane 4: TAT-GG-Ubiquitin-hFXN
Lane 5: TAT-GG-EPLFAERK-hFXN
Lane 6: TAT-hFXN-NES

A

C

MW: ~65 KDa

MW: ~54KDa

MW: ~62KDa

MW: ~55KDa

SEQUENCE LISTING

```
Sequence total quantity: 88
SEQ ID NO: 1               moltype = AA   length = 210
FEATURE                    Location/Qualifiers
source                     1..210
                           mol_type = protein
                           organism = Homo sapiens
SEQUENCE: 1
MWTLGRRAVA GLLASPSPAQ AQTLTRVPRP AELAPLCGRR GLRTDIDATC TPRRASSNQR   60
GLNQIWNVKK QSVYLMNLRK SGTLGHPGSL DETTYERLAE ETLDSLAEFF EDLADKPYTF  120
EDYDVSFGSG VLTVKLGGDL GTYVINKQTP NKQIWLSSPS SGPKRYDWTG KNWVYSHDGV  180
SLHELLAAEL TKALKTKLDL SSLAYSGKDA                                  210

SEQ ID NO: 2               moltype = AA   length = 130
FEATURE                    Location/Qualifiers
source                     1..130
                           mol_type = protein
                           organism = Homo sapiens
SEQUENCE: 2
SGTLGHPGSL DETTYERLAE ETLDSLAEFF EDLADKPYTF EDYDVSFGSG VLTVKLGGDL   60
GTYVINKQTP NKQIWLSSPS SGPKRYDWTG KNWVYSHDGV SLHELLAAEL TKALKTKLDL  120
SSLAYSGKDA                                                        130

SEQ ID NO: 3               moltype = AA   length = 292
FEATURE                    Location/Qualifiers
source                     1..292
                           mol_type = protein
                           organism = Homo sapiens
SEQUENCE: 3
MPLHVKWPFP AVPPLTWTLA SSVVMGLVGT YSCFWTKYMN HLTVHNREVL YELIEKRGPA   60
TPLITVSNHQ SCMDDPHLWG ILKLRHIWNL KLMRWTPAAA DICFTKELHS HFFSLGKCVP  120
VCRGAEFFQA ENEGKGVLDT GRHMPGAGKR REKGDGVYQK GMDFILEKLN HGDWVHIFPE  180
GKVNMSSEFL RFKWGIGRLI AECHLNPIIL PLWHVGMNDV LPNSPPYFPR FGQKITVLIG  240
KPFSALPVLE RLRAENKSAV EMRKALTDFI QEEFQHLKTQ AEQLHNHLQP GR          292

SEQ ID NO: 4               moltype = AA   length = 359
FEATURE                    Location/Qualifiers
source                     1..359
                           mol_type = protein
                           organism = Homo sapiens
SEQUENCE: 4
MAAVSGLVRR PLREVSGLLK RRFHWTAPAA LQVTVRDAIN QGMDEELERD EKVFLLGEEV   60
AQYDGAYKVS RGLWKKYGDK RIIDTPISEM GFAGIAVGAA MAGLRPICEF MTFNFSMQAI  120
DQVINSAAKT YYMSGGLQPV PIVFRGPNGA SAGVAAQHSQ CFAAWYGHCP GLKVVSPWNS  180
EDAKGLIKSA IRDNNPVVVL ENELMYGVPF EFPPEAQSKD FLIPIGKAKI ERQGTHITVV  240
SHSRPVGHCL EAAAVLSKEG VECEVINMRT IRPMDMETIE ASVMKTNHLV TVEGGWPQFG  300
VGAEICARIM EGPAFNFLDA PAVRVTGADV PMPYAKILED NSIPQVKDII FAIKKTLNI   359

SEQ ID NO: 5               moltype = AA   length = 1394
FEATURE                    Location/Qualifiers
source                     1..1394
                           mol_type = protein
                           organism = Homo sapiens
SEQUENCE: 5
MAALLRSARW LLRAGAAPRL PLSLRLLPGG PGRLHAASYL PAARAGPVAG GLLSPARLYA   60
IAAKEKDIQE ESTFSSRKIS NQFDWALMRL DLSVRRTGRI PKKLLQKVFN DTCRSGGLGG  120
SHALLLLRSC GSLLPELKLE ERTEFAHRIW DTLQKLGAVY DVSHYNALLK VYLQNEYKFS  180
PTDFLAKMEE ANIQPNRVTY QRLIASYCNV GDIEGASKIL GFMKTKDLPV TEAVFSALVT  240
GHARAGDMEN AENILTVMRD AGIEPGPDTY LALLNAYAEK GDIDHVKQTL EKVEKSELHL  300
MDRDLLQIIF SFSKAGYPQY VSEILEKVTC ERRYIPDAMN LILLLVTEKL EDVALQILLA  360
CPVSKEDGPS VFGSFFLQHC VTMNTPVEKL TDYCKKLKEV QMHSFPLQFT LHCALLANKT  420
DLAKALMKAV KEEGFPIRPH YFWPLLVGRR KEKNVQGIIE ILKGMQELGV HPDQETYTDY  480
VIPCFDSVNS ARAILQENGC LSDSDMFSQA GLRSEAANGN LDFVLSFLKS NTLPISLQSI  540
RSSLLLGFRR SMNINLWSEI TELLYKDGRY CQEPRGPTEA VGYFLYNLID SMSDSEVQAK  600
EEHLRQYFHQ LEKMNVKIPE NIYRGIRNLL ESYHVPELIK DAHLLVESKN LDFQKTVQLT  660
SSELESTLET LKAENQPIRD VLKQLILVLC SEENMQKALE KLVELTQKLF ECDRDQMYYN  720
CCRHDKVEDA LNLKEEFDRL DSSAVLDTGK YVGLVRVLAK HGKLQDAINI LKEMKEKDVL  780
IKDTTALSFF HMLNGAALRG EIETVKQLHE AIVTLGLAEP STNISFPLVT VHLEKGDLST  840
ALEVAIDCYE KYKVLPRIHD VLCKLVEKGE TDLIQKAMDF VSQEQGEMVM LYDLFFAFLQ  900
TGNYKEAKKI IETPGIRARS ARLQWFCDRC VANNQVETKL KLVELTQKLF ECDRDQMYYN  960
LLKLYKINGD WQRADAVWNK IQEENVIPRE KTLRLLAEIL REGNQEVPFD VPELWYEDEK 1020
HSLNSSSAST TEPDFQKDIL IACRLNQKKG AYDIFLNAKE QNIVFNAETY SNLIKLLMSE 1080
DYFTQAMEVK AFAETHIKGF TLNDAANSRL IITQVRRDYL KEAVTTLKTV LDQQQTPSRL 1140
AVTRVIQALA MKGDVENIEV VQKMLNGLED SIGLSKMVPI NNIALAQIKN NNIDAAIENI 1200
ENMLTSENKV IEPQYFGLAY LFRKVIEEQL EPAVEKISIM AERLANQFAI YKPVTDFFLQ 1260
LVDAGKVDDA RALLQRCGAI AEQTPILLLF LLRNSRKQGK ASTVKSVLEL IPELNEKEEA 1320
YNSLMKSYVS EKDVTSAKAL YEHLTAKNTK LDDLFLKRYA SLLKYAGEPV PFIEPPESFE 1380
FYAQQLRKLR ENSS                                                  1394
```

```
SEQ ID NO: 6              moltype = AA  length = 109
FEATURE                   Location/Qualifiers
source                    1..109
                          mol_type = protein
                          organism = Homo sapiens
SEQUENCE: 6
MAASAARGAA ALRRSINQPV AFVRRIPWTA ASSQLKEHFA QFGHVRRCIL PFDKETGFHR   60
GLGWVQFSSE EGLRNALQQE NHIIDGVKVQ VHTRRPKLPQ TSDDEKKDF             109

SEQ ID NO: 7              moltype = AA  length = 465
FEATURE                   Location/Qualifiers
source                    1..465
                          mol_type = protein
                          organism = Homo sapiens
SEQUENCE: 7
MIVFVRFNSS HGFPVEVDSD TSIFQLKEVV AKRQGVPADQ LRVIFAGKEL RNDWTVQNCD   60
LDQQSIVHIV QRPWRKGQEM NATGGDDPRN AAGGCEREPQ SLTRVDLSSS VLPGDSVGLA  120
VILHTDSRKD SPPAGSPAGR SIYNSFYVYC KGPCQRVQPG KLRVQCSTCR QATLTLTQGP  180
SCWDDVLIPN RMSGECQSPH CPGTSAEFFF KCGAHPTSDK ETSVALHLIA TNSRNITCIT  240
CTDVRSPVLV FQCNSRHVIC LDCFHLYCVT RLNDRQFVHD PQLGYSLPCV AGCPNSLIKE  300
LHHFRILGEE QYNRYQQYGA EECVLQMGGV LCPRPGCGAG LLPEPDQRKV TCEGGNLGC   360
GPAFCRECKE AYHEGECSAV FEASGTTTQA YRVDERAAEQ ARWEAASKET IKKTTKPCPR  420
CHVPVEKNGG CMHMKCPQPQ CRLEWCWNCG CEWNRVCMGD HWFDV                 465

SEQ ID NO: 8              moltype = AA  length = 581
FEATURE                   Location/Qualifiers
source                    1..581
                          mol_type = protein
                          organism = Homo sapiens
SEQUENCE: 8
MAVRQALGRG LQLGRALLLR FTGKPGRAYG LGRPGPAAGC VRGERPGWAA GPGAEPRRVG   60
LGLPNRLRFF RQSVAGLAAR LQRQFVVRAW GCAGPCGRAV FLAFGLGLGL IEEKQAESRR  120
AVSACQEIQA IFTQKSKPGP DPLDTRRLQG FRLEEYLIGQ SIGKGCSAAV YEATMPTLPQ  180
NLEVTKSTGL LPGRGPGTSA PGEGQERAPG APAFPLAIKM MWNISAGSSS EAILNTMSQE  240
LVPASRVALA GEYGAVTYRK SKRGPKQLAP HPNIIRVLRA FTSSVPLLPG ALVDYPDVLP  300
SRLHPEGLGH GRTLFLVMKN YPCTLRQYLC VNTPSPRLAA MMLLQLLEGV DHLVQQGIAH  360
RDLKSDNILV ELDPDGCPWL VIADFGCCLA DESIGLQLPF SSWYVDRGGN GCLMAPEVST  420
ARPGPRAVID YSKADAWAVG AIAYEIFGLV NPFYGQGKAH LESRSYQEAQ LPALPESVPP  480
DVRQLVRALL QREASKRPSA RVAANVLHLS LWGEHILALK NLKLDKMVGW LLQQSAATLL  540
ANRLTEKCCV ETKMKMLFLA NLECETLCQA ALLLCSWRAA L                    581

SEQ ID NO: 9              moltype = AA  length = 189
FEATURE                   Location/Qualifiers
source                    1..189
                          mol_type = protein
                          organism = Homo sapiens
SEQUENCE: 9
MASKRALVIL AKGAEEMETV IPVDVMRRAG IKVTVAGLAG KDPVQCSRDV VICPDASLED   60
AKKEGPYDVV VLPGGNLGAQ NLSESAAVKE ILKEQENRKG LIAAICAGPT ALLAHEIGFG  120
SKVTTHPLAK DKMMNGGHYT YSENRVEKDG LILTSRGPGT SFEFALAIVE ALNGKEVAAQ  180
VKAPLVLKD                                                        189

SEQ ID NO: 10             moltype = AA  length = 80
FEATURE                   Location/Qualifiers
REGION                    1..80
                          note = Description of Artificial Sequence: Synthetic
                          polypeptide
source                    1..80
                          mol_type = protein
                          organism = synthetic construct
SEQUENCE: 10
MWTLGRRAVA GLLASPSPAQ AQTLTRVPRP AELAPLCGRR GLRTDIDATC TPRRASSNQR   60
GLNQIWNVKK QSVYLMNLRK                                             80

SEQ ID NO: 11             moltype = AA  length = 11
FEATURE                   Location/Qualifiers
source                    1..11
                          mol_type = protein
                          organism = Human immunodeficiency virus
SEQUENCE: 11
YGRKKRRQRR R                                                      11

SEQ ID NO: 12             moltype = AA  length = 30
FEATURE                   Location/Qualifiers
REGION                    1..30
                          note = Description of Artificial Sequence: Synthetic
                          polypeptide
source                    1..30
                          mol_type = protein
```

```
                        organism = synthetic construct
SEQUENCE: 12
GWTLNSAGYL LGPHAVGNHR SFSDKNGLTS                                30

SEQ ID NO: 13           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 13
INLKALAALA KKIL                                                 14

SEQ ID NO: 14           moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 14
GWTLNSAGYL LGKINLKALA ALAKKIL                                   27

SEQ ID NO: 15           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 15
RQIKIWFQNR RMKWKK                                               16

SEQ ID NO: 16           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 16
RRRRRRRRR                                                       9

SEQ ID NO: 17           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 17
DAAATATRGRS AASRPTERPR APARSASRPR RPVE                          34

SEQ ID NO: 18           moltype = AA  length = 76
FEATURE                 Location/Qualifiers
source                  1..76
                        mol_type = protein
                        organism = Homo sapiens
SEQUENCE: 18
MQIFVKTLTG KTITLEVEPS DTIENVKAKI QDKEGIPPDQ QRLIFAGKQL EDGRTLSDYN  60
IQKESTLHLV LRLRGG                                               76

SEQ ID NO: 19           moltype = AA  length = 4
FEATURE                 Location/Qualifiers
REGION                  1..4
                        note = Description of Unknown: caspase cleavage domain
                         sequence
source                  1..4
                        mol_type = protein
                        organism = unidentified
SEQUENCE: 19
DEVD                                                            4

SEQ ID NO: 20           moltype = AA  length = 8
FEATURE                 Location/Qualifiers
REGION                  1..8
                        note = Description of Unknown: calpain cleavage domain
```

```
                        sequence
source                  1..8
                        mol_type = protein
                        organism = unidentified
SEQUENCE: 20
EPLFAERK                                                                 8

SEQ ID NO: 21           moltype = AA  length = 4
FEATURE                 Location/Qualifiers
REGION                  1..4
                        note = Description of Unknown: calpain cleavage domain
                         sequence
source                  1..4
                        mol_type = protein
                        organism = unidentified
SEQUENCE: 21
LLVY                                                                     4

SEQ ID NO: 22           moltype = AA  length = 5
FEATURE                 Location/Qualifiers
REGION                  1..5
                        note = Description of Unknown: Enterokinase protease
                         cleavage site sequence
source                  1..5
                        mol_type = protein
                        organism = unidentified
SEQUENCE: 22
DDDDK                                                                    5

SEQ ID NO: 23           moltype = AA  length = 7
FEATURE                 Location/Qualifiers
REGION                  1..7
                        note = Description of Unknown: human Rhinovirus protease
                         cleavage site sequence
source                  1..7
                        mol_type = protein
                        organism = unidentified
SEQUENCE: 23
LEVLFQP                                                                  7

SEQ ID NO: 24           moltype = AA  length = 7
FEATURE                 Location/Qualifiers
source                  1..7
                        mol_type = protein
                        organism = Tobacco etch virus
SEQUENCE: 24
LEVLFGP                                                                  7

SEQ ID NO: 25           moltype = AA  length = 7
FEATURE                 Location/Qualifiers
source                  1..7
                        mol_type = protein
                        organism = Tobacco etch virus
SEQUENCE: 25
ENLYFQS                                                                  7

SEQ ID NO: 26           moltype = AA  length = 7
FEATURE                 Location/Qualifiers
REGION                  1..7
                        note = Description of Artificial Sequence: Synthetic peptide
VARIANT                 2..3
                        note = Any amino acid
VARIANT                 5
                        note = Any amino acid
source                  1..7
                        mol_type = protein
                        organism = synthetic construct
SEQUENCE: 26
EXXYXQG                                                                  7

SEQ ID NO: 27           moltype = AA  length = 7
FEATURE                 Location/Qualifiers
source                  1..7
                        mol_type = protein
                        organism = Tobacco vein mottling virus
SEQUENCE: 27
ETVRFQS                                                                  7

SEQ ID NO: 28           moltype = AA  length = 4
```

```
FEATURE                 Location/Qualifiers
REGION                  1..4
                        note = Description of Unknown: Factor Xa protease cleavage
                         site sequence
source                  1..4
                        mol_type = protein
                        organism = unidentified
SEQUENCE: 28
IEGR                                                                             4

SEQ ID NO: 29           moltype = AA  length = 4
FEATURE                 Location/Qualifiers
REGION                  1..4
                        note = Description of Unknown: Factor Xa protease cleavage
                         site sequence
source                  1..4
                        mol_type = protein
                        organism = unidentified
SEQUENCE: 29
IDGR                                                                             4

SEQ ID NO: 30           moltype = AA  length = 5
FEATURE                 Location/Qualifiers
REGION                  1..5
                        note = Description of Unknown: Thrombin cleavage site
                         sequence
source                  1..5
                        mol_type = protein
                        organism = unidentified
SEQUENCE: 30
LVPRS                                                                            5

SEQ ID NO: 31           moltype = AA  length = 5
FEATURE                 Location/Qualifiers
REGION                  1..5
                        note = Description of Unknown: Thrombin cleavage site
                         sequence
source                  1..5
                        mol_type = protein
                        organism = unidentified
SEQUENCE: 31
LVPGS                                                                            5

SEQ ID NO: 32           moltype = AA  length = 97
FEATURE                 Location/Qualifiers
REGION                  1..97
                        note = Description of Unknown: SUMO1 sequence
source                  1..97
                        mol_type = protein
                        organism = unidentified
SEQUENCE: 32
MSDQEAKPST EDLGDKKEGE YIKLKVIGQD SSEIHFKVKM TTHLKKLKES YCQRQGVPMN    60
SLRFLFEGQR IADNHTPKEL GMEEEDVIEV YQEQTGG                             97

SEQ ID NO: 33           moltype = AA  length = 95
FEATURE                 Location/Qualifiers
REGION                  1..95
                        note = Description of Unknown: SUMO2 sequence
source                  1..95
                        mol_type = protein
                        organism = unidentified
SEQUENCE: 33
MADEKPKEGV KTENNDHINL KVAGQDGSVV QFKIKRHTPL SKLMKAYCER QGLSMRQIRF    60
RFDGQPINET DTPAQLEMED EDTIDVFQQQ TGGVY                               95

SEQ ID NO: 34           moltype = AA  length = 103
FEATURE                 Location/Qualifiers
REGION                  1..103
                        note = Description of Unknown: SUMO3 sequence
source                  1..103
                        mol_type = protein
                        organism = unidentified
SEQUENCE: 34
MSEEKPKEGV KTENDHINLK VAGQDGSVVQ FKIKRHTPLS KLMKAYCERQ GLSMRQIRFR    60
FDGQPINETD TPAQLEMEDE DTIDVFQQQT GGVPESSLAG HSF                      103

SEQ ID NO: 35           moltype = AA  length = 95
FEATURE                 Location/Qualifiers
REGION                  1..95
```

```
                            note = Description of Unknown: SUMO4 sequence
source                      1..95
                            mol_type = protein
                            organism = unidentified
SEQUENCE: 35
MANEKPTEEV KTENNNHINL KVAGQDGSVV QFKIKRQTPL SKLMKAYCEP RGLSMKQIRF    60
RFGGQPISGT DKPAQLEMED EDTIDVFQQP TGGVY                               95

SEQ ID NO: 36               moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 36
LALKLAGLDL                                                           10

SEQ ID NO: 37               moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 37
LQKKLEELEL                                                           10

SEQ ID NO: 38               moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 38
MQELSNILNL                                                           10

SEQ ID NO: 39               moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 39
LPPLERLTL                                                            9

SEQ ID NO: 40               moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 40
LCQAFSDVIL                                                           10

SEQ ID NO: 41               moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 41
RTFDMHSLES SLIDIMR                                                   17

SEQ ID NO: 42               moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 42
TNLEALQKKL EELELDE                                                   17

SEQ ID NO: 43               moltype = AA  length = 17
```

```
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 43
RSFEMTEFNQ ALEEIKG                                                           17

SEQ ID NO: 44           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 44
GGGGSLVPRG SGGGGS                                                            16

SEQ ID NO: 45           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 45
GSGSGS                                                                        6

SEQ ID NO: 46           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 46
GSGSGSGSGS GSGSGS                                                            16

SEQ ID NO: 47           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 47
GGSGGHMGSG G                                                                 11

SEQ ID NO: 48           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 48
GGSGGSGGSG G                                                                 11

SEQ ID NO: 49           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 49
GGSGG                                                                         5

SEQ ID NO: 50           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 50
GGGSEGGGSE GGGSEGGG                                                          18
```

```
SEQ ID NO: 51              moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 51
AAGAATAA                                                                  8

SEQ ID NO: 52              moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 52
GGGGG                                                                     5

SEQ ID NO: 53              moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 53
GGSSG                                                                     5

SEQ ID NO: 54              moltype = AA   length = 11
FEATURE                    Location/Qualifiers
REGION                     1..11
                           note = Description of Artificial Sequence: Synthetic peptide
source                     1..11
                           mol_type = protein
                           organism = synthetic construct
SEQUENCE: 54
GSGGGTGGGS G                                                              11

SEQ ID NO: 55              moltype = AA   length = 321
FEATURE                    Location/Qualifiers
REGION                     1..321
                           note = Description of Artificial Sequence: Synthetic
                           polypeptide
source                     1..321
                           mol_type = protein
                           organism = synthetic construct
SEQUENCE: 55
MYGRKKRRQR RRGGMSDQEA KPSTEDLGDK KEGEYIKLKV IGQDSSEIHF KVKMTTHLKK          60
LKESYCQRQG VPMNSLRFLF EGQRIADNHT PKELGMEEED VIEVYQEQTG GMWTLGRRAV         120
AGLLASPSPA QAQTLTRVPR PAELAPLCGR RGLRTDIDAT CTPRRASSNQ RGLNQIWNVK         180
KQSVYLMNLR KSGTLGHPGS LDETTYERLA EETLDSLAEF FEDLADKPYT FEDYDVSFGS         240
GVLTVKLGGD LGTYVINKQT PNKQIWLSSP SSGPKRYDWT GKNWVYSHDG VSLHELLAAE         300
LTKALKTKLD LSSLAYSGKD A                                                  321

SEQ ID NO: 56              moltype = AA   length = 300
FEATURE                    Location/Qualifiers
REGION                     1..300
                           note = Description of Artificial Sequence: Synthetic
                           polypeptide
source                     1..300
                           mol_type = protein
                           organism = synthetic construct
SEQUENCE: 56
MYGRKKRRQR RRGGMQIFVK TLTGKTITLE VEPSDTIENV KAKIQDKEGI PPDQQRLIFA          60
GKQLEDGRTL SDYNIQKEST LHLVLRLRGG MWTLGRRAVA GLLASPSPAQ AQTLTRVPRP         120
AELAPLCGRR GLRTDIDATC TPRRASSNQR GLNQIWNVKK QSVYLMNLRK SGTLGHPGSL         180
DETTYERLAE ETLDSLAEFF EDLADKPYTF EDYDVSFGSG VLTVKLGGDL GTYVINKQTP         240
NKQIWLSSPS SGPKRYDWTG KNWVYSHDGV SLHELLAAEL TKALKTKLDL SSLAYSGKDA         300

SEQ ID NO: 57              moltype = AA   length = 228
FEATURE                    Location/Qualifiers
REGION                     1..228
                           note = Description of Artificial Sequence: Synthetic
                           polypeptide
source                     1..228
                           mol_type = protein
                           organism = synthetic construct
```

```
SEQUENCE: 57
MYGRKKRRQR RRGGDEVDMW TLGRRAVAGL LASPSPAQAQ TLTRVPRPAE LAPLCGRRGL    60
RTDIDATCTP RRASSNQRGL NQIWNVKKQS VYLMNLRKSG TLGHPGSLDE TTYERLAEET   120
LDSLAEFFED LADKPYTFED YDVSFGSGVL TVKLGGDLGT YVINKQTPNK QIWLSSPSSG   180
PKRYDWTGKN WVYSHDGVSL HELLAAELTK ALKTKLDLSS LAYSGKDA               228

SEQ ID NO: 58           moltype = AA   length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 58
MYGRKKRRQR RRGGEPLFAE RKMWTLGRRA VAGLLASPSP AQAQTLTRVP RPAELAPLCG    60
RRGLRTDIDA TCTPRRASSN QRGLNQIWNV KKQSVYLMNL RKSGTLGHPG SLDETTYERL   120
AEETLDSLAE FFEDLADKPY TFEDYDVSFG SGVLTVKLGG DLGTYVINKQ TPNKQIWLSS   180
PSSGPKRYDW TGKNWVYSHD GVSLHELLAA ELTKALKTKL DLSSLAYSGK DA           232

SEQ ID NO: 59           moltype = AA   length = 228
FEATURE                 Location/Qualifiers
REGION                  1..228
                        note = Description of Artificial Sequence: Synthetic
                         polypeptide
source                  1..228
                        mol_type = protein
                        organism = synthetic construct
SEQUENCE: 59
MYGRKKRRQR RRGGLLVYMW TLGRRAVAGL LASPSPAQAQ TLTRVPRPAE LAPLCGRRGL    60
RTDIDATCTP RRASSNQRGL NQIWNVKKQS VYLMNLRKSG TLGHPGSLDE TTYERLAEET   120
LDSLAEFFED LADKPYTFED YDVSFGSGVL TVKLGGDLGT YVINKQTPNK QIWLSSPSSG   180
PKRYDWTGKN WVYSHDGVSL HELLAAELTK ALKTKLDLSS LAYSGKDA               228

SEQ ID NO: 60           moltype = AA   length = 234
FEATURE                 Location/Qualifiers
REGION                  1..234
                        note = Description of Artificial Sequence: Synthetic
                         polypeptide
source                  1..234
                        mol_type = protein
                        organism = synthetic construct
SEQUENCE: 60
MYGRKKRRQR RRGGMWTLGR RAVAGLLASP SPAQAQTLTR VPRPAELAPL CGRRGLRTDI    60
DATCTPRRAS SNQRGLNQIW NVKKQSVYLM NLRKSGTLGH PGSLDETTYE RLAEETLDSL   120
AEFFEDLADK PYTFEDYDVS FGSGVLTVKL GGDLGTYVIN KQTPNKQIWL SSPSSGPKRY   180
DWTGKNWVYS HDGVSLHELL AAELTKALKT KLDLSSLAYS GKDALALKLA GLDL         234

SEQ ID NO: 61           moltype = AA   length = 234
FEATURE                 Location/Qualifiers
REGION                  1..234
                        note = Description of Artificial Sequence: Synthetic
                         polypeptide
source                  1..234
                        mol_type = protein
                        organism = synthetic construct
SEQUENCE: 61
MYGRKKRRQR RRGGMWTLGR RAVAGLLASP SPAQAQTLTR VPRPAELAPL CGRRGLRTDI    60
DATCTPRRAS SNQRGLNQIW NVKKQSVYLM NLRKSGTLGH PGSLDETTYE RLAEETLDSL   120
AEFFEDLADK PYTFEDYDVS FGSGVLTVKL GGDLGTYVIN KQTPNKQIWL SSPSSGPKRY   180
DWTGKNWVYS HDGVSLHELL AAELTKALKT KLDLSSLAYS GKDALQKKLE ELEL         234

SEQ ID NO: 62           moltype = DNA   length = 966
FEATURE                 Location/Qualifiers
misc_feature            1..966
                        note = Description of Artificial Sequence: Synthetic
                         polynucleotide
source                  1..966
                        mol_type = other DNA
                        organism = synthetic construct
SEQUENCE: 62
atgtacggcc gcaagaagcg gagacagagg cgccggggag gaatgtccga ccaggaggcc    60
aagccctcta ccgaggacct gggcgataag aaggagggca gtacatcaa gctgaaagtg   120
atcggccagg atagctccga gatccacttc aaggtgaaga tgaccacaca cctgaagaag   180
ctgaaggagt cttattgcca gcggcagggc gtgccaatga acagcctgag attcctgttt   240
gagggccaga ggatcgccga caatcacacc cccaaggagc tgggcatgga ggaggaggat   300
gtgatcgagg tgtatcagga gcagaccggc ggcatgtgga cactgggcag aagggcagtg   360
gcaggcctgc tggcatcccc atctcctgca caggcacaga ccctgacacg cgtgccacgg   420
cccgcagagc tggcaccact gtgcggccgg agaggcctga ggacagacat cgatgccacc   480
```

```
tgtacaccta gaagggcctc tagcaaccag cggggcctga accagatctg gaatgtgaag   540
aagcagtccg tgtacctgat gaatctgaga aagagcggca ccctgggaca ccctggctcc   600
ctggacgaga caacatatga gaggctggcc gaggagacac tggattctct ggccgagttc   660
tttgaggacc tggccgataa gccatacacc ttcgaggact atgatgtgag ctttggctcc   720
ggcgtgctga cagtgaagct gggaggcgac ctgggcacct acgtgatcaa caagcagaca   780
cctaataagc agatctggct gtcctctcct agctccggcc caaagcggta cgactgacc    840
ggcaagaact gggtgtattc tcacgatggc gtgagcctgc acgagctgct ggcagcagag   900
ctgaccaagg ccctgaagac aaagctggac ctgtctagcc tggcctatag cggcaaggat   960
gcctga                                                                966

SEQ ID NO: 63          moltype = DNA   length = 903
FEATURE                Location/Qualifiers
misc_feature           1..903
                       note = Description of Artificial Sequence: Synthetic
                       polynucleotide
source                 1..903
                       mol_type = other DNA
                       organism = synthetic construct
SEQUENCE: 63
atgtacggcc ggaagaagcg gagacagagg cgccggggag gaatgcagat cttcgtgaag   60
accctgacag gcaagaccat cacactggag gtggagccct ctgacaccat cgagaacgtg   120
aaggccaaga tccaggacaa ggagggcatc cccctgatc agcagcgcct gatctttgca    180
ggcaagcagc tggaggacgg acggaccctg tctgattata atatccagaa ggagagcaca   240
ctgcacctgg tgctgaggct gaggggagga atgtggaccc tggcagaag gcagtggca    300
ggcctgctgg cctctccaag cccagcacag gcacagaccc tgacaagagt gcctaggcca   360
gcagagctgg caccactgtg cggccggaga cagacatga tgccacctgt              420
acacccagaa gggccagctc caaccgagg ggcctgaacc agatctggaa tgtgaagaag    480
cagagcgtgt acctgatgaa tctgaggaag tccggcaccc tgggacaccc tggctctctg   540
gacgagacaa catatgagcg gctggccgag agacactgg attccctggc cgagttcttt    600
gaggacctgg ccgataagcc atacaccttc gaggactatg acgtgagctt cggctctggc   660
gtgctgacag tgaagctggg cggcgatctg gcacctacg tgatcaacaa gcagacacct   720
aataagcaga tctggctgtc tagcccctcc tctggcccta agatacga ctggaccggc     780
aagaactggg tgtatagcca cgatggcgtg tccctgcacg agctgctggc agcagagctg   840
accaaggccc tgaagacaaa gctggacctg agctccctgg cctattccgg caaggatgcc   900
tga                                                                  903

SEQ ID NO: 64          moltype = DNA   length = 687
FEATURE                Location/Qualifiers
misc_feature           1..687
                       note = Description of Artificial Sequence: Synthetic
                       polynucleotide
source                 1..687
                       mol_type = other DNA
                       organism = synthetic construct
SEQUENCE: 64
atgtacggca gaaagaagag gcggcagaga cgcaggggag gcgacgaggt ggatatgtgg   60
accctgggcc ggagagcagt ggcaggactg ctggcctctc ccagccctgc ccaggcccag   120
accctgacac gcgtgccaag gccagcagag ctggccacca tgtgcggccg caggggcctg   180
cggacagaca tcgatgccac ctgtacacct cggagagcca gctccaacca gagaggcctg   240
aaccagatct ggaatgtgaa gaagcagtcc gtgtacctga tgaatctgag gaagtctggc   300
accctgggac acccaggcag cctggacgag accacatacg agaggctggc cgaggagaca   360
ctggattctc tggccgagtt ctttgaggac ctggccgata gccctacac cttcgaggac    420
tacgacgtga gcttcggctc tggcgtgctg acagtgaagc tgggcggcga cctgggcacc   480
tacgtgatca acaagcagac acctaataag cagatctggc tgtctagccc ttcctctggc   540
ccaaaggagt acgactggac cggcaagaac tgggtgtaca gccacgatgg cgtgtccctg   600
cacgagctgc tggcagcaga gctgaccaag gcccctgaaga caaagctgga cctgagctcc   660
ctggcctaca gcggcaagga tgcctga                                        687

SEQ ID NO: 65          moltype = DNA   length = 699
FEATURE                Location/Qualifiers
misc_feature           1..699
                       note = Description of Artificial Sequence: Synthetic
                       polynucleotide
source                 1..699
                       mol_type = other DNA
                       organism = synthetic construct
SEQUENCE: 65
atgtatggaa ggaagaagag acggcagaga cggagaggag gcgagcccct gtttgctgag   60
cggaagatgt ggaccctggg aaggcgggca gtgcaggcc tgctggcaag cccatcccct    120
gcacaggcac agaccctgac aagggtgcca cggcccgcag agctggcacc actgtgcggc   180
aggcggggcc tgagaaccga catcgatgcc acctgtacac ctagaagggc cagctccaac   240
cagagggggc tgaaccagat ctggaatgtg aagaagcaga gcgtgtacct gatgaatctg   300
aggaagagcg gcaccctggg acacccaggc tccctggacg agacaacata cgagaggctg   360
gccgaggaga cactgggatc cctggccgag ttctttgagg acctggccga taagcccac    420
accttcgagg actacgacgt gagcttcggc agcggcgtgc tgacagtgaa gctgggaggc   480
gacctgggca cctacgtgat caacaagcag acacctaata gcagatctg gctgtctagc    540
ccttcctctg gcccaaagcg gtacgactgg accggcaaga actgggtgta ctcccacgat   600
ggcgtgtctc tgcacgagct gctggcagca gagctgacaa agcactgaa acaaaaactg    660
gacctgtcat cactggcata ctctggaaag gacgcataa                           699
```

```
SEQ ID NO: 66            moltype = DNA  length = 687
FEATURE                  Location/Qualifiers
misc_feature             1..687
                         note = Description of Artificial Sequence: Synthetic
                         polynucleotide
source                   1..687
                         mol_type = other DNA
                         organism = synthetic construct
SEQUENCE: 66
atgtacggca gaaagaagag gcggcagaga cgcaggggag gactgctggt gtacatgtgg    60
accctgggcc ggagagcagt ggcaggactg ctggcctctc ccagcccagc ccaggcccag   120
accctgacac gcgtgccaag gccagcgaga ctggcaccac tgtgcggccg caggggcctg   180
cggacagaca tcgatgccac ctgtacacct cggagagcca gctccaacca gagaggcctg   240
aaccagatct ggaatgtgaa gaagcagtcc gtgtacctga tgaatctgag gaagtctggc   300
accctgggac acccaggcag cctgacgag accacatacg agaggctggc cgaggagaca   360
ctggattctc tggccgagtt ctttgaggac ctggccgata agcccacac cttcgaggac   420
tacgacgtga gcttcggctc tggcgtgctg acagtgaagc tgggcggcga cctgggcacc   480
tacgtgatca acaagcagac acctaataag cagatctggc tgtctagccc ttcctctggc   540
ccaaagaggt acgactggac cggcaagaac tgggtgtaca gccacgatgg cgtgtccctg   600
cacgagctgc tggcagcaga gctgaccaag gccctgaaga caaagctgga cctgagctcc   660
ctggcctaca gcgcaaggc tgcctga                                         687

SEQ ID NO: 67            moltype = DNA  length = 699
FEATURE                  Location/Qualifiers
misc_feature             1..699
                         note = Description of Artificial Sequence: Synthetic
                         polynucleotide
source                   1..699
                         mol_type = other DNA
                         organism = synthetic construct
SEQUENCE: 67
atgtatggaa ggaagaagag acggcagaga cggagaggag gcgagcccct gtttgctgag    60
cggaagatgt ggaccctggg aaggcgggca gtggcaggcc tgctggcaag cccatcccct   120
gcacaggcac agaccctgac aagggtgcca cggcccgcag agctggcacc actgtgcggc   180
aggcggggcc tgagaaccga catcgatgcc acctgtacac ctagaagggc cagctccaac   240
cagagggcc tgaaccagat ctggaatgtg aagaagcaga gcgtgtacct gatgaatctg   300
aggaagagcg gcaccctggg acacccaggc tcccttgacg agacaacata cgagaggctg   360
gccgaggaga cacttggattc cctggccgag ttctttgagg acctggccga taagccctac   420
accttcgagg actacgacgt gagcttcggc agcggcgtgc tgacagtgaa gctgggaggc   480
gacctgggca cctacgtgat caacaagcag acacctaata gcagatctg gctgtctagc   540
ccttcctctg gcccaaagcg gtacgactgg accggcaaga actgggtgta ctcccacgat   600
ggcgtgtctc tgcacgagct gctggcagca gagctgacaa agcactgaa aacaaaactg   660
gacctgtcat cactggcata ctctggaaag gacgcataa                           699

SEQ ID NO: 68            moltype = DNA  length = 705
FEATURE                  Location/Qualifiers
misc_feature             1..705
                         note = Description of Artificial Sequence: Synthetic
                         polynucleotide
source                   1..705
                         mol_type = other DNA
                         organism = synthetic construct
SEQUENCE: 68
atgtacggca gaaagaagag gcggcagaga cgcaggggag gaatgtggac cctgggccgg    60
agagcagtgg caggactgct ggcctctccc agcccgccc aggcccagac cctgacacgc   120
gtgccaaggc cagcagagct ggcaccactg tgcggccgca ggggcctgcg gacagacatc   180
gatgccacct gtacacctcg agagccagc tccaaccaga gaggcctgaa ccagatctgg   240
aatgtgaaga agcagtccgt gtacctgatg aatctgagga gtctggcac cctgggacac   300
ccaggcagc tggacgagac cacatacgag aggctggccg aggagacact ggattctctg   360
gccgagttct ttgaggacct ggccgataag cccacacct cgaggacta cgacgtgagc   420
ttcggctctg gcgtgctgac agtgaagctg ggcggcgacc tgggcaccta cgtgatcaac   480
aagcagacac taataagca gatctggctg tctagccctt cctctggccc aaagaggtac   540
gactggaccg gcaagaactg ggtgtacagc cacgatggcg tgtccctgca cgagctgctg   600
gcagcagagc tgaccaaggc cctgaagaca aagctggacc tgagctcct ggcctacagc   660
ggcaaggatg ccctgcagaa gaagctggag gagctgagc tgtga                    705

SEQ ID NO: 69            moltype = AA  length = 555
FEATURE                  Location/Qualifiers
REGION                   1..555
                         note = Description of Artificial Sequence: Synthetic
                         polypeptide
source                   1..555
                         mol_type = protein
                         organism = synthetic construct
SEQUENCE: 69
MYGRKKRRQR RRGGMQIFVK TLTGKTITLE VEPSDTIENV KAKIQDKEGI PPDQQRLIFA    60
GKQLEDGRTL SDYNIQKEST LHLVLRLRGG MIVFVRFNSS HGFPVEVDSD TSIFQLKEVV   120
AKRQGVPADQ LRVIFAGKEL RNDWTVQNCD LDQQSIVHIV QRPWRKGQEM NATGGDDPRN   180
```

```
AAGGCEREPQ  SLTRVDLSSS  VLPGDSVGLA  VILHTDSRKD  SPPAGSPAGR  SIYNSFYVYC   240
KGPCQRVQPG  KLRVQCSTCR  QATLTLTQGP  SCWDDVLIPN  RMSGECQSPH  CPGTSAEFFF   300
KCGAHPTSDK  ETSVALHLIA  TNSRNITCIT  CTDVRSPVLV  FQCNSRHVIC  LDCFHLYCVT   360
RLNDRQFVHD  PQLGYSLPCV  AGCPNSLIKE  LHHFRILGEE  QYNRYQQYGA  EECVLQMGGV   420
LCPRPGCGAG  LLPEPDQRKV  TCEGGNGLGC  GFAFCRECKE  AYHEGECSAV  FEASGTTTQA   480
YRVDERAAEQ  ARWEAASKET  IKKTTKPCPR  CHVPVEKNGG  CMHMKCPQPQ  CRLEWCWNCG   540
CEWNRVCMGD  HWFDV                                                       555

SEQ ID NO: 70           moltype = AA  length = 487
FEATURE                 Location/Qualifiers
REGION                  1..487
                        note = Description of Artificial Sequence: Synthetic
                         polypeptide
source                  1..487
                        mol_type = protein
                        organism = synthetic construct
SEQUENCE: 70
MYGRKKRRQR  RRGGEPLFAE  RKMIVFVRFN  SSHGFPVEVD  SDTSIFQLKE  VVAKRQGVPA    60
DQLRVIFAGK  ELRNDWTVQN  CDLDQQSIVH  IVQRPWRKGQ  EMNATGGDDP  RNAAGGCERE   120
PQSLTRVDLS  SSVLPGDSVG  LAVILHTDSR  KDSPPAGSPA  GRSIYNSFYV  YCKGPCQRVQ   180
PGKLRVQCST  CRQATLTLTQ  GPSCWDDVLI  PNRMSGECQS  PHCPGTSAEF  FFKCGAHPTS   240
DKETSVALHL  IATNSRNITC  ITCTDVRSPV  LVFQCNSRHV  ICLDCFHLYC  VTRLNDRQFV   300
HDPQLGYSLP  CVAGCPNSLI  KELHHFRILG  EEQYNRYQQY  GAEECVLQMG  GVLCPRPGCG   360
AGLLPEPDQR  KVTCEGGNGL  GCGFAFCREC  KEAYHEGECS  AVFEASGTTT  QAYRVDERAA   420
EQARWEAASK  ETIKKTTKPC  PRCHVPVEKN  GGCMHMKCPQ  PQCRLEWCWN  CGCEWNRVCM   480
GDHWFDV                                                                 487

SEQ ID NO: 71           moltype = AA  length = 489
FEATURE                 Location/Qualifiers
REGION                  1..489
                        note = Description of Artificial Sequence: Synthetic
                         polypeptide
source                  1..489
                        mol_type = protein
                        organism = synthetic construct
SEQUENCE: 71
MYGRKKRRQR  RRGGMIVFVR  FNSSHGFPVE  VDSDTSIFQL  KEVVAKRQGV  PADQLRVIFA    60
GKELRNDWTV  QNCDLDQQSI  VHIVQRPWRK  GQEMNATGGD  DPRNAAGGCE  REPQSLTRVD   120
LSSSVLPGDS  VGLAVILHTD  SRKDSPPAGS  PAGRSIYNSF  YVYCKGPCQR  VQPGKLRVQC   180
STCRQATLTL  TQGPSCWDDV  LIPNRMSGEC  QSPHCPGTSA  EFFFKCGAHP  TSDKETSVAL   240
HLIATNSRNI  TCITCTDVRS  PVLVFQCNSR  HVICLDCFHL  YCVTRLNDRQ  FVHDPQLGYS   300
LPCVAGCPNS  LIKELHHFRI  LGEEQYNRYQ  QYGAEECVLQ  MGGVLCPRPG  CGAGLLPEPD   360
QRKVTCEGGN  GLGCGFAFCR  ECKEAYHEGE  CSAVFEASGT  TTQAYRVDER  AAEQARWEAA   420
SKETIKKTTK  PCPRCHVPVE  KNGGCMHMKC  PQPQCRLEWC  WNCGCEWNRV  CMGDHWFDVL   480
ALKLAGLDL                                                               489

SEQ ID NO: 72           moltype = AA  length = 806
FEATURE                 Location/Qualifiers
source                  1..806
                        mol_type = protein
                        organism = Homo sapiens
SEQUENCE: 72
MQFFGRLVNT  FSGVTNLFSN  PFRVKEVAVA  DYTSSDRVRE  EGQLILFQNT  PNRTWDCVLV    60
NPRNSQSGFR  LFQLELEADA  LVNFHQYSSQ  LLPFYESSPQ  VLHTEVLQHL  TDLIRNHPSW   120
SVAHLAVELG  IRECFHHSRI  ISCANCAENE  EGCTPLHLAC  RKGDGEILVE  LVQYCHTQMD   180
VTDYKGETVF  HYAVQGDNSQ  VLQLLGRNAV  AGLNQVNNQG  LTPLHLACQL  GKQEMVRVLL   240
LCNARCNIMG  PNGYPIHSAM  KFSQKGCAEM  IISMDSSQIH  SKDPRYGASP  LHWAKNAEMA   300
RMLLKRGCNV  NSTSSAGNTA  LHVAVMRNRF  DCAIVLLTHG  ANADARGEHG  NTPLHLAMSK   360
DNVEMIKALI  VFGAEVDTPN  DFGETPTFLA  SKIGRLVTRK  VITLLRTVG   AEYCFPPIHG   420
VPAEQGSAAP  HHPFSLERAQ  PPPISLNNLE  LQDDLMHISRA  RKPAFILGSM RDEKRTHDHL   480
LCLDGGGVKG  LIIIQLLIAI  EKASGVATKD  LFDVVAGTST  GGILALAILH  SKSMAYRGM   540
YFRMKDEVFR  GSRPYESGPL  EEFLKREFGE  HTKMTDVRKP  KVMLTGTLSD  RQPAELHLFR   600
NYDAPETVRE  PRFNQNVNLR  PPAQPSDQLV  WRAARSSGNA  TYFRPNGRF   LDGGLLANNP   660
TLDAMTEIHE  YNQDLIRKGQ  ANKVKKLSIV  VSLGTGRSPQ  VPVTCVDVFR  PSNPWELAKT   720
VFGAKELGKM  VVDCCTDPDG  RAVDRARAWC  EMVGIQYFRL  NPQLGTDIML  DEVSDTVLVN   780
ALWETEVYIY  EHREEFQKLI  QLLLSP                                          806

SEQ ID NO: 73           moltype = AA  length = 752
FEATURE                 Location/Qualifiers
source                  1..752
                        mol_type = protein
                        organism = Homo sapiens
SEQUENCE: 73
MQFFGRLVNT  FSGVTNLFSN  PFRVKEVAVA  DYTSSDRVRE  EGQLILFQNT  PNRTWDCVLV    60
NPRNSQSGFR  LFQLELEADA  LVNFHQYSSQ  LLPFYESSPQ  VLHTEVLQHL  TDLIRNHPSW   120
SVAHLAVELG  IRECFHHSRI  ISCANCAENE  EGCTPLHLAC  RKGDGEILVE  LVQYCHTQMD   180
VTDYKGETVF  HYAVQGDNSQ  VLQLLGRNAV  AGLNQVNNQG  LTPLHLACQL  GKQEMVRVLL   240
LCNARCNIMG  PNGYPIHSAM  KFSQKGCAEM  IISMDSSQIH  SKDPRYGASP  LHWAKNAEMA   300
RMLLKRGCNV  NSTSSAGNTA  LHVAVMRNRF  DCAIVLLTHG  ANADARGEHG  NTPLHLAMSK   360
```

```
DNVEMIKALI VFGAEVDTPN DFGETPTFLA SKIGRQLQDL MHISRARKPA FILGSMRDEK    420
RTHDHLLCLD GGGVKGLIII QLLIAIEKAS GVATKDLFDW VAGTSTGGIL ALAILHSKSM    480
AYMRGMYFRM KDEVFRGSRP YESGPLEEFL KREFGEHTKM TDVRKPKVML TGTLSDRQPA    540
ELHLFRNYDA PETVREPRFN QNVNLRPPAQ PSDQLVWRAA RSSGAAPTYF RPNGRFLDGG    600
LLANNPTLDA MTEIHEYNQD LIRKGQANKV KKLSIVVSLG TGRSPQVPVT CVDVFRPSNP    660
WELAKTVFGA KELGKMVVDC CTDPDGRAVD RARAWCEMVG IQYFRLNPQL GTDIMLDEVS    720
DTVLVNALWE TEVYIYEHRE EFQKLIQLLL SP                                  752

SEQ ID NO: 74            moltype = AA  length = 752
FEATURE                  Location/Qualifiers
source                   1..752
                         mol_type = protein
                         organism = Homo sapiens
SEQUENCE: 74
MQFFGRLVNT FSGVTNLFSN PFRVKEVAVA DYTSSDRVRE EGQLILFQNT PNRTWDCVLV     60
NPRNSQSGFR LFQLELEADA LVNFHQYSSQ LLPFYESSPQ VLHTEVLQHL TDLIRNHPSW    120
SVAHLAVELG IRECFHHSRI ISCANCAENE EGCTPLHLAC RKGDGEILVE LVQYCHTQMD    180
VTDYKGETVF HYAVQGDNSQ VLQLLGRNAV AGLNQVNNQG LTPLHLACQL GKQEMVRVLL    240
LCNARCNIMG PNGYPIHSAM KFSQKGCAEM IISMDSSQIH SKDPRYGASP LHWAKNAEMA    300
RMLLKRGCNV NSTSSAGNTA LHVAVMRNRF DCAIVLLTHG ANADARGEHG NTPLHLAMSK    360
DNVEMIKALI VFGAEVDTPN DFGETPTFLA SKIGRQLQDL MHISRARKPA FILGSMRDEK    420
RTHDHLLCLD GGGVKGLIII QLLIAIEKAS GVATKDLFDW VAGTSTGGIL ALAILHSKSM    480
AYMRGMYFRM KDEVFRGSRP YESGPLEEFL KREFGEHTKM TDVRKPKVML TGTLSDRQPA    540
ELHLFRNYDA PETVREPRFN QNVNLRPPAQ PSDQLVWRAA RSSGAAPTYF RPNGRFLDGG    600
LLANNPTLDA MTEIHEYNQD LIRKGQANKV KKLSIVVSLG TGRSPQVPVT CVDVFRPSNP    660
WELAKTVFGA KELGKMVVDC CTDPDGRAVD RARAWCEMVG IQYFRLNPQL GTDIMLDEVS    720
DTVLVNALWE TEVYIYEHRE EFQKLIQLLL SP                                  752

SEQ ID NO: 75            moltype = AA  length = 806
FEATURE                  Location/Qualifiers
source                   1..806
                         mol_type = protein
                         organism = Homo sapiens
SEQUENCE: 75
MQFFGRLVNT FSGVTNLFSN PFRVKEVAVA DYTSSDRVRE EGQLILFQNT PNRTWDCVLV     60
NPRNSQSGFR LFQLELEADA LVNFHQYSSQ LLPFYESSPQ VLHTEVLQHL TDLIRNHPSW    120
SVAHLAVELG IRECFHHSRI ISCANCAENE EGCTPLHLAC RKGDGEILVE LVQYCHTQMD    180
VTDYKGETVF HYAVQGDNSQ VLQLLGRNAV AGLNQVNNQG LTPLHLACQL GKQEMVRVLL    240
LCNARCNIMG PNGYPIHSAM KFSQKGCAEM IISMDSSQIH SKDPRYGASP LHWAKNAEMA    300
RMLLKRGCNV NSTSSAGNTA LHVAVMRNRF DCAIVLLTHG ANADARGEHG NTPLHLAMSK    360
DNVEMIKALI VFGAEVDTPN DFGETPTFLA SKIGRLVTRK AILTLLRTVG AEYCFPPIHG    420
VPAEQGSAAP HHPFSLERAQ PPPISLNNLE LQDLMHISRA RKPAFILGSM RDEKRTHDHL    480
LCLDGGGVKG LIIIQLLIAI EKASGVATKD LFDWVAGTST GGILALAILH SKSMAYMRGM    540
YFRMKDEVFR GSRPYESGPL EEFLKREFGE HTKMTDVRKP KVMLTGTLSD RQPAELHLFR    600
NYDAPETVRE PRFNQNVNLR PPAQPSDQLV WRAARSSGAA PTYFRPNGRF LDGGLLANNP    660
TLDAMTEIHE YNQDLIRKGQ ANKVKKLSIV VSLGTGRSPQ VPVTCVDVFR PSNPWELAKT    720
VFGAKELGKM VVDCCTDPDG RAVDRARAWC EMVGIQYFRL NPQLGTDIML DEVSDTVLVN    780
ALWETEVYIY EHREEFQKLI QLLLSP                                         806

SEQ ID NO: 76            moltype = AA  length = 752
FEATURE                  Location/Qualifiers
source                   1..752
                         mol_type = protein
                         organism = Homo sapiens
SEQUENCE: 76
MQFFGRLVNT FSGVTNLFSN PFRVKEVAVA DYTSSDRVRE EGQLILFQNT PNRTWDCVLV     60
NPRNSQSGFR LFQLELEADA LVNFHQYSSQ LLPFYESSPQ VLHTEVLQHL TDLIRNHPSW    120
SVAHLAVELG IRECFHHSRI ISCANCAENE EGCTPLHLAC RKGDGEILVE LVQYCHTQMD    180
VTDYKGETVF HYAVQGDNSQ VLQLLGRNAV AGLNQVNNQG LTPLHLACQL GKQEMVRVLL    240
LCNARCNIMG PNGYPIHSAM KFSQKGCAEM IISMDSSQIH SKDPRYGASP LHWAKNAEMA    300
RMLLKRGCNV NSTSSAGNTA LHVAVMRNRF DCAIVLLTHG ANADARGEHG NTPLHLAMSK    360
DNVEMIKALI VFGAEVDTPN DFGETPTFLA SKIGRQLQDL MHISRARKPA FILGSMRDEK    420
RTHDHLLCLD GGGVKGLIII QLLIAIEKAS GVATKDLFDW VAGTSTGGIL ALAILHSKSM    480
AYMRGMYFRM KDEVFRGSRP YESGPLEEFL KREFGEHTKM TDVRKPKVML TGTLSDRQPA    540
ELHLFRNYDA PETVREPRFN QNVNLRPPAQ PSDQLVWRAA RSSGAAPTYF RPNGRFLDGG    600
LLANNPTLDA MTEIHEYNQD LIRKGQANKV KKLSIVVSLG TGRSPQVPVT CVDVFRPSNP    660
WELAKTVFGA KELGKMVVDC CTDPDGRAVD RARAWCEMVG IQYFRLNPQL GTDIMLDEVS    720
DTVLVNALWE TEVYIYEHRE EFQKLIQLLL SP                                  752

SEQ ID NO: 77            moltype = AA  length = 752
FEATURE                  Location/Qualifiers
source                   1..752
                         mol_type = protein
                         organism = Homo sapiens
SEQUENCE: 77
MQFFGRLVNT FSGVTNLFSN PFRVKEVAVA DYTSSDRVRE EGQLILFQNT PNRTWDCVLV     60
NPRNSQSGFR LFQLELEADA LVNFHQYSSQ LLPFYESSPQ VLHTEVLQHL TDLIRNHPSW    120
SVAHLAVELG IRECFHHSRI ISCANCAENE EGCTPLHLAC RKGDGEILVE LVQYCHTQMD    180
VTDYKGETVF HYAVQGDNSQ VLQLLGRNAV AGLNQVNNQG LTPLHLACQL GKQEMVRVLL    240
```

```
LCNARCNIMG PNGYPIHSAM KFSQKGCAEM IISMDSSQIH SKDPRYGASP LHWAKNAEMA      300
RMLLKRGCNV NSTSSAGNTA LHVAVMRNRF DCAIVLLTHG ANADARGEHG NTPLHLAMSK      360
DNVEMIKALI VFGAEVDTPN DFGETPTFLA SKIGRQLQDL MHISRARKPA FILGSMRDEK      420
RTHDHLLCLD GGGVKGLIII QLLIAIEKAS GVATKDLFDW VAGTSTGGIL ALAILHSKSM      480
AYMRGMYFRM KDEVFRGSRP YESGPLEEFL KREFGEHTKM TDVRKPKVML TGTLSDRQPA      540
ELHLFRNYDA PETVREPRFN QNVNLRPPAQ PSDQLVWRAA RSSGAAPTYF RPNGRFLDGG      600
LLANNPTLDA MTEIHEYNQD LIRKGQANKV KKLSIVVSLG TGRSPQVPVT CVDVFRPSNP      660
WELAKTVFGA KELGKMVVDC CTDPDGRAVD RARAWCEMVG IQYFRLNPQL GTDIMLDEVS      720
DTVLVNALWE TEVYIYEHRE EFQKLIQLLL SP                                   752

SEQ ID NO: 78           moltype = AA   length = 628
FEATURE                 Location/Qualifiers
source                  1..628
                        mol_type = protein
                        organism = Homo sapiens
SEQUENCE: 78
MDVTDYKGET VFHYAVQGDN SQVLQLLGRN AVAGLNQVNN QGLTPLHLAC QLGKQEMVRV      60
LLLCNARCNI MGPNGYPIHS AMKFSQKGCA EMIISMDSSQ IHSKDPRYGA SPLHWAKNAE     120
MARMLLKRGC NVNSTSSAGN TALHVAVMRN RFDCAIVLLT HGANADARGE HGNTPLHLAM     180
SKDNVEMIKA LIVFGAEVDT PNDFGETPTF LASKIGRLVT RKAILTLLRT VGAEYCFPPI     240
HGVPAEQGSA APHHPFSLER AQPPPISLNN LELQDLMHIS RARKPAFILG SMRDEKRTHD     300
HLLCLDGGGV KGLIIIQLLI AIEKASGVAT KDLFDWVAGT STGGILALAI LHSKSMAYMR     360
GMYFRMKDEV FRGSRPYESG PLEEFLKREF GEHTKMTDVR KPKVMLTGTL SDRQPAELHL     420
FRNYDAPETV REPRFNQNVN LRPPAQPSDQ LVWRAASSG AAPTYFRPNG RFLDGGLLAN      480
NPTLDAMTEI HEYNQDLIRK GQANKVKKLS IVVSLGTGRS PQVPVTCVDV FRPSNPWELA     540
KTVFGAKELG KMVVDCCTDP DGRAVDRARA WCEMVGIQYF RLNPQLGTDI MLDEVSDTVL     600
VNALWETEVY IYEHREEFQK LIQLLLSP                                        628

SEQ ID NO: 79           moltype = AA   length = 580
FEATURE                 Location/Qualifiers
source                  1..580
                        mol_type = protein
                        organism = Homo sapiens
SEQUENCE: 79
MGRSWWSWCS TATLRWMSPT TRERPSSIML SRVTILRCCR CAEMIISMDS SQIHSKDPRY      60
GASPLHWAKN AEMARMLLKR GCNVNSTSSA GNTALHVAVM RNRFDCAIVL LTHGANADAR     120
GEHGNTPLHL AMSKDNVEMI KALIVFGAEV DTPNDFGETP TFLASKIGRL VTRKAILTLL     180
RTVGAEYCFP PIHGVPAEQG SAAPHHPFSL ERAQPPPISL NNLELQDLMH ISRARKPAFI     240
LGSMRDEKRT HDHLLCLDGG GVKGLIIIQL LIAIEKASGV ATKDLFDWVA GTSTGGILAL     300
AILHSKSMAY MRGMYFRMKD EVFRGSRPYE SGPLEEFLKR EFGEHTKMTD VRKPKVMLTG     360
TLSDRQPAEL HLFRNYDAPE TVREPRFNQN VNLRPPAQPS DQLVWRAARS SGAAPTYFRP     420
NGRFLDGGLL ANNPTLDAMT EIHEYNQDLI RKGQANKVKK LSIVVSLGTG RSPQVPVTCV     480
DVFRPSNPWE LAKTVFGAKE LGKMVVDCCT DPDGRAVDRA RAWCEMVGIQ YFRLNPQLGT     540
DIMLDEVSDT VLVNALWETE VYIYEHREEF QKLIQLLLSP                           580

SEQ ID NO: 80           moltype = AA   length = 574
FEATURE                 Location/Qualifiers
source                  1..574
                        mol_type = protein
                        organism = Homo sapiens
SEQUENCE: 80
MDVTDYKGET VFHYAVQGDN SQVLQLLGRN AVAGLNQVNN QGLTPLHLAC QLGKQEMVRV      60
LLLCNARCNI MGPNGYPIHS AMKFSQKGCA EMIISMDSSQ IHSKDPRYGA SPLHWAKNAE     120
MARMLLKRGC NVNSTSSAGN TALHVAVMRN RFDCAIVLLT HGANADARGE HGNTPLHLAM     180
SKDNVEMIKA LIVFGAEVDT PNDFGETPTF LASKIGRQLQ DLMHISRARK PAFILGSMRD     240
EKRTHDHLLC LDGGGVKGLI IIQLLIAIEK ASGVATKDLF DWVAGTSTGG ILALAILHSK     300
SMAYMRGMYF RMKDEVFRGS RPYESGPLEE FLKREFGEHT KMTDVRKPKV MLTGTLSDRQ     360
PAELHLFRNY DAPETVREPR FNQNVNLRPP AQPSDQLVWR AARSSGAAPT YFRPNGRFLD     420
GGLLANNPTL DAMTEIHEYN QDLIRKGQAN KVKKLSIVVS LGTGRSPQVP VTCVDVFRPS     480
NPWELAKTVF GAKELGKMVV DCCTDPDGRA VDRARAWCEM VGIQYFRLNP QLGTDIMLDE     540
VSDTVLVNAL WETEVYIYEH REEFQKLIQL LLSP                                 574

SEQ ID NO: 81           moltype = AA   length = 321
FEATURE                 Location/Qualifiers
REGION                  1..321
                        note = Description of Artificial Sequence: Synthetic
                        polypeptide
source                  1..321
                        mol_type = protein
                        organism = synthetic construct
SEQUENCE: 81
MYGRKKRRQR RGGSDSEVN QEAKPEVKPE VKPETHINLK VSDGSSEIFF KIKKTTPLRR       60
LMEAFAKRQG KEMDSLRFLY DGIRIQADQT PEDLDMEDND IIEAHREQIG GMWTLGRRAV     120
AGLLASPSPA QAQTLTRVPR PAELAPLCGR RGLRTDIDAT CTPRRASSNQ RGLNQIWNVK     180
KQSVYLMNLR KSGTLGHPGS LDETTYERLA EETLDSLAEF FEDLADKPYT FEDYDVSFGS     240
GVLTVKLGGD LGTYVINKQT PNKQIWLSSP SSGPKRYDWT GKNWVYSHDG VSLHELLAAE     300
LTKALKTKLD LSSSLAYSGKD A                                              321

SEQ ID NO: 82           moltype = AA   length = 582
```

```
FEATURE                 Location/Qualifiers
REGION                  1..582
                        note = Description of Artificial Sequence: Synthetic
                         polypeptide
source                  1..582
                        mol_type = protein
                        organism = synthetic construct
SEQUENCE: 82
HHHHHHSDSE VNQEAKPEVK PEVKPETHIN LKVSDGSSEI FFKIKKTTPL RRLMEAFAKR    60
QGKEMDSLRF LYDGIRIQAD QTPEDLDMED NDIIEAHREQ IGGMYGRKKR RQRRRGGMIV   120
FVRFNSSHGF PVEVDSDTSI FQLKEVVAKR QGVPADQLRV IFAGKELRND WTVQNCDLDQ   180
QSIVHIVQRP WRKGQEMNAT GGDDPRNAAG GCEREPQSLT RVDLSSSVLP GDSVGLAVIL   240
HTDSRKDSPP AGSPAGRSIY NSFYVYCKGP CQRVQPGKLR VQCSTCRQAT LTLTQGPSCW   300
DDVLIPNRMS GECQSPHCPG TSAEFFFKCG AHPTSDKETS VALHLIATNS RNITCITCTD   360
VRSPVLVFQC NSRHVICLDC FHLYCVTRLN DRQFVHDPQL GYSLPCVAGC PNSLIKELHH   420
FRILGEEQYN RYQQYGAEEC VLQMGGVLCP RPGCGAGLLP EPDQRKVTCE GGNGLGCGFA   480
FCRECKEAYH EGECSAVFEA SGTTTQAYRV DERAAEQARW EAASKETIKK TTKPCPRCHV   540
PVEKNGGCMH MKCPQPQCRL EWCWNCGCEW NRVCMGDHWF DV                     582

SEQ ID NO: 83           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 83
MYGRKKRRQR RR                                                       12

SEQ ID NO: 84           moltype = AA  length = 7
FEATURE                 Location/Qualifiers
REGION                  1..7
                        note = Description of Artificial Sequence: Synthetic peptide
VARIANT                 2..3
                        note = Any amino acid
VARIANT                 5
                        note = Any amino acid
source                  1..7
                        mol_type = protein
                        organism = synthetic construct
SEQUENCE: 84
EXXYXQS                                                             7

SEQ ID NO: 85           moltype = AA  length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 85
HHHHHH                                                              6

SEQ ID NO: 86           moltype = DNA  length = 1665
FEATURE                 Location/Qualifiers
misc_feature            1..1665
                        note = Description of Artificial Sequence: Synthetic
                         polynucleotide
source                  1..1665
                        mol_type = other DNA
                        organism = synthetic construct
SEQUENCE: 86
atgtacggcc ggaagaagcg gcggcagcgt cggagaggcg gcatgcagat cttcgtgaaa    60
acattaaccg gcaagaccat caccctggaa gtggaaccta gcgacaccat cgagaacgtg   120
aaggccaaga tccaggacaa ggaaggcatc cctcctgatc agcagcgact gattttcgct   180
ggaaagcagc tggaagatgg cagaaccctg agcgactaca acatccagaa ggagagcaca   240
ctgcacctgg tgctgaggct gcggggcggc atgatcgtgt tcgtagagatt caacagcagc   300
cacggcttcc ccgtcgaggt ggattctgac accagcatct ttcaactgaa ggaagtggtg   360
gcaaagagac agggcgtgcc cgccgatcaa ctgcgggtaa tcttcgccgg aaaagagctg   420
agaaatgact ggacagtgca gaactgcgac ctggatcagc aaagcattgt gcacatcgtg   480
cagcggcctt ggcggaaagg ccaggagatg aacgccaccg gcgagatgac tcctagaaat   540
gctgctggcg gctgcgagcg ggaaccccag agcctgacca gtggacct gtccagctct   600
gtgctaccag gcgacacgt gggcctgggc cgtgatcgtgc acacagattc cagaaaggac   660
agcccacctg ccggcagccc ggccggaagg tccatctaca actccttcta cgtgtactgc   720
aagggccctt gccagagagt gcaacctggc aaactgagag ttcagtgtc tacatgtaga   780
caagccacac tgacactgac ccagggcccc agctgttggg acgacgtgct gatccccaac   840
agaatgagcg gcgagtgcca agcccccac tgccctggca ccagcgccga gttcttcttt   900
aagtgtggag ctcacccacc ctcgacaag gaaaccagcg tggccctgca tctgatcgcc   960
```

```
accaacagca gaaacatcac ctgtatcaca tgcaccgacg tcagaagccc tgtgcttgtg    1020
tttcagtgta atagccggca cgtgatctgc ctggactgct tccacctgta ctgcgtgacc    1080
agactgaacg acagacagtt tgtgcacgac cctcagctgg gctactcgct gccttgtgtg    1140
gccggctgtc ctaactctct gatcaaggaa ctgcatcact tcagaatcct gggcgaggaa    1200
cagtacaacc ggtaccagca gtacggcgcc gaggaatgca tgctgcagat gggcggagtg    1260
ctgtgcccta gacccggatg tggagccgga ctgctgcctg agcccgacca gcggaaagtg    1320
acctgcgagg gaggcaacgg cctcggctgc ggtttcgcct tctgcagaga atgtaaagaa    1380
gcttaccacg aggggggagtg ttctgccgtg ttcgaggcct ctggcacaac cacccaggct    1440
tatagagtgg acgagagagc cgccgagcag gccagatggg aggccgccag caaggagaca    1500
atcaagaaga ccacaaagcc ttgcccacgc tgccacgtgc ctgtggaaaa gaacggcggc    1560
tgtatgcaca tgaagtgccc tcagcctcag tgcagactgg aatggtgctg gaactgcggc    1620
tgcgagtgga atagagtctg catgggcgat cactggttcg acgtt                    1665

SEQ ID NO: 87           moltype = DNA  length = 1461
FEATURE                 Location/Qualifiers
misc_feature            1..1461
                        note = Description of Artificial Sequence: Synthetic
                        polynucleotide
source                  1..1461
                        mol_type = other DNA
                        organism = synthetic construct
SEQUENCE: 87
atgtacggca gaaagaaaag acgccagaga cggcggggcg gcgagcctct gttcgccgaa    60
agaaagatga ttgtgtttgt cagatttaat tcttcacacg gatttcccgt cgaagtggat    120
tcagacacca gtatttttca gcttaaggag gtcgtagcca agcggcaggg cgtgcccgcc    180
gaccaattga gagtgatctt tgctggaaaa gaattgaaga atgattggac tgtccagaac    240
tgcgatttgg atcagcagtc tatcgtgcat atagttcagc gaccatgcg caagggacag    300
gagatgaatg caaccggagg cgacgaccca cggaatgcag ccggagggtg tgagagagag    360
ccccagagtt tgactcgggt cgatctgagc tctagcgtac tcccagggga ttcagtggga    420
ctcgcagtta tcctgcatac tgactccaga aaggactcag ccccgccgg gagtccggca    480
ggaagatcaa tttataatag cttttacgtt tattgtaagg gaccctgtca gagagtacag    540
cccggcaagt tgagggtgca atgtagtacc tgccgccagg ccacgctgac actcacacag    600
ggaccatcct gttgggacga cgtgcttatc cccaacagga tgtccggtga tgtcaatcc    660
cctcactgcc ctgggacaag cgccgaattc ttcttcaaat gtggtgccca ccccacatcc    720
gacaaggaga cttccgtcgc cctgcacctg atcgcaacta acagccggaa tatccacgtgc    780
atcacctgca cggatgtgcg gtccctgtgt ctggtctttc agtgtaattc tcggcacgtg    840
atctgccttg actgcttcca cctgtactgc gttacacgac tgaacgacag gcagttcgtg    900
catgacccctc agcttgggta ctctcttcca tgtgttgccg ggtgtcctaa ctcattgatc    960
aaggagctcc accacttcag gatttgggg gaggagcaat ataaccgata ccagcagtac    1020
ggcgccgagg agtgtgtgct gcagatggga ggagtacttt gtccacgccc gggatgtgga    1080
gcaggcctgc tccagaacc agatcaacgc aaggtgacgt gtgagggagg aaatgggctc    1140
ggctgcgggt tcgcctttg cagggagtgt aaggaggcct atcatgaagg tgaatgctcc    1200
gctgtgttcg aggcctctgg tactaccact caggcctata gtgcctgtac gagagctgct    1260
gagcaagccc gatgggaggc tgcaagcaaa gaaaccatca agaaaactac gaagccatgc    1320
cctcgctgcc atgtgcccgt cgagaagaac ggtggctgca tgcacatgaa gtgtccacag    1380
ccccagtgcc ggttggaatg tgttggaat tgcggatgcg aatggaaccg cgtctgcatg    1440
ggcgatcact ggttcgacgt t                                              1461

SEQ ID NO: 88           moltype = DNA  length = 1467
FEATURE                 Location/Qualifiers
misc_feature            1..1467
                        note = Description of Artificial Sequence: Synthetic
                        polynucleotide
source                  1..1467
                        mol_type = other DNA
                        organism = synthetic construct
SEQUENCE: 88
atgtacggaa gaaaaagcg gagacagaga agaagaggcg ggatgatcgt gttcgtgcgg    60
ttcaacagca gccacggctt tccagtcgag gtggactctg acacctccat cttccagctg    120
aaggaggtgg tggccaagcg gcagggcgtg cctgccgatc agctgagggt gatctttgct    180
gggaaggagc tgcggaatga ctggaccgta cagaactgcg acctggacca gcaatctatc    240
gtgcacatcg tgcagcgacc ttgcgggaag gccaggaga tgaacgctac aggcggcgac    300
gaccctagaa atgccgccgg cggatgtgaa cgggaacctc aatctctgac acgggtggat    360
ctgagctcta gcgtgctccc cggagactct gtgggccctg ccgtgatcct gcacaccgat    420
agcaggaagg acagccccccc cgccggaagt cctgccggca gatccatcta caactctttc    480
tacgtgtact gcaaaggccc ttgccagcgc gtgcagcctg caagctgag agtgcaatgt    540
agcacctgta gacaggccac actgacactg acccagggac ctagctgctg ggatgatgtg    600
ctgattccta acagaatgag cggcgagtgc cagagcccctc actgccccgg cacaagcgcc    660
gaattcttct tcaagtgcgg cgcccaccct accagcgaca aggagacag cgtggcctgc    720
catctaatcg ccactaacag cagaaacatc acctgtatca cctgcaccga cgtcagaagc    780
ccagtgctct gtttcagtg caacagccgg cacgtgatct gcctggattg cttccacctg    840
tactgtgtca ccagactgaa cgatagacag ttcgtgcatg atccacagct gggctacagc    900
ctgccctgcg ttgccggctg tcctaactcc ctgatcaagg aactgcacca cttccggatc    960
ctgggcgagg aacagtacaa ccgtaccagc agtacggcgc ccgaggaatg cgtgctgcag    1020
atgggaggag tgctgtgccc cagacctgga tgcggtgctg gactgctgcc tgagcccgac    1080
caaagaaagg tgacctgcga gggcggcaac ggctgggct gtggcttcgc cttctgcaga    1140
gagtgcaagg aagcctatca cgagggcgaa tgcagcgccg tgtttgaggc ttctggcacc    1200
accacccagg cttatagagt cgacgagcgg gccgctgagc aggccagatg ggaggctgcc    1260
agcaaggaaa ccatcaagaa aacaacaaag ccctgcccta gatgtcacgt gccagttgag    1320
```

```
aagaacggcg gctgcatgca catgaaatgt cctcagcctc agtgcagact ggaatggtgc    1380
tggaattgcg gctgtgaatg gaatcgggtg tgcatgggcg accactggtt cgatgtgctg    1440
gccctgaaac tggcaggcct ggacctg                                        1467
```

MOLECULES FOR ORGANELLE-SPECIFIC PROTEIN DELIVERY

RELATED APPLICATIONS

This application is a continuation of U.S. application Ser. No. 17/214,757, filed on Mar. 26, 2021, which claims priority to U.S. Provisional Patent Application No. 63/000,138, filed on Mar. 26, 2020. The entire contents of each of the foregoing applications are hereby incorporated herein by reference.

REFERENCE TO ELECTRONIC SEQUENCE LISTING

The application contains a Sequence Listing which has been submitted electronically in .XML format. Said .XML copy, created on Dec. 18, 2023, is named "130197-00403.xml" and is 129,919 bytes in size. The sequence listing contained in this .XML file is part of the specification and is hereby incorporated by reference herein in its entirety.

BACKGROUND

Cationic cell penetrating peptides (CPPs) have emerged as a promising means of delivering therapeutic proteins into cells. However, one potential drawback of appending a CPP to a therapeutic protein is that the CPP may interfere with the therapeutic protein's proper subcellular localization or function. For example, certain cell penetrating peptides, such as HIV-TAT, have been shown to direct delivery of therapeutic proteins into the nucleus, which may not be the desired subcellular destination for a therapeutic protein of interest.

Delivery of therapeutic proteins into the mitochondria of mammalian cells has been attempted, for example, with the TAT-FXN fusion protein. TAT-FXN fusion protein contains TAT and Frataxin (FXN), which is a mitochondrial protein associated with the inherited condition Friedreich's Ataxia (FRDA). FRDA patients suffer from progressive damage to the nervous system that results in muscle weakness and eventual loss of motor control. FRDA is caused by transcriptional repression of the FRDA gene, resulting in the lack or minute amounts of hFXN protein in FRDA patients.

The improvement of effective technology for delivering therapeutic proteins into cells, and while maintaining the therapeutic protein's proper subcellular localization or function, including in the context of organelle-specific therapeutic protein delivery, continues to be an area of great demand in medicine.

SUMMARY

The present disclosure provides fusion proteins that are capable of being efficiently delivered to cells, e.g., in greater levels than previously achieved. The present disclosure further provides fusion proteins that are capable of efficiently delivering a therapeutic protein of interest to cells and achieving and maintaining the proper subcellular localization and/or function of the therapeutic protein of interest. For example, the present disclosure provides fusion proteins that are capable of being efficiently delivered to non-nuclear organelles. An exemplary fusion protein provided by the present disclosure comprises, in addition to a protein of interest to be delivered to a cell, a cell penetrating peptide (CPP); and/or a target enhancing sequence (TES). In the fusion protein of the present disclosure, the CPP is capable of interference with delivery of the protein of interest to the protein's proper subcellular localization and/or with its function, and the TES prevents this interference by CPP. Another exemplary fusion protein provided by the present disclosure comprises, in addition to a protein of interest to be delivered to a non-nuclear organelle, an organelle targeting sequence (OTS); a cell penetrating peptide (CPP); and/or a target enhancing sequence (TES). In said fusion protein of the present disclosure, the CPP is capable of interference with delivery of the protein of interest to the non-nuclear organelle, and the TES prevents this interference by CPP.

The present disclosure also is based, at least on part, on the surprising discovery that including certain amino acid sequences (i.e., TES) in a fusion protein that also comprises a protein of interest and a CPP, facilitated effective delivery of the protein of interest to the cell, e.g., resulted in increased levels of the protein of interest in cells treated with the fusion protein, and allowed for proper subcellular localization and/or function of the protein of interest. In particular, the present inventors have discovered that cells treated with fusion proteins comprising a protein of interest, CPP and TES contained significantly higher amounts of the protein of interest than cells treated with a fusion protein comprising a protein of interest and CPP, but lacking TES. Thus, the present inventors have surprisingly discovered that introducing TES into a fusion protein comprising CPP and a protein of interest can significantly increase the amount of protein of interest in a cell that has been contacted with the fusion protein. The present inventors also surprisingly discovered that fusion proteins comprising a protein of interest, CPP and TES were correctly processed by the cellular machinery, achieved proper cellular localization, e.g., were targeted to a non-nuclear organelle, and possessed the desired activity of the protein of interest when delivered to cells.

In some exemplary fusion proteins provided by the present disclosure, the TES comprises an amino acid sequence cleavable by an endogenous intracellular protease. In some embodiments, this TES is located immediately adjacent to the CPP, which, in turn, is located at the N-terminal end of the fusion protein. Upon entry of the fusion protein into the cell cytoplasm, the TES is cleaved by an intracellular nuclease. Without wishing to be bound by a specific theory, it is believed that cleavage of the TES facilitates removal of the CPP from the fusion protein and prevents the CPP from facilitating diffusion of the protein of interest across the plasma membrane and out of the cell. This allows the protein of interest to accumulate in the cell. The present disclosure is further based, at least on part, on the surprising discovery that including certain amino acid sequences (i.e., TES) in a fusion protein that also comprises a protein of interest, a CPP and an OTS, facilitated effective delivery of the protein of interest to a non-nuclear organelle, such as mitochondria. In particular, the present inventors have discovered that fusion proteins comprising a protein of interest, CPP and an organelle targeting sequence (OTS), e.g. a mitochondrial targeting sequence (MTS), but not TES, localized to the cell nucleus instead of the mitochondria upon entry into the cell, due to the interference of the CPP with mitochondrial delivery of the protein of interest. The present inventors further discovered that including certain amino acid sequences, such as TES, in fusion proteins also comprising a protein of interest, a CPP and an OTS, e.g., an MTS, facilitated delivery of the protein of interest to the mitochondria upon entry of the fusion protein into the cell.

In exemplary fusion proteins provided by the present disclosure, the TES comprises an amino acid sequence cleavable by an endogenous intracellular protease. In some embodiments, this TES is located immediately adjacent to the CPP, which, in turn, is located at the N-terminal end of the fusion protein. Upon entry of the fusion protein into the cell cytoplasm, the TES is cleaved by an intracellular nuclease. Cleavage of the TES facilitates removal of the CPP from the fusion protein and prevents interference of the CPP with delivery of the fusion protein to the mitochondria. In other exemplary fusion proteins of the present disclosure, the TES comprises a nuclear export signal peptide (NES), which prevents CPP-facilitated delivery of the fusion protein to the nucleus and, instead, facilitates delivery of the fusion protein to non-nuclear organelles, such as mitochondria.

In other exemplary fusion proteins of the present disclosure, the TES comprises a nuclear export signal peptide (NES), which prevents accumulation of the protein of interest in the nucleus.

In some aspects, the present disclosure provides a fusion protein, comprising: a protein of interest to be delivered to a cell; a cell penetrating peptide (CPP); and a target enhancing sequence (TES).

In some embodiments, the CPP is located at the N-terminus of the fusion protein and wherein the TES is fused at the C-terminus of the CPP. In some embodiments, the fusion proteins comprises, or consists of, starting at the N-terminus: CPP; TES; and a protein of interest.

In some embodiments, the CPP is located at the C-terminus of the fusion protein and wherein the TES is fused at the N-terminus of the CPP.

In some embodiments, the fusion protein comprises, or consists of, starting at the C-terminus: a protein of interest; TES; and CPP.

In some embodiments, the protein of interest lacks an OTS.

In other embodiments, the fusion protein further comprises an organelle targeting sequence (OTS) exogenous to the protein of interest.

In some embodiments, the protein of interest comprises an OTS.

In some embodiments, the OTS is heterologous to the protein of interest. In some embodiments, the OTS is endogenous to the protein of interest.

In some embodiments, the protein of interest is selected from the group consisting of Frataxin (FXN), Tafazin, Pyruvate Dehydrogenase (PDH), SLIRP, LRPPC, PARK2 protein, PARK6 protein, PARK7 protein, Phospholipase A2, Group VI and a variant or derivative thereof. In some embodiments, the protein of interest comprises Frataxin (FXN) or PARK2 protein (PARKIN), or a variant or derivative thereof.

In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In some embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1 and NES2, or a variant or derivative thereof.

In some embodiments, the TES is a protease sensitive peptide. In some embodiments, the protease sensitive peptide comprises a ubiquitin-like modifier. In some embodiments, the protease sensitive peptide comprises a sequence having at least 85% sequence identity to any one of SEQ ID NOs. 18-31.

In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the fusion protein comprises an amino acid sequence having at least 85%, 90%, or 95% sequence identity to any of SEQ ID NOs. 55-61, 69-71, and 81.

In some aspects, the present disclosure provides a fusion protein, comprising: a protein of interest to be delivered to a non-nuclear organelle; an organelle targeting sequence (OTS); a cell penetrating peptide (CPP); and a target enhancing sequence (TES); wherein the CPP is capable of interference with delivery of the protein of interest to the non-nuclear organelle; and wherein the TES prevents said interference by the CPP.

In some embodiments, the CPP is located at the N-terminus of the fusion protein and wherein the TES is fused at the C-terminus of the CPP.

In some embodiments, the fusion protein comprises, or consists of, starting at the N-terminus: CPP; TES; OTS; and a protein of interest.

In some embodiments, the CPP is located at the C-terminus of the fusion protein and wherein the TES is fused at the N-terminus of the CPP. In some embodiments, the non-nuclear organelle is selected from the group consisting of mitochondria, cytosol, lysosome, endoplasmic reticulum (ER), peroxisome and Golgi apparatus. In some embodiments, the protein of interest in its naturally occurring form is localized to mitochondria, cytosol, lysosome, endoplasmic reticulum (ER), peroxisome or Golgi apparatus.

In some embodiments, the protein of interest is selected from the group consisting of Frataxin (FXN), Tafazin, Pyruvate Dehydrogenase (PDH), SLIRP, LRPPC, PARK2 protein, PARK6 protein, PARK7 protein, Phospholipase A2, Group VI and a variant or derivative thereof. In some embodiments, the protein of interest is Frataxin (FXN) or a variant or derivative thereof. In some embodiments, the protein of interest is Pyruvate Dehydrogenase (PDH) or a variant or derivative thereof.

In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In some embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1, NES2 and a variant or derivative thereof.

In some embodiments, the TES is a protease sensitive peptide. In some embodiments, the protease sensitive peptide comprises a ubiquitin-like modifier. In some embodiments, the protease sensitive peptide comprises a sequence having at least 85% sequence identity to any one of SEQ ID NOs. 18-31. In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the fusion protein of the present disclosure further comprises a secretion signal (SS).

In some embodiments, the fusion protein of the present disclosure further comprises an extracellular proteolytic site (EPS).

In some embodiments, the fusion protein delivers the protein of interest to a non-nuclear organelle. In some embodiments, the fusion protein delivers the protein of interest to mitochondria.

In some embodiments, the fusion protein comprises an amino acid sequence having at least 85%, 90% or 95% sequence identity to any of SEQ ID NOs. 55-61, 69-71 and 81.

In some aspects, the present disclosure also provides nucleic acids encoding the fusion proteins of the present disclosure.

In some aspects, the present disclosure also provides an expression vector for introducing a fusion protein into a cell comprising the nucleic acid of the disclosure. In some embodiments, the expression vector is selected from the group consisting of a retroviral vector, a DNA vector, a plasmid, an RNA vector, an adenoviral vector, an adenovirus associated vector, a lentiviral vector, a phagemid, a baculovirus and a combination thereof.

In some aspects, the present disclosure provides a conjugate for intracellular delivery of proteins to non-nuclear organelles comprising the fusion protein of the disclosure and a moiety linked to said fusion protein, wherein said moiety is selected from a group consisting of a radioactive label, a fluorescent label, a small molecule, and a polymeric molecule. In some embodiments, the polymeric molecule is polyethylene glycol (PEG).

In some aspects, the present disclosure provides a cell comprising the fusion protein of the disclosure, the nucleic acid the disclosure, the expression vector of the disclosure, the conjugate of the disclosure, or a combination thereof. In some embodiments, the cell is a stem cell or an iPS cell. In some embodiments, the cell is selected from the group consisting of a muscle progenitor cell, a neuron progenitor cell, a bone marrow stem cell, a bacterial cell line, or an yeast cell line.

In some aspects, the present disclosure also provides a pharmaceutical composition comprising the fusion protein of the disclosure, a conjugate of the disclosure, or a combination thereof and a pharmaceutically acceptable diluent, carrier, additive or excipient.

In some aspects, the present disclosure provides a method of delivery of a protein of interest to a cell, said method comprising contacting the cell with a fusion protein of the disclosure, the nucleic acid of the disclosure, the vector of the disclosure or the conjugate of the disclosure.

In some aspects, the present disclosure also provides a method of intracellular delivery of a protein of interest to a non-nuclear organelle in a cell, the method comprising contacting said cell with a fusion protein of the disclosure, the nucleic acid of the disclosure, the vector of any one of the disclosure or the conjugate of the disclosure. In some embodiments, the non-nuclear organelle is mitochondria.

In some aspects, the present disclosure also provides a therapeutic compound for treating a non-nuclear organelle associated disorder, the compound comprising the fusion protein the disclosure, the nucleic acid of the disclosure, the vector of the disclosure or the conjugate of the disclosure. In some embodiments, the non-nuclear organelle associated disorder is selected from the group consisting of Friedreich's ataxia (FDRA), Barth Syndrome, Parkinson's Disease, Wilson's Disease, Leigh Syndrome, Fibrosis, and PLA2G6-associated neurodegeneration (PLAN). In some embodiments, the non-nuclear organelle associated disorder is FDRA. In some embodiments, the non-nuclear organelle associated disorder is Parkinson's Disease.

In some aspects, the present disclosure also provides a method for treating a non-nuclear organelle associated disorder, the method comprising administering to a subject in need thereof the fusion protein of the disclosure, the nucleic acid of the disclosure, the vector of the disclosure, the conjugate of the disclosure or the pharmaceutical composition of the disclosure, such that the non-nuclear organelle associated disorder is treated.

In some embodiments, the non-nuclear organelle associated disorder is selected from the group consisting of Friedreich's ataxia (FDRA), Barth Syndrome, Parkinson's Disease, Wilson's Disease, Leigh Syndrome and Fibrosis. In some embodiments, the non-nuclear organelle associated disorder is FDRA. In some embodiments, the non-nuclear organelle associated disorder is Parkinson's Disease.

In some embodiments, the subject is a human.

In some aspects, the present disclosure also provides a method for increasing an amount of a protein of interest delivered to a cell, the method comprising: modifying a sequence of a fusion protein comprising the protein of interest and a cell penetrating peptide (CPP) by introducing into the fusion protein a target enhancing sequence (TES), thereby producing a modified fusion protein; and contacting a cell with the modified fusion protein, thereby increasing the amount of the protein of interest delivered to the cell relative to the amount of the protein of interest delivered to the cell by the fusion protein lacking the TES.

In some embodiments, the modified fusion protein, the CPP is located at the N-terminus of the fusion protein and wherein the TES is fused at the C-terminus of the CPP.

In some embodiments, the modified fusion protein comprises, starting at the N-terminus: CPP; TES; and a protein of interest.

In some embodiments, the modified fusion protein comprises, starting at the N-terminus: CPP; TES; OTS; and a protein of interest.

In some embodiments, the modified fusion protein the CPP is located at the C-terminus of the fusion protein and wherein the TES is fused at the N-terminus of the CPP. In some embodiments, the amount of the protein of interest delivered to an organelle targeted by the OTS is increased relative to the amount of the protein of interest delivered to the organelle by the fusion protein lacking the TES.

In some embodiments, the protein of interest is selected from the group consisting of Frataxin (FXN), Tafazin, Pyruvate Dehydrogenase (PDH), SLIRP, LRPPC, PARK2 protein, PARK6 protein, PARK7 protein, and Phospholipase A2, Group VI, or a variant or derivative thereof. In some embodiments, the protein of interest is Frataxin (FXN) or a variant or derivative thereof. In some embodiments, the protein of interest is PARK2 protein or a variant or derivative thereof.

In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In some embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1, NES2 and a variant or derivative thereof.

In some embodiments, the TES is a protease sensitive peptide. In some embodiments, the protease sensitive peptide comprises a ubiquitin-like modifier. In some embodiments, the protease sensitive peptide comprises a sequence having at least 85% sequence identity to any one of SEQ ID NOs. 18-31. In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the modified fusion protein comprises an amino acid sequence having at least 85% sequence identity to any of SEQ ID NOs. 55-61, 69-71 and 81.

In one aspect, the present disclosure provides a fusion protein, comprising: a protein of interest to be delivered to a non-nuclear organelle; an organelle targeting sequence (OTS); a cell penetrating peptide (CPP); and a target enhancing sequence (TES); wherein the CPP is capable of interference with delivery of the protein of interest to the non-nuclear organelle; and wherein the TES prevents said interference by the CPP.

In some embodiments, the CPP is located at the N-terminus of the fusion protein and the TES is fused at the C-terminus of the CPP. In some embodiments, the present disclosure provides a fusion protein that comprises, starting at the N-terminus: CPP; TES; OTS; and a protein of interest.

In some embodiments, the CPP is located at the C-terminus of the fusion protein and the TES is fused at the N-terminus of the CPP.

In some embodiments, the non-nuclear organelle is selected from the group consisting of mitochondria, cytosol, lysosome, endoplasmic reticulum (ER), peroxisome and Golgi apparatus.

In some embodiments, the protein of interest in its naturally occurring form is localized to mitochondria, cytosol, lysosome, endoplasmic reticulum (ER), peroxisome or Golgi apparatus.

In some embodiments, the protein of interest is selected from the group consisting of Frataxin (FXN), Tafazin, Pyruvate Dehydrogenase (PDH), LRPPC, PARK2 protein, PARK6 protein, PARK7 protein, an A2 phospholipase Group VI, a transcription factor, and a variant or derivative thereof. In one embodiment, the protein of interest is Frataxin (FXN) or a variant or derivative thereof. In one embodiment, the protein of interest is pyruvate dehydrogenase (PDH) or a variant or derivative thereof.

In some embodiments, the CPP comprises a peptide selected from the group of CPPs listed in the Database of Cell-Penetrating Peptides CPPsite 2.0. In further embodiments, the CPP comprises a peptide selected from the group consisting of HIV-TAT, galanin, mastoparan, transportan, penetratin, polyarginine, VP22, and a variant or derivative thereof. In some embodiments, the CPP comprises HIV-TAT or a variant or derivative thereof.

In some embodiments, the TES is a nuclear export signal peptide. In further embodiments, the nuclear export signal peptide comprises a sequence having at least 85% sequence identity to any one of SEQ ID NOs. 36-43. In some embodiments, the nuclear export signal peptide comprises a peptide selected from the group consisting of NES1, NES2, NES3, NES4, NES5, NES6, NES7, NES8, and a variant or derivative thereof. In some embodiments, the nuclear export signal peptide comprises a peptide selected from the group consisting of NES1, NES2 and a variant or derivative thereof.

In some embodiments, the TES is a protease sensitive peptide. In some embodiments, the protease sensitive peptide comprises a ubiquitin-like modifier. In some embodiments, the ubiquitin-like modifier comprises a sequence having at least 85% sequence identity to any one of SEQ ID NOs. 18-31.

In some embodiments, the protease sensitive peptide comprises a peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some embodiments, the fusion protein provided by the present disclosure comprises a secretion signal (SS). In some embodiments, the fusion protein comprises an extracellular proteolytic site (EPS).

In some embodiments, the fusion protein delivers the protein of interest to a non-nuclear organelle. In a specific embodiment, the fusion protein delivers the protein of interest to mitochondria.

In some embodiments, the fusion protein comprises a sequence having at least 85% sequence identity to any of SEQ ID NOs. 55-61.

In another aspect, the present disclosure provides a nucleic acid encoding the fusion protein of the disclosure.

In a related aspect, the present disclosure provides an expression vector comprising a nucleic acid of the disclosure for introducing a fusion protein into a cell.

In some embodiments, the expression vector is selected from the group consisting of a retroviral vector, a DNA vector, a plasmid, an RNA vector, an adenoviral vector, an adenovirus associated vector, a lentiviral vector, a phagemid, a baculovirus and a combination thereof.

In another aspect, the present disclosure provides a protein conjugate for intracellular delivery of proteins to non-nuclear organelles that comprises a fusion protein of the disclosure and a moiety linked to the fusion protein, wherein the moiety is selected from the group consisting of a radioactive label, a fluorescent label, a small molecule, and a polymeric molecule. In one embodiment, the polymeric molecule is polyethylene glycol (PEG).

In another aspect, the present disclosure provides a cell comprising a fusion protein, a nucleic acid, an expression vector or a conjugate of the disclosure, or a combination thereof. The cell may be a transformed cell, e.g., a cell which has been transformed with a fusion protein, a nucleic acid, an expression vector or a conjugate of the disclosure, or a combination thereof. In some aspects, the cell is stem cell or an iPS cell. In some aspects, a cell may be selected from the group consisting of a muscle progenitor cell, a neuron progenitor cell, a bone marrow stem cell, a bacterial cell, or a yeast cell.

In another aspect, the present disclosure provides a pharmaceutical composition comprising a fusion protein or a protein conjugate of the disclosure, or a combination thereof, and a pharmaceutically acceptable diluent, carrier, additive or excipient.

In another aspect, the present disclosure provides a method of intracellular delivery of a protein of interest to a non-nuclear organelle in a cell, comprising contacting the cell with a fusion protein, a nucleic acid, a vector or a protein conjugate of the disclosure. In one aspect, the non-nuclear organelle is mitochondria.

In another aspect, the present disclosure provides a therapeutic compound for treating a non-nuclear organelle associated disorder, which comprises a fusion protein, a nucleic acid, a vector or a protein conjugate of the disclosure. In some, the non-nuclear organelle associated disorder is selected from the group consisting of Friedreich's ataxia (FDRA), Barth Syndrome, Parkinson's Disease, Wilson's Disease, Leigh Syndrome, Fibrosis and PLA2G6-associated neurodegeneration (PLAN). In one embodiment, PLAN may comprise a disorder selected from the group consisting of infantile neuroaxonal dystrophy (INAD), atypical neuroaxonal dystrophy (ANAD), Parkinsonian Syndrome which contains adult onset dystonia parkinsonism (DP) and autosomal recessive early-onset parkinsonism (AREP). In one aspect, the non-nuclear organelle associated disorder is FDRA.

In a related aspect, the present disclosure provides a method for treating a non-nuclear organelle associated disorder, comprising administering to a subject in need thereof a fusion protein, a nucleic acid, a vector, a protein conjugate, or a pharmaceutical composition of the disclosure, such that the non-nuclear organelle associated disorder is treated. In some embodiments, the non-nuclear organelle associated disorder is selected from the group consisting of Friedreich's ataxia (FDRA), Barth Syndrome, Parkinson's Disease, Wilson's Disease, Leigh Syndrome and Fibrosis. In one specific embodiment, the non-nuclear organelle associated disorder is FDRA.

In some embodiments, the subject is a human.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

FIG. 9, Panel B is a high magnification image of cells treated with TAT-GG-Ubiquitin-hFXN. This image shows the details of hFXN stain and its localization to mitochondria.

FIG. 9, Panel C is a bar graph showing the ratios of mean hFXN stain signal to the mean nuclear stain signal for cells treated with various concentrations of TAT-GG-hFXN, TAT-GG-EPLFAERK-hFXN and TAT-GG-Ubiquitin-hFXN FIG. 9, Panel D is a picture of a nitrocellulose membrane following transfer from an SDS-PAGE gel loaded with samples of TAT-GG-hFXN, TAT-GG-EPLFAERK-hFXN, TAT-GG-Ubiquitin-hFXN used for transduction experiments and stained for total protein. The picture demonstrates lack of fusion protein degradation and that the same amount of each fusion protein was used in transduction experiments.

FIG. 10, Panel B presents the ratio of the mean anti-FXN stain signal to the mean anti-mitochondrial stain signal graphed as a function of hFXN fusion protein concentration in Schwann cells treated with TAT-GG-hFXN, TAT-GG-EPLFAERK-hFXN and TAT-GG-Ubiquitin-hFXN.

FIG. 10, Panel C presents the ratio of the mean anti-FXN stain signal to the mean anti-mitochondrial stain signal graphed as a function of hFXN fusion protein concentration in H9C2 cells treated with TAT-GG-hFXN, TAT-GG-EPLFAERK-hFXN and TAT-GG-Ubiquitin-hFXN.

FIG. 10, Panel D presents the ratio of the mean anti-FXN stain signal to the mean anti-mitochondrial stain signal graphed as a function of hFXN fusion protein concentration in Schwann cells treated with TAT-GG-hFXN, TAT-GG-EPLFAERK-hFXN, TAT-GG-Ubiquitin-hFXN and TAT-GG-hFXN-NES1.

FIG. 12, Panel B is a series of photographs of LRPPRC KD and Scr-5 control cells treated with the highest tested concentration of each hFXN fusion protein or vehicle.

FIG. 12, Panel C is a graph showing the amount of CYR61 in the media of LRPPRC KD cells treated with hFXN fusion proteins.

FIG. 12, Panel D is a graph showing the amount of lactate in the media of LRPPRC KD cells treated with hFXN fusion proteins.

DETAILED DESCRIPTION

Figure 1:
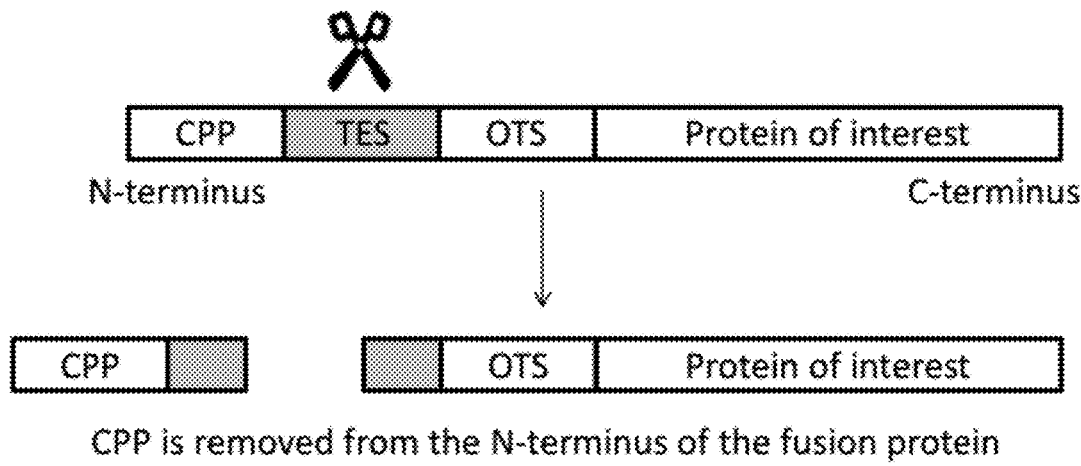
FIG. 1 is a schematic illustrating certain fusion proteins of the disclosure comprising a target enhancing sequence (TES) with a protease cleavage site.
Figure 1:
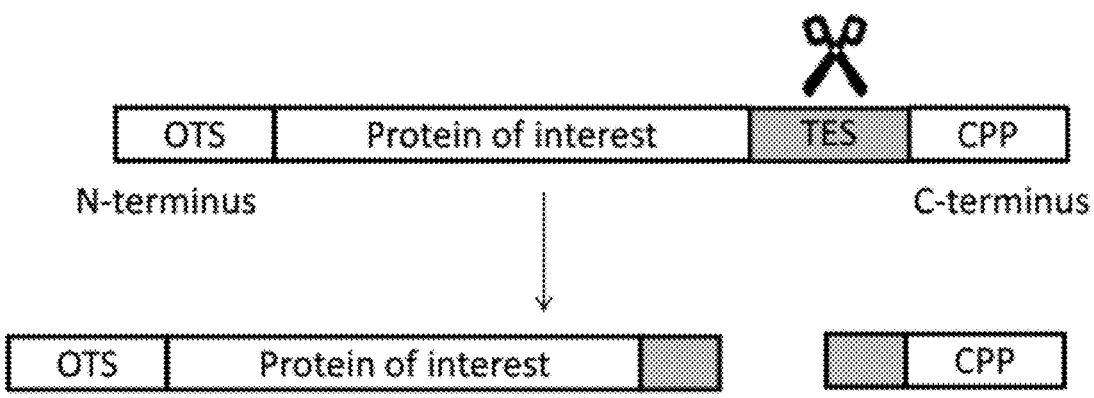

An aspect of the disclosure relates to providing a fusion protein comprising a protein of interest to be delivered to a cell. In some embodiments, the fusion protein comprises a protein of interest to be delivered to a particular organelle, e.g., a non-nuclear organelle, such as the mitochondria. The fusion protein also comprises at least one cell penetrating peptide (CPP), at least one target enhancing sequence (TES) and, optionally, at least one organelle-targeting signal (OTS).

In certain aspects of the present disclosure, the CPP is capable of interfering with delivery of the protein of interest to an organelle, such as a non-nuclear organelle. For example, as demonstrated by certain experimental data included in the present disclosure, a CPP, e.g., HIV-TAT, may interfere with delivery of the protein of interest, e.g., FXN, to the mitochondria. Specifically, HIV-TAT facilitates delivery of FXN to the nucleus instead of the mitochondria. Accordingly, a fusion protein of the present disclosure comprises a TES which prevents or attenuates the interference of CPP with the delivery of the protein of interest to an appropriate cellular (e.g., non-nuclear) organelle.

For example, in some embodiments, a CPP may be located at the N-terminus of the fusion protein and the TES may be fused at the C-terminus of the CPP. Alternatively, the CPP may be located at the C-terminus of the fusion protein and the TES may be fused at the N-terminus of the CPP. The TES may comprise an intracellular protease recognition sequence which facilitates cleavage of the fusion protein at the TES upon entry to the cell, thereby removing CPP from the remainder of the fusion protein and preventing it from directing the fusion protein to the nucleus.

Alternatively, the TES may comprise a nuclear export signal, e.g., a signal that facilitates export of the fusion protein from the nucleus after it has been delivered to the nucleus mediated by the CPP.

Another aspect of the disclosure also relates to providing a fusion protein comprising a protein of interest to be delivered to cell. The fusion protein comprises at least one cell penetrating peptide (CPP), at least one target enhancing sequence (TES) and a protein of interest.

In some embodiments of the present disclosure, the CPP is capable of interfering with delivery of a protein of interest to a cell. For example, as demonstrated by certain experimental data included in the present disclosure, cells treated with fusion proteins comprising a protein of interest, CPP and TES contained significantly higher amounts of the protein of interest than cells treated with a fusion protein comprising a protein of interest and CPP, but not TES. Thus, it was unexpectedly discovered that introducing TES into a fusion protein comprising CPP and a protein of interest can significantly increase the amount of protein of interest delivered to a cell.

Without wishing to be bound by a specific theory, it is believed that cleavage of TES by endogenous proteases in a cell facilitates removal of the CPP from the fusion protein and prevents the CPP from facilitating diffusion of the protein of interest across the plasma membrane and out of the cell. This allows the protein of interest to accumulate in the cell. Removal of the CPP from the fusion protein also prevents the CPP from interfering with proper subcellular localization of the protein of interest. Accordingly, a fusion protein of the present disclosure comprises a TES which prevents or attenuates the interference of CPP with the delivery of the protein of interest to a cell. In some embodiments, a fusion protein of the present disclosure comprises a TES which prevents or attenuates the interference of CPP with the proper subcellular localization of the protein of interest in the cell.

In some embodiments, a CPP may be located at the N-terminus of the fusion protein and the TES may be fused at the C-terminus of the CPP. Alternatively, the CPP may be located at the C-terminus of the fusion protein and the TES may be fused at the N-terminus of the CPP. The TES may comprise an intracellular protease recognition sequence which facilitates cleavage of the fusion protein at the TES upon entry to the cell, thereby removing CPP from the remainder of the fusion protein and preventing it from directing the fusion protein out of the cell.

Alternatively, the TES may comprise a nuclear export signal peptide (NES). Without wishing to be bound by a specific theory, it is believed that CPP facilitates transport of the fusion protein into the nucleus, and NES, when present in the fusion protein, prevents accumulation of the fusion protein in the nucleus. By preventing accumulation of the fusion protein in the nucleus, NES facilitates proper subcellular localization of the protein of interest comprised in the fusion protein outside of the nucleus, e.g., in the mitochondria.

In some embodiments, removal of CPP through cleavage of the TES by an endogenous protease facilitates proper subcellular localization of the protein of interest. In some cases, a protein of interest, e.g., NFkappa b, androgen receptor, estrogen receptor or aconitase, may typically be localized in more than one cellular compartment, such as nucleus and mitochondria. Removal of CPP through cleavage of TES by an endogenous protease prevents interference of the CPP with proper subcellular localization of the protein of interest in response to endogenous stimuli.

Protein of Interest

The fusion protein provided by the present disclosure comprises a protein of interest to be delivered to a cell. In some embodiments, the fusion protein provided by the present disclosure comprises a protein of interest to be delivered to a particular organelle within the cell, e.g., a non-nuclear organelle. The protein of interest comprised in the fusion protein of the disclosure may be associated with a non-nuclear organelle, e.g., the protein of interest may be an intra-cellular, non-nuclear organelle-specific protein. For example, the protein of interest may localize to a non-nuclear organelle and/or may be capable of, or facilitate, an intracellular function that is effected in a non-nuclear organelle. Exemplary non-nuclear organelles include cytosol, mitochondria, lysosomes, endoplasmic reticulum, Golgi apparatus and peroxisomes. In some embodiments, the protein of interest comprised in the fusion protein of the disclosure may alternatively be associated with the nucleus, and in some embodiments, associated with the nucleus and one or more non-nuclear organelles, e.g., the protein of interest may be an intra-cellular protein that is localized both in the nucleus and in other, non-nuclear organelles (e.g., the cytosol, mitochondria, lysosomes, endoplasmic reticulum, Golgi apparatus and peroxisomes).

The protein of interest may be associated with a pathological condition in a subject. Such pathological condition may result, for example, from a deficiency in the protein of interest in the subject, e.g., when the protein of interest may be mutated in a way to reduce or eliminate the natural activity of the protein of interest, or when the protein of interest may be absent altogether.

In some aspects of the disclosure, the protein of interest may be associated with mitochondria. Exemplary proteins of interest that are associated with mitochondria may include, e.g., frataxin (FXN), tafazzin, pyruvate dehydrogenase beta2 (PDHB), leucine-rich PPR motif-containing protein (LRP-PRC protein), SLIRP, Parkin RBR E3 ubiquitin protein ligase (PARK2 protein or PARKIN), PTEN-induced kinase 1 (PINK1 or PARK6 protein), Protein deglycase DJ-1 (PARK7 protein) and A2 phospholipase Group VI.

In some embodiments, the protein of interest comprises an OTS. In some embodiments, the OTS is endogenous to the protein of interest. In some embodiments, the OTS is exogenous to the protein of interest.

In some embodiments, the protein of interest lacks an OTS. In some embodiments, the protein of interest lacks an OTS in its native form, i.e., it does not contain an OTS in nature. In some embodiments, the protein of interest lacking an OTS is a mature form of a protein wherein the endogenous OTS has been removed.

In one specific embodiment, the protein of interest that is associated with mitochondria may be frataxin (FXN), e.g., human FXN, which is associated with a pathological condition Friedreich's Ataxia (FRDA). FRDA is a genetic, progressive neurodegenerative disorder caused by a mutation in a gene encoding FXN. The FXN is an essential and phylogenetically conserved protein that is found in cells throughout the body, with the highest levels in the heart, spinal cord, liver, pancreas, and skeletal muscle. FXN is encoded in the nucleus, expressed in the cytoplasm and imported into the mitochondria where it is processed to the mature form. In humans, the 210-amino acid full-length hFXN (hFXN$_{1-210}$, 23.1 kDa) contains a typical mitochondrial targeting sequence (MTS) at the amino terminus that is processed in a 2-step cleavage by the mitochondrial matrix processing peptidase (MPP) as it is imported into the mitochondrial matrix. The resulting protein is a 130-amino acid, 14.2 kDa mature hFXN protein (hFXN$_{81-210}$). Sequences of the full-length hFXN and mature hFXN are shown in Table 1 below.

TABLE 1

Sequences of the full-length hFXN and mature hFXN.

| SEQ ID NO. | Protein | Amino Acid Sequence |
|---|---|---|
| 1 | Full-length hFXN hFXN$_{1-210}$ | MWTLGRRAVAGLLASPSPA QAQTLTRVPRPAELAPLCG RRGLRTDIDATCTPRRASS NQRGLNQIWNVKKQSVYLM NLRKSGTLGHPGSLDETTY ERLAEETLDSLAEFFEDLA DKPYTFEDYDVSFGSGVLT VKLGGDLGTYVINKQTPNK QIWLSSPSSGPKRYDWTGK NWVYSHDGVSLHELLAAEL TKALKTKLDLSSLAYSGKD A |
| 2 | Mature hFXN hFXN$_{81-210}$ | SGTLGHPGSLDETTYERLA EETLDSLAEPEEDLADKPY TFEDYDVSFGSGVLTVKLG GDLGTYVINKQTPNKQIWL SSPSSGPKRYDWTGKNWVY SHDGVSLHELLAAELTKAL KTKLDLSSLAYSGKDA |

Accordingly, in some aspects, the fusion protein provided by the present disclosure may comprise the full length hFXN (hFXN$_{1-210}$), i.e., including MTS as an organelle targeting sequence (OTS). In some aspects, the fusion protein may comprise an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of the full length hFXN, e.g., SEQ ID NO: 1 as listed in Table 1.

In some aspects, the fusion protein provided by the present disclosure may comprise the mature hFXN (hFXN$_{81-210}$). In some aspects, the fusion protein may comprise an amino acid sequence having at least 85%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of the mature hFXN, e.g., SEQ ID NO: 2 as listed in Table 1.

In other aspects, exemplary proteins of interest which may be comprised in the fusion protein of the present disclosure include tafazzin, pyruvate dehydrogenase beta2 (PDHB), leucine-rich PPR motif-containing protein (LRP- PRC protein), SLIRP, Parkin RBR E3 ubiquitin protein ligase (PARK2 protein or PARKIN), PTEN-induced kinase 1 (PINK1 or PARK6 protein), Protein deglycase DJ-1 (PARK7 protein) and A2 phospholipase Group VI.

Table 2 below lists exemplary proteins of interest, corresponding human sequences, and associated pathological conditions that may be treated with a fusion protein of the present disclosure comprising said protein of interest.

TABLE 2

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| 3 | Tafazzin | MPLHVKWPFPAVPPLTWTLASSVVMGLVGTY SCFWTKYMNHLTVHNREVLYELIEKRGPATP LITVSNHQSCMDDPHLWGILKLRHIWNLKLM RWTPAAADICFTKELHSHFFSLGKCVPVCRG AEFFQAENEGKGVLDTGRHMPGAGKRREKGD GVYQKGMDFILEKLNHGDWVHIFPEGKVNMS SEFLRFKWGIGRLIAECHLNPIILPLWHVGM NDVLPNSPPYFPRFGQKITVLIGKPFSALPV LERLRAENKSAVEMRKALTDFIQEEFQHLKT QAEQLHNHLQPGR | Barth Syndrome and Familial Isolated Dilated Cardiomyopathy |
| 4 | Pyruvate Dehydrogenase Beta2 (PDHB) | MAAVSGLVRRPLREVSGLLKRRFHWTAPAAL QVTVRDAINQGMDEELERDEKVFLLGEEVAQ YDGAYKVSRGLWKKYGDKRIIDTPISEMGFA GIAVGAAMAGLRPICEFMTFNFSMQAIDQVI NSAAKTYYMSGGLQPVPIVFRGPNGASAGVA AQHSQCFAAWYGHCPGLKVVSPWNSEDAKGL IKSAIRDNNPVVVLENELMYGVPFEFPPEAQ SKDFLIPIGKAKIERQGTHITVVSHSRPVGH CLEAAAVLSKEGVECEVINMKTIRPMDMETI EASVMKTNHLVTVEGGWPQFGVGAEICARIM EGPAFNFLDAPAVRVTGADVPMPYAKILEDN SIPQVKDIIFAIKKTLNI | Pyruvate Dehydrogenase E1-Beta Deficiency |
| 5 | Leucine-rich PPR Motif-Containing Protein (LRPPRC protein) | MAALLRSARWLLRAGAAPRLPLSLRLLPGGP GRLHAASYLPAARAGPVAGGLLSPARLYAIA AKEKDIQEESTFSSRKISNQFDWALMRLDLS VRRTGRIPKKLLQKVFNDTCRSCiGLGGSII ALLLLRSCGSLLPELKLEERTEFAIIRIWDT LQKLGAVYDVSHYNALLKVYLQNEYKFSPTD FLAKMEEANIQPNRVTYQRLIASYCNVGDIE GASKILGFMKTKDLPVTEAVFSALVTGHARA GDMENAENILTVMRDAGIEPGPDTYLALLNA YAEKGDIDHVKQTLEKVEKSELHLMDRDLLQ IIFSFSKAGYPQYVSEILEKVTCERRYIPDA MNLILLLVTEKLEDVALQILLACPVSKEDGP SVFGSFFLQHCVTMNTPVEKLTDYCKKLKEV QMHSFPLQFTLHCALLANKTDLAKALMKAVK EEGFPIRPHYFWPLLVGRRKEKNVQGIIEIL KGMQELGVHPDQETYTDYVIPCFDSVNSARA ILQENGCLSDSDMFSQAGLRSEAANGNLDFV LSFLKSNTLPISLQSIRSSLLLGFRRSMNIN LWSEITELLYKDGRYCQEPRGPTEAVGYFLY NLIDSMSDSEVQAKEEHLRQYFHQLEKMNVK IPENIYRGIRNLLESYHVPELIKDAHLLVES KNLDFQKTVQLTSSELESTLETLKAENQPIR DVLKQLILVLCSEENMQKALELKAKYESDMV TGGYAALINLCCRHDKVEDALNLKEEFDRLD SSAVLDTGKYVGLVRVLAKHGKLQDAINILK EMKEKDVLIKDTTALSFFHMLNGAALRGEIE TVKQLHEAIVTLGLAEPSTNISFPLVTVHLE KGDLSTALEVAIDCYEKYKVLPRIHDVLCKL VEKGETDLIQKAMDFVSQEQGEMVMLYDLFF AFLQTGNYKEAKKIIETPGIRARSARLQWFC DRCVANNQVETLEKLVELTQKLFECDRDQMY YNLLKLYKINGDWQRADAVWNKIQEENVIPR EKTLRLLAEILREGNQEVPFDVPELWYEDEK HSLNSSSASTTEPDFQKDILIACRLNQKKGA YDIFLNAKEQNIVFNAETYSNLIKLLMSEDY FTQAMEVKAFAETHIKGFTLNDAANSRLHTQ VRRDYLKEAVTTLKTVLDQQQTPSRLAVTRV IQALAMKGDVENIEVVQKMLNGLEDSIGLSK | Leigh Syndrome, French Canadian Type |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | MVFINNIALAQIKNNNIDAAIENIENMLTSE NKVIEPQYFGLAYLFRKVIEEQLEPAVEKIS IMAERLANQFAIYKPVTDFFLQLVDAGKVDD ARALLQRCGAIAEQTPILLLFLLRNSRKQGK ASTVKSVLELIPELNEKEEAYNSLMKSYVSE KDVTSAKALYEHLTAKNTKLDDLFLKRYASL LKYAGEPVPFIEPPESFEFYAQQLRKLRENS S | |
| 6 | SLIRP | <u>MAASAARGAAALRRSINQPVAFVRRIPWTAA SSQLKEHFAQFGHVRRCILPFDKETGFHRGL</u> GWVQFSSEEGLRNALQQENHIIDGVKVQVHT RRPKLPQTSDDEKKDF | Leigh Syndrome, French Canadian Type |
| 7 | Parkin RBR E3 ubiquitin protein ligase (PARK2 protein or PARKIN) | MIVFVRFNSSHGFPVEVDSDTSIFQLKEVVA KRQGVPADQLRVIFAGKELRNDWTVQNCDLD QQSIVHIVQRPWRKGQEMNATGGDDPRNAAG GCEREPQSLTRVDLSSSVLPGDSVGLAVILH TDSRKDSPPAGSPAGRSIYNSFYVYCKGPCQ RVQPGKLRVQCSTCRQATLTLTQGPSCWDDV LIPNRMSGECQSPHCPGTSAEFFFKCGAHPT SDKETSVALHLIATNSRNITCITCTDVRSPV LVFQCNSRHVICLDCFHLYCVTRLNDRQFVH DPQLGYSLPCVAGGPNSLIKELHHFRILGEE QYNRYQQYGAEECVLQMGGVLCPRPGCGAGL LPEPDQRKVTCEGGNGLGCGFAFCRECKEAY HEGECSAVFEASGTTTQAYRVDERAAEQARW EAASKETIKKTTKPCPRCHVPVEKNGGCMHM KCPQPQCRLEWCWNCGCEWNRVCMGDHWFDV | Parkinson's Disease and autosomal recessive juvenile Parkinson's Disease |
| 8 | PTEN-induced kinase 1 (PINK1 or PARK6 protein) | <u>MAVRQALGRGLQLGRALLLRFTGKPGRAYGL GRPGPAAGCVRGERPGWAAGPGAEPRRVGLG LPN</u>RLRFFRQSVAGLAARLQRQFVVRAWGCA GPCGRAVFLAFGLGLGLIEEKQAESRRAVSA CQEIQAIFTQKSKPGPDPLDTRRLQGFRLEE YLIGQSIGKGCSAAVYEATMPTLPQNLEVTK STGLLPGRGPGTSAPGEGQERAPGAPAFPLA IKMMWNISAGSSSEAILNTMSQELVPASRVA LAGEYGAVTYRKSKRGPKQLAPHPNIIRVLR AFTSSVPLLPGALVDYPDVLPSRLHPEGLGH GRTLFLVMKNYPCTLRQYLCVNTPSPRLAAM MLLQLLEGVDHLVQQGIAHRDLKSDNILVEL DPDGCPWLVIADFGCCLADESIGLQLPFSSW YVDRGGNGCLMAPEVSTARPGPRAVIDYSKA DAWAVGAIAYEIFGLVNPFYGQGKAHLESRS YQEAQLPALPESVPPDVRQLVRALLQREASK RPSARVAANVLHLSLWGEHILALKNLKLDKM VGWLLQQSAATLLANRLTEKCCVETKMKMLF LANLECETLCQAALLLCSWRAAL | Parkinson's Disease |
| 9 | Protein deglycase DJ-1 (PARK7 protein) | MASKRALVILAKGAEEMETVIPVDVMRRAGI KVTVAGLAGKDPVQCSRDVVICPDASLEDAK KEGPYDVVVLPGGNLGAQNLSESAAVKEILK EQENRKGLIAAICAGPTALLAHEIGFGSKVT THPLAKDKMMNGGHYTYSENRVEKDGLILTS RGPGTSFEFALAIVEALNGKEVAAQVKAPLV LKD | Parkinson's Disease |
| 72 | Phospholipase A2, Group VI (variant 1) | MQFFGRLVNTFSGVTNLFSNPFRVKEVAVAD YTSSDRVREEGQLILFQNTPNRTWDCVLNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMRVLLLCNARCNI MGPNGYPIHSAMKFSQKGCAEMIISMDSSQI | PLA2G6-associated neuro-degeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRLVTRKAIL TLLRTVGAEYCFPPIHGVPAEQGSAAPHHPF SLERAQPPPISLNNLELQDLMHISRARKPAF ILGSMRDEKRTHDHLLCLDGGGVKGLIIIQL LIAIEKASGVATKDLFDWVAGTSTGGILALA ILHSKSMAYMRGMYFRMKDEVFRGSRPYESG PLEEFLKREFGEHTKMTDVRKPKVMLTGTLS DRQPAELHLFRNYDAPETVREPRFNQVNLR PPAQPSDQLVWRAARSSGAAPTYFRPNGRFL DGGLLANNPTLDAMTEIHEYNQDLIRKGQAN KVKKLSIVVSLGTGRSPQVPVTCVDVFRPSN PWELAKTVFGAKELGKMVVDCCTDPDGRAVD RARAWCEMVGIQYFRLNPQLGTDIMLDEVSD TVLVNALWETEVYIYEHREEFQKLIQLLLSP | |
| 73 | Phospholipase A2, Group VI (variant 2) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRQLQDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | PLA2G6-associated neuro-degeneration (PLAN) |
| 74 | Phospholipase A2, Group VI (variant 3) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRQLQDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD | PLA2G6-associated neuro-degeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | IMLDEVSDTVLVNALWETEVYIYEHREEFQK LIQLLLSP | |
| 75 | Phospholipase A2, Group VI (variant 4) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRLVTRKAIL TLLRTVGAEYCFPPIHGVPAEQGSAAPHHPF SLERAQPPPISLNNLELQDLMHISRARKPAF ILGSMRDEKRTHDHLLCLDGGGVKGLIIIQL LIAIEKASGVATKDLFDWVAGTSTGGILALA ILHSKSMAYMRGMYFRMKDEVFRGSRPYESG PLEEFLKREFGEHTKMTDVRKPKVMLTGTLS DRQPAELHLFRNYDAPETVREPRFNQNVNLR PPAQPSDQLVWRAARSSGAAPTYFRPNGRFL DGGLLANNPTLDAMTEIHEYNQDLIRKGQAN KVKKLSIVVSLGTGRSPQVPVTCVDVFRPSN PWELAKTVFGAKELGKMVVDCCTDPDGRAV DRARAWCEMVGIQYFRLNPQLGTDIMLDEVS DTVLVNALWETEVYIYEHREEFQKLIQLLLS P | PLA2G6-associated neuro-degeneration (PLAN) |
| 76 | Phospholipase A2, Group VI (variant 5) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA NADARGEHGNTPLHLAMSKDNVEMIKALIVF GAEVDTPNDFGETPTFLASKIGRQLQDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | PLA2G6-associated neuro-degeneration (PLAN) |
| 77 | Phospholipase A2, Group VI (variant 6) | MQFFGRLVNTFSGVTNLFSNPFRVKEVAVAD YTSSDRVREEGQLILFQNTPNRTWDCVLVNP RNSQSGFRLFQLELEADALVNFHQYSSQLLP FYESSPQVLHTEVLQHLTDLIRNHPSWSVAH LAVELGIRECFHHSRIISCANCAENEEGCTP LHLACRKGDGEILVELVQYCHTQMDVTDYKG ETVFHYAVQGDNSQVLQLLGRNAVAGLNQVN NQGLTPLHLACQLGKQEMVRVLLLCNARCNI MGPNGYPIHSAMKFSQKGCAEMIISMDSSQI HSKDPRYGASPLHWAKNAEMARMLLKRGCNV NSTSSAGNTALHVAVMRNRFDCAIVLLTHGA | PLA2G6-associated neuro-degeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
|  |  | NADARGEHGNTPLHLAMSKDNVEMIKALIVF GAEVDTPNDFGETPTFLASKIGRQLQDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP |  |
| 78 | Phospholipase A2, Group VI (variant 7) | MDVTDYKGETVFHYAVQGDNSQVLQLLGRNA VAGLNQVNNQGLTPLHLACQLGKQEMVRVLL LCNARCNIMGPNGYPIHSAMKFSQKGCAEMI ISMDSSQIHSKDPRYGASPLHWAKNAEMARM LLKRGCNVNSTSSAGNTALHVAVMRNRFDCA IVLLTHGANADARGEHGNTPLHLAMSKDNVE MIKALIVFGAEVDTPNDFGETPTFLASKIGR LVTRKAILTLLRTVGAEYCFPPIHGVPAEQG SAAPHHPFSLERAQPPPISLNNLELQDLMHI SRARKPAFILGSMRDEKRTHDHLLCLDGGGV KGLIIIQLLIAIEKASGVATKDLFDWVAGTS TGGILALAILHSKSMAYMRGMYFRMKDEVFR GSRPYESGPLEEFLKREFGEHTKMTDVRKPK VMLTGTLSDRQPAELHLFRNYDAPETVREPR FNQNVNLRPPAQPSDQLVWRAARSSGAAPTY FRPNGRFLDGGLLANNPTLDAMTEIHEYNQD LIRKGQANKVKKLSIVVSLGTGRSPQVPVTC VDVFRPSNPWELAKTVFGAKELGKMVVDCCT DPDGRAVDRARAWCEMVGIQYFRLNPQLGTD IMLDEVSDTVLVNALWETEVYIYEHREEFQK LIQLLLSP | PLA2G6-associated neuro-degeneration (PLAN) |
| 79 | Phospholipase A2, Group VI (variant 8) | MGRSWWSWCSTATLRWMSPTTRERPSSIMLS RVTILRCCRCAEMIISMDSSQIHSKDPRYGA SPLHWAKNAEMARMLLKRGCNVNSTSSAGNT ALHVAVMRNRFDCAIVLLTHGANADARGEHG NTPLHLAMSKDNVEMIKALIVFGAEVDTPND FGETPTFLASKIGRLVTRKAILTLLRTVGAE YCFPPIHGVPAEQGSAAPHHPFSLERAQPPP ISLNNLELQDLMHISRARKPAFILGSMRDEK RTHDHLLCLDGGGVKGLIIIQLLIAIEKASG VATKDLFDWVAGTSTGGILALAILHSKSMAY MRGMYFRMKDEVFRGSRPYESGPLEEFLKRE FGEHTKMTDVRKPKVMLTGTLSDRQPAELHL FRNYDAPETVREPRFNQNVNLRPPAQPSDQL VWRAARSSGAAPTYFRPNGRFLDGGLLANNP TLDAMTEIHEYNQDLIRKGQANKVKKLSIVV SLGTGRSPQVPVTCVDVFRPSNPWELAKTVF GAKELGKMVVDCCTDPDGRAVDRARAWCEMV GIQYFRLNPQLGTDIMLDEVSDTVLVNALWE TEVYIYEHREEFQKLIQLLLSP | PLA2G6-associated neuro-degeneration (PLAN) |
| 80 | Phospholipase A2, Group VI (variant 9) | MDVTDYKGETVFHYAVQGDNSQVLQLLGRNA VAGLNQVNNQGLTPLHLACQLGKQEMVRVLL LCNARCNIMGPNGYPIHSAMKFSQKGCAEMI ISMDSSQIHSKDPRYGASPLHWAKNAEMARM LLKRGCNVNSTSSAGNTALHVAVMRNRFDCA IVLLTHGANADARGEHGNTPLHLAMSKDNVE MIKALIVFGAEVDTPNDFGETPTFLASKIGR QLQDLMHISRARKPAFILGSMRDEKRTHDHL LCLDGGGVKGLIIIQLLIAIEKASGVATKDL FDWVAGTSTGGILALAILHSKSMAYMRGMYF RMKDEVFRGSRPYESGPLEEFLKREFGEHTK | PLA2G6-associated neuro-degeneration (PLAN) |

TABLE 2-continued

Exemplary proteins of interest, corresponding human sequences and associated pathological conditions. The underlined portions of the sequences for PDHB protein, LRPPRC protein, SLIRP protein and PINK1 protein are the predicted mitochondrial targeting sequences identified using MitoProt II (M. G. Claros, P. Vincens. Computational method to predict mitochondrially imported proteins and their targeting sequences. *Eur. J. Biochem.* 241, 770-786, the entire contents of which are hereby incorporated herein by reference).

| SEQ ID NO. | Protein | Amino Acid Sequence | Associated Disorder |
|---|---|---|---|
| | | MTDVRKPKVMLTGTLSDRQPAELHLFRNYDA PETVREPRFNQNVNLRPPAQPSDQLVWRAAR SSGAAPTYFRPNGRFLDGGLLANNPTLDAMT EIHEYNQDLIRKGQANKVKKLSIVVSLGTGR SPQVPVTCVDVFRPSNPWELAKTVFGAKELG KMVVDCCTDPDGRAVDRARAWCEMVGIQYFR LNPQLGTDIMLDEVSDTVLVNALWETEVYIY EHREEFQKLIQLLLSP | |

In some embodiments, the protein of interest comprised in the fusion protein of the present disclosure may comprise of consist of any sequence as listed in Table 2, e.g., any one of SEQ ID NOS. 3-9 or 72-80. In some embodiments, the protein of interest comprised in the fusion protein of the present disclosure may comprise or consist of an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of the amino acid sequences listed in Table 2, e.g., any of SEQ ID NOS. 3-9 or 72-80.

In some embodiments, the protein of interest comprised in the fusion protein of the present disclosure comprises or consists of any sequence as listed in Table 2, e.g., any one of SEQ ID NOS. 3-9 or 72-80, and lacks the endogenous OTS, i.e., wherein the endogenous OTS has been removed. An OTS of a particular protein would be easily recognized by one of skill in the relevant art.

In some aspects of the disclosure, the protein of interest may be associated with lysosomes. In some aspects of the disclosure, the protein of interest may be associated with endoplasmic reticulum (ER). In some aspects of the disclosure, the protein of interest may be associated with Golgi apparatus.

In some embodiments, the protein of interest can be a protein that is localized to the nucleus. In some embodiments, the protein of interest can be a protein that is localized to the nucleus and one or more other cellular organelles. The skilled artisan will appreciate that, by introducing a TES to fusion proteins comprising a CPP and such a protein of interest, interference by CPP with localization of the protein of interest will be removed, e.g., aberrant localization to the nucleus will be prevented or reduced, thereby allowing the natural regulatory pathway to dictate the proper cellular localization of the protein in response to endogenous signals, and thereby improve the propensity to relocalize to the appropriate subcellular location. Such proteins may include, e.g., NFKbeta, STAT3, androgen receptor, estrogen receptor, and p53.

In some embodiments, the fusion protein provided by the present disclosure may comprise a protein of interest as described herein, or a functional analogue, derivative or a fragment of the protein of interest. The term "derivative", as used herein, encompasses amino acid sequences (polypeptides) which differ from the polypeptides specifically defined in the present disclosure, e.g., SEQ ID NOS. 3-9 or 72-80, by insertions, deletions, substitutions and modifications of amino acids that do not alter the activity of the original polypeptide. It should be appreciated that by the terms "insertion(s)", "deletion(s)" or "substitution(s)", as used herein, encompasses any addition, deletion or replacement, respectively, of between 1 and 50 amino acid residues of a polypeptide, e.g., between 1 and 5 amino acid residues, between 1 and 10 amino acid residues, between 5 and 15 amino acid residues, between 10 and 20 amino acid residues, between 25 and 40 amino acid residues or between 30 and 50 amino acid residues. More particularly, insertion(s), deletion(s) or substitution(s) may be of any one of 1, 2, 3, 4, 5, 6, 7, 8, 9, or 10 amino acid residues. It should be noted that the insertion(s), deletion(s) or substitution(s) may occur in any position of the modified peptide, as well as in any of the N' or C' termini thereof. In one embodiment, the protein of interest is a derivative of FXN, e.g., human FXN. In one embodiment, the protein of interest is a derivative of Tafazzin. In one embodiment, the protein of interest is a derivative of PDHB. In one embodiment, the protein of interest is a derivative of LRPPRC. In one embodiment, the protein of interest is a derivative of SLIRP. In one embodiment, the protein of interest is a derivative of PARK2 protein. In one embodiment, the protein of interest is a derivative of PINK1 (or PARK6 protein). In one embodiment, the protein of interest is a derivative of PARK7. In one embodiment, the protein of interest is a derivative of Phospholipase A2, Group VI (e.g., variant 1, 2, 3, 4, 5, 6, 7, 8 or 9).

In some embodiments, the amino acid sequence of a protein of interest within the context of the present disclosure may differ from the amino acid sequence of a naturally occurring protein associated with any pathological condition as described above. In some embodiments, the amino acid sequence of a protein of interest as compared to the amino acid sequence of a naturally occurring protein associated with any pathological condition may include a conservative amino acid substitution, i.e., substitution with a structurally-similar amino acid. For instance, structurally similar amino acids include: (isoleucine (I), leucine (L) and valine (V)); (phenylalanine (F) and tyrosine (Y)); (lysine (K) and arginine (R)); (glutamine (Q) and asparagine (N)); (aspartic acid (D) and glutamic acid (E)); and (glycine (G) and alanine (A)).

The term "derivative", as used herein, encompasses homologues, variants and analogues of the original polypeptide, as well as covalent modifications of the original polypeptide. A derivative, a variant and an analogue of any one of the proteins or the peptides comprised in the fusion protein provided in the present disclosure will have the same biological activity as its native form. In one specific embodiment, the protein of interest is a homologue, variant or analogue of FXN, e.g., human FXN.

In some embodiments, a protein of interest which may be comprised in the fusion protein of the present disclosure may be a naturally occurring in a subject. The subject may be a mammal, e.g., a mouse, a rat, a monkey or a human.

Organelle Targeting Sequence (OTS)

In some embodiments, the fusion proteins of the present disclosure may also comprise an organelle targeting sequence (OTS). The term "organelle targeting sequence", or "OTS", as used herein, refers to any amino acid sequence, e.g., a protein, a peptide or a consensus domain, which facilitates delivery of a protein of interest to a specific non-nuclear organelle. For example, an OTS may be a mitochondrial targeting sequence (MTS) that facilitates delivery of a protein of interest to mitochondria. An MTS may be a peptide of about 10-70 amino acids comprising an alternating pattern of hydrophobic and positively charged amino acids that forms an amphipathic helix.

An OTS may also be an endoplasmic reticulum (ER) targeting sequence. An ER targeting sequence may be a peptide of about 16-30 amino acids comprising a hydrophilic region, a hydrophobic domain, and a C-terminal region containing a cleavage site for an ER-specific signal peptidase.

An OTS may also comprise a HEAT motif, which may be present in naturally occurring proteins that localize to the Golgi and endoplasmic reticulum (ER). HEAT is a protein tandem repeat structural motif composed of two alpha helices linked by a short loop. HEAT repeats can form alpha solenoids, a type of solenoid protein domain found in a number of cytoplasmic proteins.

An OTS may also be a peroxisomal targeting signal (PTS) which may be located either at the N-terminus or at the C-terminus of the protein of interest. The N-terminal peroxisomal targeting signal may have a consensus sequence of Arg-Leu-X-X-X-X-His/Gln-Leu, where X may be any amino acid. The C-terminal peroxisomal targeting signal may be short and comprised of Ser-Lys-Leu, but other variations exist, such as PTS2 and mPTS (membrane PTS). mPTS may consist of a cluster of basic amino acids (arginines and lysines) within a loop of protein (i.e., between membrane spans).

An OTS may also be a lysosomal targeting motif, e.g., comprising a sequence Tyr-X-XO, where X may be any amino acid and O may be a bulky hydrophobic amino acid or a dileucine motif (Leu-Leu).

In a fusion protein of the present disclosure, an OTS may be a native sequence, i.e., the OTS may be naturally found within, or be naturally associated with, a protein of interest also present in the fusion protein. For example, the OTS and the protein of interest may be parts of the same naturally occurring polypeptide sequence. In one specific example, a fusion protein of the present disclosure may comprise mature hFXN and an MTS sequence (SEQ ID NO: 10)
MWTLGRRAVAGLLASPSPAQAQTLTRVPRPAELAPLCGRRGLRTDIDAT
CTPRRASSNQRGLNQIWNVKKQSVYLMNLRK, which are both parts of the same naturally occurring polypeptide sequence corresponding to full-length hFXN (SEQ ID NO: 1). Following synthesis in a cell, the naturally occurring polypeptide sequence SEQ ID NO: 1 is processed in a two-step cleavage by the mitochondrial matrix processing peptidase (MPP) as the polypeptide sequence is imported into the mitochondrial matrix. As a result, mature hFXN (SEQ ID NO: 2) which does not comprise MTS is generated.

In other embodiments, an OTS comprised in a fusion protein of the present disclosure may be a heterologous sequence, i.e., not naturally associated with the protein of interest also comprised in the fusion protein. An OTS which is a heterologous sequence may be derived from a protein that is different from the protein of interest comprised in a fusion protein. For example, a fusion protein of the present disclosure may comprise FXN, e.g., mature hFXN, as a protein of interest and an MTS derived from citrate synthase or lipoamide dehydrogenase (LAD), as described in U.S. Pat. No. 8,912,147, the entire contents of which are incorporated herein by reference. A heterologous OTS may be a fragment from another protein, produced by cleavage, by recombinant technology, or it may be chemically synthesized, and further fused to the protein of interest.

In some embodiments, an OTS may comprise an amino acid sequence that has at least 85%, e.g., at least 90%, at least 95%, at least 96%, at least 97%, at least 98%, at least 99% or 100% sequence identity to a naturally occurring OTS domain of a native protein or a heterologous protein.

In some embodiments, a fusion protein of the present disclosure comprises an MTS, e.g., (SEQ ID NO: 10)
MWTLGRRAVAGLLASPSPAQAQTLTRVPRPAELAPLCGRRGLRTDIDAT
CTPRRASSNQRGLNQIWNVKKQSVYLMNLRK.

In other examples the fusion protein of the present disclosure comprises an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10. In some embodiments, a fusion protein may comprise a functional analogue, derivative or a fragment of SEQ ID NO: 10, as defined above.

In some embodiments, an OTS may be naturally associated with a protein of interest, e.g., a protein of interest in its naturally occurring form may comprise an OTS as a part of its sequence. One example of such protein of interest is full length hFXN (SEQ ID NO: 1), which comprises, as parts of its sequence, an MTS (SEQ ID NO: 10) and a mature hFXN (SEQ ID NO: 2). When a protein of interest comprising OTS as a part of its sequence is included in a fusion protein of the present disclosure, the fusion protein does not include another OTS, in addition to the OTS present as a part of the protein of interest.

In other embodiments, an OTS naturally associated with a protein of interest may be substituted with an OTS that does not occur naturally together with the protein of interest. For example, an MTS that is a part of full length hFXN and that is naturally associated with hFXN (SEQ ID NO: 10) may be substituted with a different OTS, e.g., an MTS derived from citrate synthase or lipoamide dehydrogenase (LAD), as described in U.S. Pat. No. 8,912,147. Thus, a fusion protein of the present disclosure may comprise mature hFXN (SEQ ID NO: 2) and an MTS that is different from SEQ ID NO: 10, such as an MTS derived from LAD.

In some embodiments, an OTS may be absent from a fusion protein of the present disclosure. For example, a fusion protein of the present disclosure may comprise a protein of interest, a CPP, e.g., HIV-TAT, and a TES, and lack an OTS. In some embodiments, a fusion protein of the present disclosure consists of a protein of interest, a CPP, e.g., HIV-TAT, and a TES.

Cell Penetrating Peptide (CPP)

The fusion proteins provided by the present disclosure also comprise a cell penetrating peptide (CPP). Cell penetrating peptides (CPPs) are short peptide sequences, typically between 5 and 30 amino acids long, that can facilitate cellular intake of various molecular cargo, such as proteins. CPPs may be polycationic, i.e., have an amino acid composition that either contains a high relative abundance of positively charged amino acids, such as lysine or arginine. CCPs may also be amphipathic, i.e., have sequences that contain an alternating pattern of polar/charged amino acids and non-polar, hydrophobic amino acids. CPPs may also be hydrophobic, i.e., contain only apolar residues with low net charge, or have hydrophobic amino acid groups that are crucial for cellular uptake.

A CPP useful in the context of the present disclosure may be any CPP known to a person skilled in the art. For example, a CPP comprised in the fusion protein of the present disclosure may be any CPP listed in the Database of Cell-Penetrating Peptides CPPsite 2.0, the entire contents of which are hereby incorporated herein by reference. For examples, CPPs useful in the context of the present disclosure may be selected from the group consisting of HIV-TAT (which may also be referred to herein as "TAT"), galanin, mastoparan, transportan, penetratin, polyarginine, or VP22. In one specific embodiment, the CPP is HIV-TAT. Table 4 below lists amino acid sequences of the exemplary CPPs.

ID NO: 12, SEQ ID NO: 13, SEQ ID NO: 14, SEQ ID NO: 15, SEQ ID NO: 16, SEQ ID NO: 17 or SEQ ID NO: 83.

In one embodiment, CPP comprised in the fusion protein of the present disclosure is HIV-TAT, e.g., SEQ ID NO: 11. In another specific example, CPP comprised in the fusion protein of the present disclosure is HIV-TAT (with N-terminal methionine), e.g., SEQ ID NO: 83. In another example, the fusion protein of the present disclosure comprises full-length FXN, e.g., SEQ ID NO: 1 and HIV-TAT as CPP. In another further example, the fusion protein of the present disclosure comprises mature FXN, e.g., SEQ ID NO: 2, as the protein of interest and HIV-TAT as CPP.

In some embodiments, and without wishing to be bound by a specific theory, it is believed that a CPP comprised in the fusion protein of the present disclosure may be capable of interference with delivery of the protein of interest, also comprised in the fusion protein, to an organelle, e.g., a non-nuclear organelle. For example, as illustrated in Example 1 of the present disclosure, the TAT-GG-hFXN fusion protein is localized primarily in the cytosol and in the nucleus, but not in the mitochondria.

Target Enhancing Sequence (TES)

A fusion protein of the present disclosure also comprises a target enhancing sequence (TES). The term "target enhancing sequence" (TES), as used herein, refers to an amino acid sequence that, when present in a fusion protein comprising a CPP, prevents or attenuates interference by the CPP with delivery of the protein of interest to its appropriate subcellular location. For example, in some embodiments the TES, as used herein, refers to an amino acid sequence that facilitates the effective delivery of the protein of interest to the intended organelle (e.g., a non-nuclear organelle, such as

TABLE 4

Exemplary CPPs and corresponding sequences

| SEQ ID NO. | CPP | Amino Acid Sequence |
|---|---|---|
| 11 | HIV-TAT | YGRKKRRQRRR |
| 12 | Galanin | GWTLNSAGYLLGPHAVGNHRSFSDKNGLTS |
| 13 | Mastoparan | INLKALAALAKKIL-NH$_2$ |
| 14 | Transportan | GWTLNSAGYLLGKINLKALAALAKKIL |
| 15 | Penetratin | RQIKIWFQNRRMKWKK |
| 16 | Polyarginine | RRRRRRRRR |
| 17 | VP22 | DAATATRGRSAASRPTERPRAPARSASRPRRPVE |
| 83 | HIV-TAT (with N-terminal methionine) | MYGRKKRRQRRR |

In some examples, fusion proteins of the present disclosure may comprise an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of the amino acid sequences listed in Table 4, i.e., SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 83. In some examples, fusion proteins of the present disclosure may comprise a functional analogue, derivative or a fragment of the protein of interest of any one of the amino acid sequences listed in Table 4, i.e., SEQ ID NO: 11, SEQ mitochondria) by removing or attenuating interference with delivery of the protein of interest to the intended organelle brought about by the CPP. Exemplary TES may include a protease sensitive sequence, also referred herein as "protease cleavable domain", "protease sensitive domain", "protease sensitive protein" or "protease sensitive peptide". Exemplary TES may also include a nuclear export signal peptide.

A protease-sensitive peptide may be also referred to as a "protease cleavage site". A protease-sensitive peptide or protease cleavage site refers to a specific amino acid motif within an amino acid sequence which is recognized and cleaved by a specific intracellular cytosolic protease.

As mentioned above, in some embodiments, in the fusion proteins of the present disclosure, CPP may be capable of interference with delivery to a non-nuclear organelle of the protein of interest comprised in the fusion protein. TES comprising a protease cleavage site facilitates removal of the CPP from the fusion protein, thereby preventing the interference by CPP. For example, as illustrated in FIG. 1, panel A, in some exemplary fusion proteins of the present disclosure, CPP may be located at the N-terminus of the fusion protein and TES may be fused at the C-terminal side of the CPP. When the fusion protein is exposed to an endogenous protease, the endogenous protease may cleave TES at the protease cleavage site, facilitating removal of the CPP from the N-terminus of the fusion protein. Similarly, as illustrated in FIG. 1, panel B, in other exemplary fusion proteins of the present disclosure, CPP may be located at the C-terminus of the fusion protein and TES may be fused at the N-terminal side of the CPP. When the fusion protein is exposed to an endogenous protease, the endogenous protease may cleave TES at the protease cleavage site, thereby removing the CPP from the C-terminus of the fusion protein.

Non-limiting examples of protease sensitive peptide or proteins that may be comprised in the TES include ubiquitin-like modifiers, such as ubiquitin, caspase cleavage domains, calpain cleavage domains, SUMO1, SUMO2, SUMO3, SUMO4, ISG15, Atg8, Atg12, and NEDD8.

Ubiquitin is highly conserved through eukaryote organisms, and the sequence of the human ortholog is:

(SEQ ID NO. 18)
MQIFVKTLTGKTITLEVEPSDTIENVKAKIQDKEGIPPDQQRLIFAGKQ
LEDGRTLSDYNIQKESTLHLVLRLRGG.

An exemplary caspase cleavage domain may comprise DEVD (SEQ ID NO. 19).

Nonlimiting examples of calpain cleavage domains are EPLFAERK (SEQ ID NO. 20) or LLVY (SEQ ID NO. 21).

Other exemplary protease cleavage sites may include any cleavage site described in Waugh, *Protein Expr. Purif.* 2011, 80(2):283-293, the entire contents of each of which are hereby incorporated herein by reference.

Exemplary proteases with specific protease cleavage sites may include ubiquitinase, caspase, calpain, enterokinase (light chain), enteropeptidase, prescission protease, human rhinovirus protease (HRV 3C), TEV (Tobacco Etch Virus) protease, TVMV (tobacco vein mottling virus) protease, Factor Xa protease, thrombin, and other proteases known to the person skilled in the art. Table 5 below includes some examples of amino acid sequences of protease cleavage sites and their respective proteases.

TABLE 5

Exemplary protease cleavage sites and corresponding proteases

| SEQ ID NO. | Protease | Cleavage Site Sequence |
| --- | --- | --- |
| 22 | Enterokinase (light chain)/ Enteropeptidase | DDDDK |
| 23 | PreScission Protease/human Rhinovirus protease (HRV 3C) | LEVLFQP |
| 24 | TEV protease | LEVLFGP |
| 25 | TEV protease | ENLYFQS |
| 26, 84 | TEV protease | Modified motifs based on the EXXYXQG (SEQ ID NO: 26) and EXXYXQS (SEQ ID NO: 84), where X may be any amino acid. |
| 27 | TVMV protease | ETVRFQS |
| 28 | Factor Xa protease | IEGR |
| 29 | Factor Xa protease | IDGR |
| 30 | Thrombin | LVPRS |
| 31 | Thrombin | LVPGS |

SUMO (Small Ubiquitin-like Modifier) proteins are a family of small proteins (about 100 amino acids in length and about 12 kDa in molecular weight) that are covalently attached to and detached from other proteins in cells to modify their function. The exact length and molecular weight vary between SUMO family members and depend on the organism from which the protein is derived. Examples of SUMO proteins are SUMO1, SUMO2, SUMO3 and SUMO4 with amino acid sequences as listed in Table 6 below.

TABLE 6

Amino acid sequences of SUMO proteins.

| SEQ ID NO. | SUMO Protein | Amino Acid Sequence |
| --- | --- | --- |
| 32 | SUMO1 | MSDQEAKPSTEDLGDKKEGEYIKLKVIGQDSSEIHFK VKMTTHLKKLKESYCQRQGVPMNSLRFLFEGQRIAD NHTPKELGMEEEDVIEVYQEQTGG |
| 33 | SUMO2 | MADEKPKEGVKTENNDHINLKVAGQDGSVVQFKIKR HTPLSKLMKAYCERQGLSMRQIRFRFDGQPINETDTP AQLEMEDEDTIDVFQQQTGGVY |
| 34 | SUMO3 | MSEEKPKEGVKTENDHINLKVAGQDGSVVQFKIKRH TPLSKLMKAYCERQGLSMRQIRPRFDGQPINETDTPA QLEMEDEDTIDVFQQQTGGVPESSLAGHSF |
| 35 | SUMO4 | MANEKPTEEVKTENNNHINLKVAGQDGSVVQFKIKR QTPLSKLMKAYCEPRGLSMKQIRFRFGGQPISGTDKP AQLEMEDEDTIDVFQQPTGGVY |

In some embodiments, TES comprised in a fusion protein of the present disclosure may comprise a protease sensitive peptide or protein. In some examples, the TES may comprise a sequence described herein, e.g., any one of SEQ ID NOS. listed in Table 5 (SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 or SEQ ID NO: 84), or a sequence having at least 85%, e.g., at least 90% or at least 95% sequence identity with any one of SEQ ID NOS. listed in Table 5 (SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 84). In some examples, fusion proteins of the present disclosure may comprise a functional analogue, derivative or a fragment of the protein of interest of any one of SEQ ID NOS. listed in Table 5 (SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 or SEQ ID NO: 84).

In other embodiments, TES comprised in a fusion protein of the present disclosure may comprise a ubiquitin-like modifier. In some examples, the TES may comprise a sequence described herein, e.g., any one of SEQ ID NOS. listed in Table 6 (SEQ ID NO: 32, SEQ ID NO: 33, SEQ ID NO: 34 or SEQ ID NO: 35), or a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98% or at least 99% sequence identity with any one of SEQ ID NOS. listed in Table 6 (SEQ ID NO: 32, SEQ ID NO: 33, SEQ ID NO: 34 or SEQ ID NO: 35). In some examples, fusion proteins of the present disclosure may comprise a functional analogue, derivative or a fragment of the protein of interest of any one of SEQ ID NOS. listed in Table 6 (SEQ ID NO: 32, SEQ ID NO: 33, SEQ ID NO: 34 or SEQ ID NO: 35).

Amino acid sequences having at least 85% sequence identity to any of SEQ ID NOS. 22-31 or any of SEQ ID NOS. 32-35 may be found in one or more of the following databases: GenBank, Protein Data Bank (PDB), SwissProt, Protein Information Resource (PIR), or Protein Research Foundation (PRF).

In some examples, TES comprised in a fusion protein of the present disclosure may comprise a nuclear export signal (NES). NES, when present in a protein, targets the protein for export from the cell nucleus into the cytoplasm. The export of the protein occurs through the nuclear pore complex via nuclear transport. Accordingly, in the context of the present disclosure, when a CPP present in a fusion protein facilitates delivery of the protein of interest to nucleus, TES counteracts said action by the CPP by facilitating export of the protein of interest from the nucleus into cytoplasm. In this manner, TES increases the likelihood that the protein of interest will be delivered to a non-nuclear organelle of interest, i.e., to mitochondria.

In some examples, NES may be a peptide comprising four hydrophobic residues which may not necessarily be in tandem. For example, NES may be a peptide comprising an amino acid sequence LXXXLXXLXL, where "L" is a hydrophobic residue (often leucine) and "X" is any amino acid other than leucine. Without wishing to be bound by a specific theory, it is believed that the spacing of the hydrophobic residues in an NES may be explained by examining known structures that contain an NES, as the critical residues usually lie in the same face of adjacent secondary structures within a protein, which allows them to interact with the exportin.

Any NES known to one of ordinary skill in the art is encompassed by the present disclosure, including NES listed in the NESbase version 1.0, a database of nuclear export signals, the entire contents of which are hereby incorporated herein by reference. Table 7 lists certain exemplary NESs and their corresponding sequences.

TABLE 7

Exemplary NESs and corresponding sequences.

| SEQ ID NO. | SUMO Protein | Amino Acid Sequence |
| --- | --- | --- |
| 36 | NES1 | LALKLAGLDL |
| 37 | NES2 | LQKKLEELEL |
| 38 | NES3 | MQELSNILNL |
| 39 | NES4 | LPPLERLTL |
| 40 | NES5 | LCQAFSDVIL |
| 41 | NES6 | RTFDMHSLESSLIDIMR |
| 42 | NES7 | TNLEALQKKLEELELDE |
| 43 | NES8 | RSFEMTEFNQALEEIKG |

In some embodiments of the present disclosure, TES may comprise a sequence described herein, e.g., any one of SEQ ID NOS. listed in Table 7 (SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43), or a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98% or at least 99% sequence identity with any one of SEQ ID NOS. listed in Table 7 (SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43). In some examples, fusion proteins of the present disclosure may comprise a functional analogue, derivative or a fragment of the protein of interest of any one of SEQ ID NOS. listed in Table 7 (SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43).

Amino acid sequences having at least 85% sequence identity to any of SEQ ID NOS. 36-43 may be found in one or more of the following databases: GenBank, Protein Data Bank (PDB), SwissProt, Protein Information Resource (PIR), or Protein Research Foundation (PRF).

Fusion Protein

In an embodiment of the disclosure a fusion protein provided herein may comprise a protein of interest to be delivered to a non-nuclear organelle, an organelle targeting sequence (OTS), a cell penetrating peptide (CPP), and a target enhancing sequence (TES), wherein the CPP is capable of interference with delivery of the protein of interest to the non-nuclear organelle and wherein the TES prevents said interference by the CPP. In some examples, the protein of interest, OTS, CPP and TES may be directly fused to each other directly to form a single polypeptide chain. In other examples, the protein of interest, OTS, CPP and TES may be fused to each other via a spacer to form a single polypeptide chain.

In one specific embodiment, the protein of interest is FXN, e.g., SEQ ID NO: 2. In one specific embodiment, the OTS is MTS, e.g., SEQ ID NO: 10. In one specific embodiment, the CPP is HIV-TAT, e.g., SEQ ID NO: 11. In one specific embodiment, the TES may be a protease sensitive peptide or proteins, e.g., SUMO 1 (e.g., SEQ ID NO: 32); ubiquitin (e.g., SEQ ID NO: 18); a caspase cleavage site, e.g., DEVD (SEQ ID NO: 19) or a calpain cleavage site, e.g., EPLFAERK (SEQ ID NO: 20) or LLVY (SEQ ID NO: 21). In one specific embodiment, the TES may be an NES, e.g., NES1 (SEQ ID NO: 36) or NES2 (SEQ ID NO: 37).

In an embodiment of the disclosure a fusion protein provided herein may comprise a protein of interest to be delivered to a cell, a cell penetrating peptide (CPP) and a target enhancing sequence (TES). In some embodiments, the CPP is capable of interference with the delivery of the protein of interest to a cell and/or to a cellular organelle, and the TES prevents said interference by the CPP. In some examples, the protein of interest, CPP and TES may be directly fused to each other directly to form a single polypeptide chain. In other examples, the protein of interest, CPP and TES may be fused to each other via a spacer to form a single polypeptide chain.

In one specific embodiment, the protein of interest is PARKIN, e.g., SEQ ID NO: 7. In one specific embodiment, the CPP is HIV-TAT, e.g., SEQ ID NO: 11. In one specific embodiment, the TES may be a protease sensitive peptide or proteins, e.g., SUMO 1 (e.g., SEQ ID NO: 32); ubiquitin (e.g., SEQ ID NO: 18); a caspase cleavage site, e.g., DEVD (SEQ ID NO: 19), or a calpain cleavage site, e.g., EPL-FAERK (SEQ ID NO: 20), or LLVY (SEQ ID NO: 21). In one specific embodiment, the TES may be an NES, e.g., NES1 (SEQ ID NO: 36) or NES2 (SEQ ID NO: 37).

Figure 2:
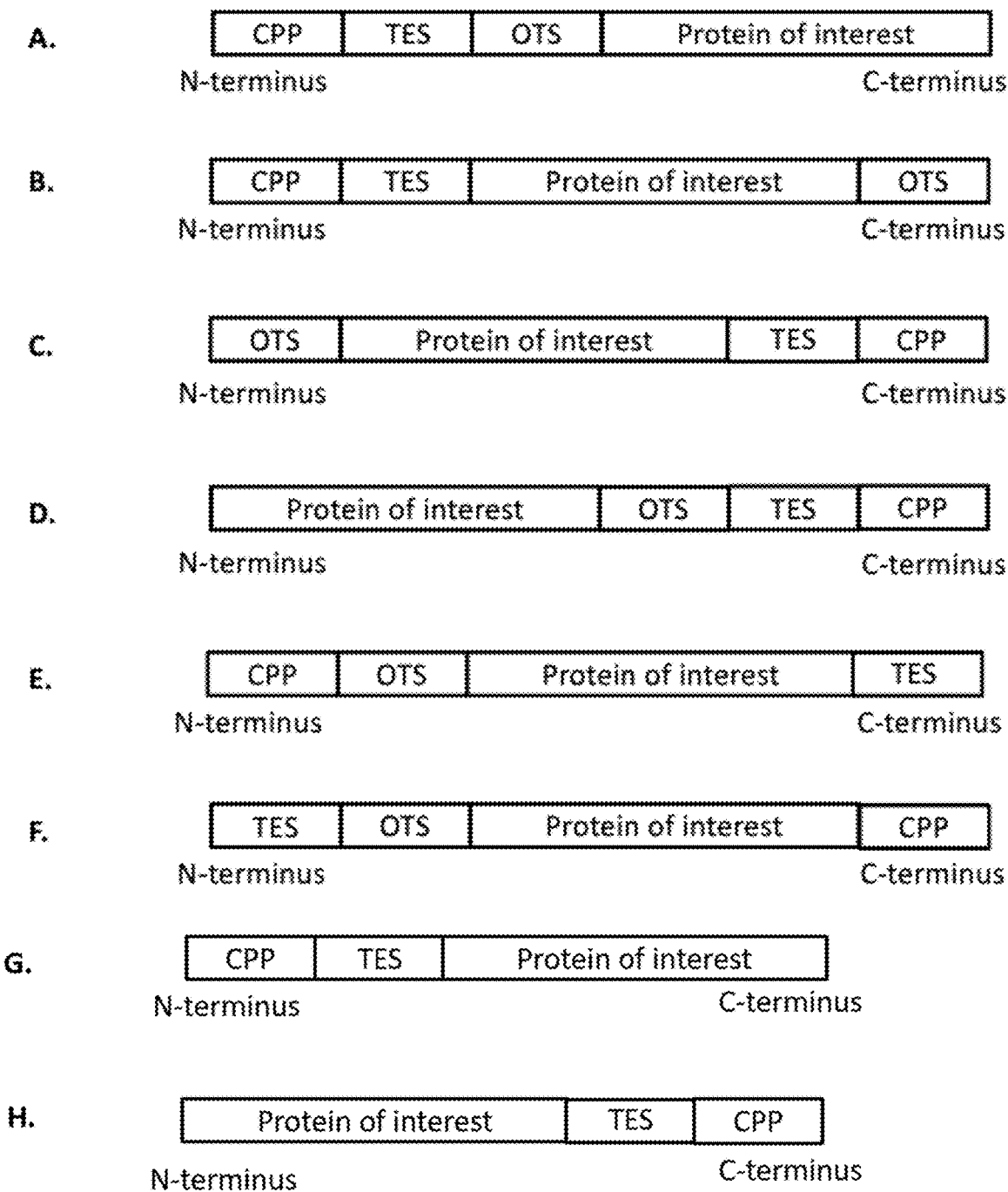
FIG. 2 is a schematic illustrating configurations of various domains in the fusion proteins of the present disclosure.

In the fusion proteins provided by the present disclosure, the positions of protein of interest, OTS (if present), CPP and TES relative to each other and the N-terminus and the C-terminus may vary. Exemplary fusion proteins comprising different relative configurations of the protein of interest, OTS, CPP and TES are shown in FIG. 2. For example, as illustrated in FIG. 2, Panel A, an exemplary fusion protein may comprise, starting from the N-terminus, CPP, followed by TES, followed by OTS, followed by protein of interest at the C-terminus. In another example illustrated in FIG. 2, Panel B, a fusion protein may comprise, starting from the N-terminus, CPP, followed by TES, followed by the protein of interest, followed by OTS at the C-terminus. In another example illustrated in FIG. 2, Panel C, an exemplary fusion protein may comprise, starting from the N-terminus, OTS, followed by the protein of interest, followed by TES, followed by CPP at the C-terminus. In another example illustrated in FIG. 2, Panel D, a fusion protein may comprise, starting from the N-terminus, protein of interest, followed by OTS, followed by TES, followed by CPP at the C-terminus. In another example illustrated in FIG. 2, Panel E, a fusion protein may comprise, starting from the N-terminus, CPP, followed by OTS, followed by protein of interest, followed by TES. In yet another example illustrated in FIG. 2, Panel F, a fusion protein may comprise, starting at the N-terminus, TES, followed by OTS, followed by protein of interest, followed by CPP. In yet another example illustrated in FIG. 2, Panel G, a fusion protein may comprise, starting at the N-terminus, CPP, followed by TES, followed by protein of interest. In yet another example illustrated in FIG. 2, Panel H, a fusion protein may comprise, starting at the N-terminus, protein of interest, followed by TES, followed by CPP.

In some examples, in fusion proteins of the present disclosure, various domains (i.e., protein of interest, CPP, OTS, if present, and TES) may be fused to each other directly to form a single polypeptide chain. As used herein, the term "directly" means that there are no interfering amino acids between the C-terminal amino acid of the first domain and the N-terminal amino acid of the second domain that are directly fused to each other. That is, the (first or last) amino acid at the terminal end (N or C-terminal end) of the first domain may fused to the (first or last) amino acid at the terminal end (N or C-terminal end) of the second domain, forming a single polypeptide. In other words, in this embodiment, the last amino acid of the C-terminal end of a first domain is linked directly by a covalent bond to the first amino acid of the N-terminal end of the second domain, or the first amino acid of the N-terminal end of the fist domain is directly linked by a covalent bond to the last amino acid of the C-terminal end of to form a single polypeptide.

In other examples, in fusion proteins of the present disclosure, various domains (i.e., protein of interest, CPP, OTS, if present, and TES) may be fused together via a spacer to form a single polypeptide chain. As used herein, the term "spacer", which may be used interchangeably with the term "linker", refers to a sequence of at least one amino acid that links together two domains to form a single polypeptide chain. When included in a fusion protein, a spacer may prevent steric hindrances. In some example, length of a spacer or a linker may vary from 2 to 31 amino acids, e.g., from 2-10 amino acids, from 5 to 15 amino acids, from 10 to 25 amino acids or from 12 to 31 amino acids. One of ordinary skill in the art would be able to determine an appropriate linker or spacer length for each specific fusion protein, such that the linker or spacer does not impose any constraints on the conformation of the fusion protein, or interactions of the domains of the fusion protein with each other. A linker or a spacer may be a previously described endogenous and naturally occurring linker or spacer that plays a role in separating domains within a protein or for the formation of dimers. Alternatively a linker or a spacer may be an artificially designed linker or a spacer useful in recombinant technology for the generation of fusion proteins. Examples of linkers or spacers useful within the context of the present disclosure are shown in Table 8 below.

TABLE 8

Exemplary linkers or spacers.

| SEQ ID NO. | Amino Acid Sequence |
|---|---|
| 44 | GGGGSLVPRGSGGGGS |
| 45 | GSGSGS |
| 46 | GSGSGSGSGSGSGSGS |
| 47 | GGSGGHMGSGG |
| 48 | GGSGGSGGSGG |
| 49 | GGSGG |

TABLE 8-continued

Exemplary linkers or spacers.

| SEQ ID NO. | Amino Acid Sequence |
|---|---|
| 50 | GGGSEGGGSEGGGSEGGG |
| 51 | AAGAATAA |
| 52 | GGGGG |
| 53 | GGSSG |
| 54 | GSGGGTGGGSG |
|  | GT |
|  | GG |

In some embodiments, a fusion protein of the present disclosure may comprise a GG (Gly-Gly) linker. For example, a fusion protein of the present disclosure may comprise a GG linker connecting a CPP domain to the TES domain, e.g., a protease cleavage site. In another example, a fusion protein of the present disclosure may comprise a GG linker connecting a CPP domain to the OTS domain, e.g., MTS. In one specific embodiment, TAT-CPP is connected to MTS-FXN via a GG linker.

Exemplary fusion proteins of the present disclosure and their corresponding sequences are listed in Table 9 below.

TABLE 9

Exemplary fusion proteins.

| SEQ ID NO. | Fusion Protein | Sequence |
|---|---|---|
| 55 | TAT-GG-SUMO1-hFXN | MYGRKKRRQRRRGGMSDQEAKPSTEDLGDKKEGEYIKLVI GQDSSEIHFKVKMTTHLKKLKESYCQRQGVPMNSLRFLFEGQ RIADNHTPKELGMEEEDVIEVYQEQTGGMWTLGRRAVAGLL ASPSPAQAQTLTRVPRPAELAPLCGRRGLRTDIDATCTPRRASS NQRGLNQIWNVKKQSVYLMNLRKSGTLGHPGSLDETTYERL AEETLDSLAEFFEDLADKPYTIAEDYDVSFGSGVLTVKLGGDLG TYVINKQTPNKQIWLSSPSSGPKRYDWTGKNWVYSHDGVSLH ELLAAELTKALKTKLDLSSLAYSGKDA |
| 81 | TAT-GG-SUMO-hFXN | MYGRKKRRQRRRGGSDSEVNQEAKPEVKPEVKPETHINLKVS DGSSEIFFKIKKTTPLRRLMEAFAKRQGKEMDSLRFLYDGIRIQ ADQTPEDLDMEDNDIIEAHREQIGGMWTLGRRAVAGLLASPS PAQAQTLTRVPRPAELAPLCGRRGLRTDIDATCTPRRASSNQR GLNQIWNVKKQSVYLMNLRKSGTLGHPGSLDETTYERLAEET LDSLAEFFEDLADKPYTIAEDYDVSFGSGVLTVKLGGDLGTYVI NKQTPNKQIWLSSPSSGPKRYDWTGKNWVYSHDGVSLHELL AAELTKALKTKLDLSSLAYSGKDA |
| 56 | TAT-GG-Ubiquitin-hFXN | MYGRKKRRQRRRGGMQIFVKTLTGKTITLEVEPSDTIENVKA KIQDKEGIPPDQQRLIFAGKQLEDGRTLSDYNIQKESTLHLVLR LRGGMWTLGRRAVAGLLASPSPAQAQTLTRVPRPAELAPLCG RRGLRTDIDATCTPRRASSNQRGLNQIWNVKKQSVYLMNLRK SGTLGHPGSLDETTYERLAEETLDSLAEFFEDLADKPYTFEDY DVSFGSGVLTVKLGGDLGTYVINKQTPNKQIWLSSPSSGPKRY DWTGKNWVYSHDGVSLHELLAAELTKALKTKLDLSSLAYSG KDA |
| 57 | TAT-GG-DEVD-hFXN | MYGRKKRRQRRRGGDEVDMWTLGRRAVAGLLASPSPAQAQ TLTRVPRPAELAPLCGRRGLRTDIDATCTPRRASSNQRGLNQI WNVKKQSVYLMNLRKSGTLGHPGSLDETTYERLAEETLDSLA EFFEDLADKPYTIAEDYDVSFGSGVLTVKLGGDLGTYVINKQTP NKQIWLSSPSSGPKRYDWTGKNWVYSHDGVSLHELLAAELT KALKTKLDLSSLAYSGKDA |
| 58 | TAT-GG-EPLFAERK-hFXN | MYGRKKRRQRRRGGEPLFAERKMWTLGRRAVAGLLASPSPA QAQTLTRVPRPAELAPLCGRRGLRTDIDATCTPRRASSNQRGL NQIWNVKKQSVYLMNLRKSGTLGHPGSLDETTYERLAEETLD SLAEFFEDLADKPYTIAEDYDVSFGSGVLTVKLGGDLGTYVINK |

TABLE 9-continued

Exemplary fusion proteins.

| SEQ ID NO. | Fusion Protein | Sequence |
|---|---|---|
| | | QTPNKQIWLSSPSSGPKRYDWTGKNWVYSHDGVSLHELLAAE LTKALKTKLDLSSLAYSGKDA |
| 59 | TAT-GG-LLVY-hFXN | MYGRKKRRQRRRGGLLVYMWTLGRRAVAGLLASPSPAQAQ TLTRVPRPAELAPLCGRRGLRTDIDATCTPRRASSNQRGLNQI WNVKKQSVYLMNLRKSGTLGHPGSLDETTYERLAEETLDSLA EFFEDLADKPYTIAEDYDVSFGSGVLTVKLGGDLGTYVINKQTP NKQIWLSSPSSGPKRYDWTGKNWVYSHDGVSLHELLAAELT KALKTKLDLSSLAYSGKDA |
| 60 | TAT-GG-hFXN-NES1 | MYGRKKRRQRRRGGMWTLGRRAVAGLLASPSPAQAQTLTR VPRPAELAPLCGRRGLRTDIDATCTPRRASSNQRGLNQIWNVK KQSVYLMNLRKSGTLGHPGSLDETTYERLAEETLDSLAEFFED LADKPYTIAEDYDVSFGSGVLTVKLGGDLGTYVINKQTPNKQI WLSSPSSGPKRYDWTGKNWVYSHDGVSLHELLAAELTKALK TKLDLSSLAYSGKDALALKLAGLDL |
| 61 | TAT-GG-hFXN-NES2 | MYGRKKRRQRRRGGMWTLGRRAVAGLLASPSPAQAQTLTR VPRPAELAPLCGRRGLRTDIDATCTPRRASSNQRGLNQIWNVK KQSVYLMNLRKSGTLGHPGSLDETTYERLAEETLDSLAEFFED LADKPYTIAEDYDVSFGSGVLTVKLGGDLGTYVINKQTPNKQI WLSSPSSGPKRYDWTGKNWVYSHDGVSLHELLAAELTKALK TKLDLSSLAYSGKDALQKKLEELEL |
| 69 | TAT-GG-Ubiquitin-PARKIN | MYGRKKRRQRRRGGMQIFVKTLTGKTITLEVEPSDTIENVKA KIQDKEGIPPDQQRLIFAGKQLEDGRTLSDYNIQKESTLHLVLR LRGGMIVFVRFNSSHGFPVEVDSDTSIFQLKEVVAKRQGVPAD QLRVIFAGKELRNDWTVQNCDLDQQSIVHIVQRPWRKGQEM NATGGDDPRNAAGGCEREPQSLTRVDLSSSVLPGDSVGLAVIL HTDSRKDSPPAGSPAGRSIYNSFYVYCKGPCQRVQPGKLRVQ CSTCRQATLTLTQGPSCWDDVLIPNRMSGECQSPHCPGTSAEF FFKCGAHPTSDKETSVALHLIATNSRNITCITCTDVRSPVLVFQ CNSRHVICLDCFHLYCVTRLNDRQFVHDPQLGYSLPCVAGCP NSLIKELHHFRILGEEQYNRYQQYGAEECVLQMGGVLCPRPG CGAGLLPEPDQRKVTCEGGNGLGCGFAFCRECKEAYHEGECS AVIALASGTTTQAYRVDERAAEQARWEAASKETIKKTTKPCPR CHVPVEKNGGCMHMKCPQPQCRLEWCWNCGCEWNRVCMG DHWFDV |
| 70 | TAT-GG-EPLFAERK-PARKIN | MYGRKKRRQRRRGGEPLFAERKMIVFVRFNSSHGFPVEVDSD TSIFQLKEVVAKRQGVPADQLRVIFAGKELRNDWTVQNCDLD QQSIVHIVQRPWRKGQEMNATGGDDPRNAAGGCEREPQSLTR VDLSSSVLPGDSVGLAVILHTDSRKDSPPAGSPAGRSIYNSFYV YCKGPCQRVQPGKLRVQCSTCRQATLTLTQGPSCWDDVLIPN RMSGECQSPHCPGTSAEFFFKCGAHPTSDKETSVALHLIATNS RNITCITCTDVRSPVLVFQCNSRHVICLDCFHLYCVTRLNDRQF VHDPQLGYSLPCVAGCPNSLIKELHHFRILGEEQYNRYQQYGA EECVLQMGGVLCPRPGCGAGLLPEPDQRKVTCEGGNGLGCGF AFCRECKEAYHEGECSAVFEASGTTTQAYRVDERAAEQARW EAASKETIKKTTKPCPRCHVPVEKNGGCMHMKCPQPQCRLE WCWNCGCEWNRVCMGDHWFDV |
| 71 | TAT-GG-PARKIN-NES1 | MYGRKKRRQRRRGGMIVFVRFNSSHGFPVEVDSDTSIFQLKE VVAKRQGVPADQLRVIFAGKELRNDWTVQNCDLDQQSIVHIV QRPWRKGQEMNATGGDDPRNAAGGCEREPQSLTRVDLSSSV LPGDSVGLAVILHTDSRKDSPPAGSPAGRSIYNSFYVYCKGPC QRVQPGKLRVQCSTCRQATLTLTQGPSCWDDVLIPNRMSGEC QSPHCPGTSAEFFFKCGAHPTSDKETSVALHLIATNSRNITCITC TDVRSPVLVFQCNSRHVICLDCFHLYCVTRLNDRQFVHDPQL GYSLPCVAGCPNSLIKELHHFRILGEEQYNRYQQYGAEECVLQ MGGVLCPRPGCGAGLLPEPDQRKVTCEGGNGLGCGFAFCREC KEAYHEGECSAVIALASGTTTQAYRVDERAAEQARWEAASKE TIKKTTKPCPRCHVPVEKNGGCMHMKCPQPQCRLEWCWNCG CEWNRVCMGDHWFDVLALKLAGLDL |

In some embodiments, the fusion protein provided by the present disclosure comprises or consists of any one sequence as listed in Table 9, i.e., any of SEQ ID NOS: 55-61, 69-71 or 81 (SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 69, SEQ ID NO: 70, SEQ ID NO: 71 or SEQ ID NO: 81). In some embodiments, the fusion protein provided by the present disclosure comprises or consists of an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one sequence listed in Table 9, e.g., any of SEQ ID NOS. 55-61, 69-71 or 81

(SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 69, SEQ ID NO: 70, SEQ ID NO: 71 or SEQ ID NO: 81). In some embodiments, the fusion protein of the present disclosure may comprise or consist of a functional analogue, derivative or a fragment of any one sequence listed in Table 9, i.e., any of SEQ ID NOS: 55-61 (SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 69, SEQ ID NO: 70, SEQ ID NO: 71 or SEQ ID NO: 81).

In one embodiment, the fusion protein comprises or consists of TAT-GG-SUMO1-hFXN having an amino acid sequence as set forth in SEQ ID NO: 55. In one embodiment, the fusion protein comprises or consists of TAT-SS_SUMO-hFXN having an amino acid sequence as set forth in SEQ ID NO: 81. In one embodiment, the fusion protein comprises or consists of TAT-GG-Ubiquitin-hFXN having an amino acid sequence as set forth in SEQ ID NO: 56. In one embodiments, the fusion protein comprises or consists of TAT-GG-DEVD-hFXN having an amino acid sequence as set forth in SEQ ID NO: 57. In one embodiment, the fusion protein comprises or consists of TAT-GG-EPLFAERK-hFXN having an amino acid sequence as set forth in SEQ ID NO: 58. In one embodiment, the fusion protein comprises or consists of TAT-GG-LLVY-hFXN having an amino acid sequence as set forth in SEQ ID NO: 59. In one embodiment, the fusion protein comprises or consists of TAT-GG-hFXN-NES1 having an amino acid sequence as set forth in SEQ ID NO: 60. In one embodiment, the fusion protein comprises or consists of TAT-GG-hFXN-NES2 having an amino acid sequence as set forth in SEQ ID NO: 61. In one embodiment, the fusion protein comprises or consists of TAT-GG-Ubiquitin-PARKIN having an amino acid sequence as set forth in SEQ ID NO: 69. In one embodiment, the fusion protein comprises or consists of TAT-GG-EPLFAERK-PARKIN having an amino acid sequence as set forth in SEQ ID NO: 70. In one embodiment, the fusion protein comprises or consists of TAT-PARKIN-NES1 having an amino acid sequence as set forth in SEQ ID NO: 71.

In some embodiments, the fusion protein provided by the present disclosure comprises: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, the fusion protein provided by the present disclosure comprises: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11 or SEQ ID NO: 83); and 3) any TES as described herein.

For example, the fusion protein of the present disclosure may comprise 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to Ubiquitin (SEQ ID NO: 18).

For example, the fusion protein of the present disclosure may comprise 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

For example, the fusion protein of the present disclosure may comprise 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, the fusion protein provided by the present disclosure comprises: 1) an amino acid sequence having at least 85%, at least 90%, at least 95%, or at least 99% sequence identity to PARKIN (SEQ ID NO: 7) as protein of interest; 2) any CPP as described herein; and 3) any TES as described herein.

In some embodiments, the fusion protein provided by the present disclosure comprises: 1) an amino acid sequence having at least 85%, at least 90%, at least 95%, or at least 99% sequence identity to PARKIN (also referred to herein as "PARK2 protein", SEQ ID NO: 7) as protein of interest; 2) an amino acid sequence having at least 85%, at least 90%, at least 95% or at least 99% to TAT-HIV (SEQ ID NO: 11); and 3) any TES as described herein.

For example, the fusion protein of the present disclosure may comprise 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to Ubiquitin (SEQ ID NO: 18).

For example, the fusion protein of the present disclosure may comprise 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to a calpain cleavage domain of SEQ ID NO: 20.

For example, the fusion protein of the present disclosure may comprise 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11 or SEQ ID NO: 83); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, one or more of the fusion proteins provided by the present disclosure may also include a post-translational modification characteristic of eukaryotic cells, e.g., mammalian cells, e.g., human cells. In some embodiments, the fusion protein may comprise one or more (e.g., 2, 3, 4, 5, 6, 7, 8, 9, 10, or more) post-translational modifications, such as glycosylation, phosphorylation, acetylation, or combinations thereof. In some embodiments, glycosylation may include the addition of a glycosyl group to arginine, asparagine, cysteine, hydroxylysine, serine, threonine, tyrosine, or tryptophan. The glycosylation may comprise, e.g., O-linked glycosylation or N-linked glycosylation. Levels of glycosylation of a fusion protein of the disclosure may be assessed in vitro using SDS-PAGE gels and a Western Blot using a modification of Periodic acid-Schiff (PAS) methods. Cellular localization of a fusion protein that may comprise glycosylation may be accomplished by utilizing lectin fluorescent conjugates known in the art. Phosphorylation that may be present in a fusion protein of the present disclosure may be assessed by Western blot using phospho-specific antibodies.

Post-translation modifications that may be present in fusion protein of the present disclosure may also include conjugation to a hydrophobic group (e.g., myristoylation, palmitoylation, isoprenylation, prenylation, or glypiation), conjugation to a cofactor (e.g., lipoylation, flavin moiety (e.g., FMN or FAD), heme C attachment, phosphopantetheinylation, or retinylidene Schiff base formation), diphthamide formation, ethanolamine phosphoglycerol attachment, hypusine formation, acylation (e.g. O-acylation, N-acylation, or S-acylation), formylation, acetylation, alkylation (e.g., methylation or ethylation), amidation, butyrylation, gamma-carboxylation, malonylation, hydroxylation, iodination, nucleotide addition such as ADP-ribosylation, oxidation, phosphate ester (O-linked) or phosphoramidate (N-linked) formation, (e.g., phosphorylation or adenylylation), propionylation, pyroglutamate formation, S-glutathionylation, S-nitrosylation, succinylation, sulfation, ISGylation, SUMOylation, ubiquitination, neddylation, or a chemical modification of an amino acid (e.g., citrullination, deamidation, eliminylation, or carbamylation), formation of a disulfide bridge, racemization (e.g., of proline, serine, alanine, or methionine).

Nucleic Acids

The present disclosure also provides a nucleic acid encoding a fusion protein as described above, or any variants thereof.

As used herein, the term "nucleic acid(s)" is interchangeable with the term "polynucleotide(s)" and generally refers to any polyribonucleotide or poly-deoxyribonucleotide, which may be unmodified RNA or DNA or modified RNA or DNA or any combination thereof. The term "nucleic acid(s)" include, without limitation, single- and double-stranded nucleic acids.

The present disclosure provides fusion proteins as described herein, or variants thereof. Variants provided by the present disclosure may include conservatively substituted variants that apply to both amino acid and nucleic acid sequences. With respect to nucleic acid sequences, conservatively modified variants refer to those nucleic acids which encode identical or essentially identical amino acid sequences. Specifically, degenerate codon substitutions may be achieved by generating sequences in which the third position of one or more selected (or all) codons is substituted with mixed base and/or deoxyinosine residues. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence described herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to encode a functionally identical polypeptide. Accordingly, each silent variation of a nucleic acid which encodes a polypeptide is implicit in each described sequence.

With regard to conservative substitution of amino acid sequences, an ordinary artisan may recognize that individual substitution(s), deletion(s) or addition(s) to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following groups each contain amino acids that are conservative substitutions for one another:
1) alanine (A), glycine (G);
2) serine (S), threonine (T);
3) aspartic acid (D), glutamic acid (E);
4) asparagine (N), glutamine (Q);
5) cysteine (C), methionine (M);
6) arginine (R), lysine (K), histidine (H);
7) isoleucine (I), leucine (L), valine (V); and
8) phenylalanine (F), tyrosine (Y), tryptophan (W).

Listed in Table 10 below are certain exemplary nucleic acids encoding fusion proteins of the present disclosure.

TABLE 10

Nucleic acids encoding fusion proteins of the disclosure.

| SEQ ID NO. | Fusion Protein | Sequence |
|---|---|---|
| 62 | TAT-GG-SUMO1-hFXN | ATGTACGGCCGCAAGAAGCGGAGACAGAGGCGCCGGGGAGGA<br>ATGTCCGACCAGGAGGCCAAGCCCTCTACCGAGGACCTGGGCG<br>ATAAGAAGGAGGGCGAGTACATCAAGCTGAAAGTGATCGGCC<br>AGGATAGCTCCGAGATCCACTTCAAGGTGAAGATGACCACACA<br>CCTGAAGAAGCTGAAGGAGTCTTATTGCCAGCGGCAGGGCGTG<br>CCAATGAACAGCCTGAGATTCCTGTTTGAGGGCCAGAGGATCG<br>CCGACAATCACACCCCCAAGGAGCTGGGCATGGAGGAGGAGG<br>ATGTGATCGAGGTGTATCAGGAGCAGACCGGCGGCATGTGGAC<br>ACTGGGCAGAAGGGCAGTGGCAGGCCTGCTGGCATCCCCATCT |

TABLE 10-continued

Nucleic acids encoding fusion proteins of the disclosure.

| SEQ ID NO. | Fusion Protein | Sequence |
|---|---|---|
| | | CCTGCACAGGCACAGACCCTGACACGCGTGCCACGGCCCGCAG
AGCTGGCACCACTGTGCGGCCGGAGAGGCCTGAGGACAGACAT
CGATGCCACCTGTACACCTAGAAGGGCCTCTAGCAACCAGCGG
GGCCTGAACCAGATCTGGAATGTGAAGAAGCAGTCCGTGTACC
TGATGAATCTGAGAAAGAGCGGCACCCTGGGACACCCTGGCTC
CCTGGACGAGACAACATATGAGAGGCTGGCCGAGGAGACACTG
GATTCTCTGGCCGAGTTCTTTGAGGACCTGGCCGATAAGCCATA
CACCTTCGAGGACTATGATGTGAGCTTTGGCTCCGGCGTGCTGA
CAGTGAAGCTGGGAGGCGACCTGGGCACCTACGTGATCAACAA
GCAGACACCTAATAAGCAGATCTGGCTGTCCTCTCCTAGCTCCG
GCCCAAAGCGGTACGACTGGACCGGCAAGAACTGGGTGTATTC
TCACGATGGCGTGAGCCTGCACGAGCTGCTGGCAGCAGAGCTG
ACCAAGGCCCTGAAGACAAAGCTGGACCTGTCTAGCCTGGCCT
ATAGCGGCAAGGATGCCTGA |
| 63 | TAT-GG-
Ubiquitin-hFXN | ATGTACGGCCGGAAGAAGCGGAGACAGAGGCGCCGGGGAGGA
ATGCAGATCTTCGTGAAGACCCTGACAGGCAAGACCATCACAC
TGGAGGTGGAGCCCTCTGACACCATCGAGAACGTGAAGGCCAA
GATCCAGGACAAGGAGGGCATCCCCCCTGATCAGCAGCGCCTG
ATCTTTGCAGGCAAGCAGCTGGAGGACGGACGGACCCTGTCTG
ATTATAATATCCAGAAGGAGAGCACACTGCACCTGGTGCTGAG
GCTGAGGGGAGGAATGTGGACCCTGGGCAGAAGGGCAGTGGC
AGGCCTGCTGGCCTCTCCAAGCCCAGCACAGGCACAGACCCTG
ACAAGAGTGCCTAGGCCAGCAGAGCTGGCACCACTGTGCGGCC
GGAGAGGCCTGAGAACAGACATCGATGCCACCTGTACACCCAG
AAGGGCCAGCTCCAACCAGAGGGGCCTGAACCAGATCTGGAAT
GTGAAGAAGCAGAGCGTGTACCTGATGAATCTGAGGAAGTCCG
GCACCCTGGGACACCCTGGCTCTCTGGACGAGACAACATATGA
GCGGCTGGCCGAGGAGACACTGGATTCCCTGGCCGAGTTCTTT
GAGGACCTGGCCGATAAGCCATACACCTTCGAGGACTATGACG
TGAGCTTCGGCTCTGGCGTGCTGACAGTGAAGCTGGGCGGCGA
TCTGGGCACCTACGTGATCAACAAGCAGACACCTAATAAGCAG
ATCTGGCTGTCTAGCCCCTCCTCTGGCCCTAAGAGATACGACTG
GACCGGCAAGAACTGGGTGTATAGCCACGATGGCGTGTCCCTG
CACGAGCTGCTGGCAGCAGAGCTGACCAAGGCCCTGAAGACAA
AGCTGGACCTGAGCTCCCTGGCCTATTCCGGCAAGGATGCCTG
A |
| 64 | TAT-GG-DEVD-
hFXN | ATGTACGGCAGAAAGAAGAGGCGGCAGAGACGCAGGGGAGGC
GACGAGGTGGATATGTGGACCCTGGGCGGAGAGCAGTGGCAG
GACTGCTGGCCTCTCCCAGCCCTGCCCAGGCCCAGACCCTGACA
CGCGTGCCAAGGCCAGCAGAGCTGGCACCACTGTGCGGCCGCA
GGGGCCTGCGGACAGACATCGATGCCACCTGTACACCTCGGAG
AGCCAGCTCCAACCAGAGAGGCCTGAACCAGATCTGGAATGTG
AAGAAGCAGTCCGTGTACCTGATGAATCTGAGGAAGTCTGGCA
CCCTGGGACACCCAGGCAGCCTGGACGAGACCACATACGAGAG
GCTGGCCGAGGAGACACTGGATTCTCTGGCCGAGTTCTTTGAG
GACCTGGCCGATAAGCCCTACACCTTCGAGGACTACGACGTGA
GCTTCGGCTCTGGCGTGCTGACAGTGAAGCTGGGCGGCGACCT
GGGCACCTACGTGATCAACAAGCAGACACCTAATAAGCAGATC
TGGCTGTCTAGCCCTTCCTCTGGCCCAAAGAGGTACGACTGGAC
CGGCAAGAACTGGGTGTACAGCCACGATGGCGTGTCCCTGCAC
GAGCTGCTGGCAGCAGAGCTGACCAAGGCCCTGAAGACAAAGC
TGGACCTGAGCTCCCTGGCCTACAGCGGCAAGGATGCCTGA |
| 65 | TAT-GG-
EPLFAERK-
hFXN | ATGTATGGAAGGAAGAAGAGACGGCAGAGACGGAGAGGAGGC
GAGCCCCTGTTTGCTGAGCGGAAGATGTGGACCCTGGGAAGGC
GGGCAGTGGCAGGCCTGCTGGCAAGCCCATCCCCTGCACAGGC
ACAGACCCTGACAAGGGTGCCACGGCCCGCAGAGCTGGCACCA
CTGTGCGGCAGGCGGGGCCTGAGAACCGACATCGATGCCACCT
GTACACCTAGAAGGGCCAGCTCCAACCAGAGGGGCCTGAACCA
GATCTGGAATGTGAAGAAGCAGAGCGTGTACCTGATGAATCTG
AGGAAGAGCGGCACCCTGGGACACCCAGGCTCCCTGGACGAGA
CAACATACGAGAGGCTGGCCGAGGAGACACTGGATTCCCTGGC
CGAGTTCTTTGAGGACCTGGCCGATAAGCCCTACACCTTCGAGG
ACTACGACGTGAGCTTCGGCAGCGGCGTGCTGACAGTGAAGCT
GGGGAGGCGACCTGGGCACCTACGTGATCAACAAGCAGACACCT
AATAAGCAGATCTGGCTGTCTAGCCCTTCCTCTGGCCCAAAGCG
GTACGACTGGACCGGCAAGAACTGGGTGTACTCCCACGATGGC
GTGTCTCTGCACGAGCTGCTGGCAGCAGAGCTGACAAAAGCAC
TGAAAACAAAACTGGACCTGTCATCACTGGCATACTCTGGAAA
GGACGCATAA |
| 66 | TAT-GG-LLVY-
hFXN | ATGTACGGCAGAAAGAAGAGGCGGCAGAGACGCAGGGGAGGA
CTGCTGGTGTACATGTGGACCCTGGGCCGGAGAGCAGTGGCAG
GACTGCTGGCCTCTCCCAGCCCTGCCCAGGCCCAGACCCTGACA |

TABLE 10-continued

Nucleic acids encoding fusion proteins of the disclosure.

| SEQ ID NO. | Fusion Protein | Sequence |
|---|---|---|
| | | CGCGTGCCAAGGCCAGCAGAGCTGGCACCACTGTGCGGCCGCA
GGGGCCTGCGGACAGACATCGATGCCACCTGTACACCTCGGAG
AGCCAGCTCCAACCAGAGAGGCCTGAACCAGATCTGGAATGTG
AAGAAGCAGTCCGTGTACCTGATGAATCTGAGGAAGTCTGGCA
CCCTGGGACACCCAGGCAGCCTGGACGAGACCACATACGAGAG
GCTGGCCGAGGAGACACTGGATTCTCTGGCCGAGTTCTTTGAG
GACCTGGCCGATAAGCCCTACACCTTCGAGGACTACGACGTGA
GCTTCGGCTCTGGCGTGCTGACAGTGAAGCTGGGCGGCGACCT
GGGCACCTACGTGATCAACAAGCAGACACCTAATAAGCAGATC
TGGCTGTCTAGCCCTTCCTCTGGCCCAAAGAGGTACGACTGGAC
CGGCAAGAACTGGGTGTACAGCCACGATGGCGTGTCCCTGCAC
GAGCTGCTGGCAGCAGAGCTGACCAAGGCCCTGAAGACAAAGC
TGGACCTGAGCTCCCTGGCCTACAGCGGCAAGGATGCCTGA |
| 67 | TAT-GG-hFXN-NES1 | ATGTATGGAAGGAAGAAGAGACGGCAGAGACGGAGAGGAGGC
GAGCCCCTGTTTGCTGAGCGGAAGATGTGGACCCTGGGAAGGC
GGGCAGTGGCAGGCCTGCTGGCAAGCCCATCCCCTGCACAGGC
ACAGACCCTGACAAGGGTGCCACGGCCCGCAGAGCTGGCACCA
CTGTGCGGCAGGCGGGGCCTGAGAACCGACATCGATGCCACCT
GTACACCTAGAAGGGCCAGCTCCAACCAGAGGGGCCTGAACCA
GATCTGGAATGTGAAGAAGCAGAGCGTGTACCTGATGAATCTG
AGGAAGAGCGGCACCCTGGGACACCCAGGCTCCCTGGACGAGA
CAACATACGAGAGGCTGGCCGAGGAGACACTGGATTCCCTGGC
CGAGTTCTTTGAGGACCTGGCCGATAAGCCCTACACCTTCGAGG
ACTACGACGTGAGCTTCGGCAGCGGCGTGCTGACAGTGAAGCT
GGGGAGGCGACCTGGGCACCTACGTGATCAACAAGCAGACACCT
AATAAGCAGATCTGGCTGTCTAGCCCTTCCTCTGGCCCAAAGCG
GTACGACTGGACCGGCAAGAACTGGGTGTACTCCCACGATGGC
GTGTCTCTGCACGAGCTGCTGGCAGCAGAGCTGACAAAAGCAC
TGAAAACAAAACTGGACCTGTCATCACTGGCATACTCTGGAAA
GGACGCATAA |
| 68 | TAT-GG-hFXN-NES2 | ATGTACGGCAGAAAGAAGAGGCGGCAGAGACGCAGGGGAG
GAATGTGGACCCTGGGCCGGAGAGCAGTGGCAGGACTGCTGGC
CTCTCCCAGCCCTGCCCAGGCCCAGACCCTGACACGCGTGCCA
AGGCCAGCAGAGCTGGCACCACTGTGCGGCCGCAGGGGCCTGC
GGACAGACATCGATGCCACCTGTACACCTCGGAGAGCCAGCTC
CAACCAGAGAGGCCTGAACCAGATCTGGAATGTGAAGAAGCA
GTCCGTGTACCTGATGAATCTGAGGAAGTCTGGCACCCTGGGA
CACCCAGGCAGCCTGGACGAGACCACATACGAGAGGCTGGCCG
AGGAGACACTGGATTCTCTGGCCGAGTTCTTTGAGGACCTGGCC
GATAAGCCCTACACCTTCGAGGACTACGACGTGAGCTTCGGCT
CTGGCGTGCTGACAGTGAAGCTGGGCGGCGACCTGGGCACCTA
CGTGATCAACAAGCAGACACCTAATAAGCAGATCTGGCTGTCT
AGCCCTTCCTCTGGCCCAAAGAGGTACGACTGGACCGGCAAGA
ACTGGGTGTACAGCCACGATGGCGTGTCCCTGCACGAGCTGCT
GGCAGCAGAGCTGACCAAGGCCCTGAAGACAAAGCTGGACCTG
AGCTCCCTGGCCTACAGCGGCAAGGATGCCCTGCAGAAGAAGC
TGGAGGAGCTGGAGCTGTGA |
| 86 | TAT-GG-Ubiquitin-PARKIN | ATGTACGGCCGGAAGAAGCGGCGGCAGCGTCGGAGAGGCGGC
ATGCAGATCTTCGTGAAAACATTAACCGGCAAGACCATCACCC
TGGAAGTGGAACCTAGCGACACCATCGAGAACGTGAAGGCCAA
GATCCAGGACAAGGAAGGCATCCCTCCTGATCAGCAGCGACTG
ATTTTCGCTGGAAAGCAGCTGGAAGATGGCAGAACCCTGAGCG
ACTACAACATCCAGAAGGAGAGCACACTGCACCTGGTGCTGAG
GCTGCGGGGCGGCATGATCGTGTTCGTGAGATTCAACAGCAGC
CACGGCTTCCCCGTCGAGGTGGATTCTGACACCAGCATCTTTCA
ACTGAAGGAAGTGGTGGCAAAGAGACAGGGCGTGCCCGCCGAT
CAACTGCGGGTAATCTTCGCCGGAAAAGAGCTGAGAAATGACT
GGACAGTGCAGAACTGCGACCTGGATCAGCAAAGCATTGTGCA
CATCGTGCAGCGGCCTTGGCGGAAAGGCCAGGAGATGAACGCC
ACCGGCGGAGATGATCCTAGAAATGCTGCTGGCGGCTGCGAGC
GGGAACCCCAGAGCCTGACCAGAGTGGACCTGTCCAGCTCTGT
GCTACCAGGCGACAGCGTGGGCCTGGCCGTGATCCTGCACACA
GATTCCAGAAAGGACAGCCCACCTGCCGGCAGCCCGGCCGGAA
GGTCCATCTACAACTCCTTCTACGTGTACTGCAAGGGCCCTTGC
CAGAGAGTGCAACCTGGCAAACTGAGAGTTCAGTGCTCTACAT
GTAGACAAGCCACACTGACACTGACCCAGGGCCCCAGCTGTTG
GGACGACGTGCTGATCCCCAACAGAATGAGCGGCGAGTGCCAA
AGCCCCCACTGCCCTGGCACCAGCAGCGCCGAGTTCTTCTTTAAGTG
TGGAGCTCACCCCACCTCCGACAAGGAAACCAGCGTGGCCCTG
CATCTGATCGCCACCAACAGCAGAAACATCACCTGTATCACAT
GCACCGACGTCAGAAGCCCTGTGCTTGTGTTTCAGTGTAATAGC
CGGCACGTGATCTGCCTGGACTGCTTCCACCTGTACTGCGTGAC
CAGACTGAACGACAGACAGTTTGTGCACGACCCTCAGCTGGGC TABLE 10-continued Nucleic acids encoding fusion proteins of the disclosure.

| SEQ ID NO. | Fusion Protein | Sequence |
| --- | --- | --- |
| | | TACTCGCTGCCTTGTGTGGCCGGCTGTCCTAACTCTCTGATCAA
GGAACTGCATCACTTCAGAATCCTGGGCGAGGAACAGTACAAC
CGGTACCAGCAGTACGGCGCCGAGGAATGCGTGCTGCAGATGG
GCGGAGTGCTGTGCCCTAGACCCGGATGTGGAGCCGGACTGCT
GCCTGAGCCCGACCAGCGGAAAGTGACCTGCGAGGGAGGCAAC
GGCCTCGGCTGCGGTTTCGCCTTCTGCAGAGAATGTAAAGAAG
CTTACCACGAGGGGAGTGTTCTGCCGTGTTCGAGGCCTCTGGC
ACAACCACCCAGGCTTATAGAGTGGACGAGAGAGCCGCCGAGC
AGGCCAGATGGGAGGCCGCCAGCAAGGAGACAATCAAGAAGA
CCACAAAGCCTTGCCCACGCTGCCACGTGCCTGTGGAAAAGAA
CGGCGGCTGTATGCACATGAAGTGCCCTCAGCCTCAGTGCAGA
CTGGAATGGTGCTGGAACTGCGGCTGCGAGTGGAATAGAGTCT
GCATGGGCGATCACTGGTTCGACGTT |
| 87 | TAT-GG-
EPLFAERK-
PARKIN | ATGTACGGCAGAAAGAAAAGACGCCAGAGACGGCGGGGCGGC
GAGCCTCTGTTCGCCGAAAGAAAGATGATTGTGTTTGTCAGATT
TAATTCTTCACACGGATTTCCCGTCGAAGTGGATTCAGACACCA
GTATTTTTCAGCTTAAGGAGGTCGTAGCCAAGCGGCAGGGCGT
GCCCGCCGACCAATTGAGAGTGATCTTTGCTGGAAAAGAATTG
AGGAATGATTGGACTGTCCAGAACTGCGATTTGGATCAGCAGT
CTATCGTGCATATAGTTCAGCGACCATGGCGCAAGGGACAGGA
GATGAATGCAACCGGAGGCGACGACCCACGGAATGCAGCCGG
AGGGTGTGAGAGAGAGCCCCAGAGTTTGACTCGGGTCGATCTG
AGCTCTAGCGTACTCCCAGGGGATTCAGTGGGACTCGCAGTTAT
CCTGCATACTGACTCCAGAAAGGACTCACCGCCCGCCGGGAGT
CCGGCCGGAAGATCAATTTATAATAGCTTTTACGTTTATTGTAA
GGGACCCTGTCAGAGAGTACAGCCCGGCAAGTTGAGGGTGCAA
TGTAGTACCTGCCGCCAGGCCACGCTGACACTCACACAGGGAC
CATCCTGTTGGGACGACGTGCTTATCCCCAACAGGATGTCCGGT
GAGTGTCAATCCCCTCACTGCCCTGGGACAAGCGCCGAATTCTT
CTTCAAATGTGGTGCCCACCCCACATCCGACAAGGAGACTTCCG
TCGCCCTGCACCTGATCGCAACTAACAGCCGGAATATCACGTGC
ATCACCTGCACGGATGTGCGGTCCCCTGTGCTGGTCTTTCAGTG
TAATTCTCGGCACGTGATCTGCCTTGACTGCTTCCACCTGTACT
GCGTTACACGACTGAACGACAGGCAGTTCGTGCATGACCCTCA
GCTTGGGTACTCTCTTCCATGTGTTGCCGGGTGTCCTAACTCATT
GATCAAGGAGCTCCACCACTTCAGGATTTTGGGGGAGGAGCAA
TATAACCGATACCAGCAGTACGGCGCCGAGGAGTGTGTGCTGC
AGATGGGAGGAGTACTTTGTCCACGCCCGGGATGTGGAGCAGG
CCTGCTCCCAGAACCAGATCAACGCAAGGTGACGTGTGAGGGA
GGAAATGGGCTCGGCTGCGGGTTCGCCTTTTGCAGGGAGTGTA
AGGAGGCCTATCATGAAGGTGAATGCTCCGCTGTGTTCGAGGC
CTCTGGTACTACCACTCAGGCCTATAGGGTCGACGAGAGAGCT
GCTGAGCAAGCCCGATGGGAGGCTGCAAGCAAAGAAACCATCA
AGAAAACTACGAAGCCATGCCCTCGCTGCCATGTGCCCGTCGA
GAAGAACGGTGGCTGCATGCACATGAAGTGTCCACAGCCCCAG
TGCCGGTTGGAATGGTGTTGGAATTGCGGATGCGAATGGAACC
GCGTCTGCATGGGCGATCACTGGTTCGACGTT |
| 88 | TAT-GG-
PARKIN-NES1 | ATGTACGGAAGAAAAAAGCGGAGACAGAGAAGAAGAGGCGGG
ATGATCGTGTTCGTGCGGTTCAACAGCAGCCACGGCTTTCCAGT
CGAGGTGGACTCTGACACCTCCATCTTCCAGCTGAAGGAGGTG
GTGGCCAAGCGGCAGGGCGTGCCCTGCCGATCAGCTGAGGGTGA
TCTTTGCCGGGAAGGAGCTGCGGAATGACTGGACCGTACAGAA
CTGCGACCTGGACCAGCAATCTATCGTGCACATCGTGCAGCGA
CCTTGGCGGAAGGGCCAGGAGATGAACGCTACAGGCGGCGAC
GACCCTAGAAATGCCGCCGGCGGATGTGAACGGGAACCTCAAT
CTCTGACACGGGTGGATCTGAGCTCTAGCGTGCTCCCCGGAGAC
TCTGTGGGCCTGGCCGTGATCCTGCACACCGACAGCAGGAAGG
ACAGCCCCCCGCCGGAAGTCCTGCCGGCAGATCCATCTACAA
CTCTTTCTACGTGTACTGCAAAGGCCCTTGCCAGCGCGTGCAGC
CTGGCAAGCTGAGAGTGCAATGTAGCACCTGTAGACAGGCCAC
ACTGCACACTGACCCAGGGACCTAGCTGCTGGGATGATGTGCTG
ATTCCTAACAGAATGAGCGGCGAGTGCCAGAGCCCTCACTGCC
CCGGCACAAGCGCCGAATTCTTCTTCAAGTGCGGCGCCCACCCT
ACCAGCGACAAGGAGACAAGCGTGGCCCTGCATCTAATCGCCA
CTAACAGCAGAAACATCACCTGTATCACCTGCACCGACGTCAG
AAGCCCAGTGCTCGTGTTTCAGTGCAACAGCCGGCACGTGATCT
GCCTGGATTGCTTCCACCTGTACTGTGTCACCAGACTGAACGAT
AGACAGTTCGTGCATGATCCACAGCTGGGCTACAGCCTGCCCTG
CGTTGCCGGCTGTCCTAACTCCCTGATCAAGGAACTGCACCACT
TCCGGATCCTGGGCGAGGAACAGTACAACCGCTACCAGCAGTA
CGGCGCCGAGGAATGCGTGCTGCAGATGGGAGGAGTGCTGTGC
CCCAGACCTGGATGCGGTGCTGGACTGCTGCCTGAGCCCGACC
AAAGAAAGGTGACCTGCGAGGGCGGCAACGGCCTGGGCTGTGG
CTTCGCCTTCTGCAGAGAGTGCAAGGAAGCCTATCACGAGGGC |

TABLE 10-continued

Nucleic acids encoding fusion proteins of the disclosure.

| SEQ ID NO. | Fusion Protein | Sequence |
|---|---|---|
| | | GAATGCAGCGCCGTGTTTGAGGCTTCTGGCACCACCACCCAGG<br>CTTATAGAGTCGACGAGCGGGCCGCTGAGCAGGCCAGATGGGA<br>GGCTGCCAGCAAGGAAACCATCAAGAAAACAACAAAGCCCTGC<br>CCTAGATGTCACGTGCCAGTTGAGAAGAACGGCGGCTGCATGC<br>ACATGAAATGTCCTCAGCCTCAGTGCAGACTGGAATGGTGCTG<br>GAATTGCGGCTGTGAATGGAATCGGGTGTGCATGGGCGACCAC<br>TGGTTCGATGTGCTGGCCCTGAAACTGGCAGGCCTGGACCTG |

In some embodiments, nucleic acid sequences encoding fusion proteins of the present disclosure comprises any one sequence as listed in Table 10, i.e., any of SEQ ID NOS: 62-68 (SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 86, SEQ ID NO: 87 or SEQ ID NO: 88). In some embodiments, a nucleic acid sequence encoding a fusion protein provided by the present disclosure comprises a sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any of SEQ ID NOS. 62-68 (SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 86, SEQ ID NO: 87 or SEQ ID NO: 88).

In one embodiment, the nucleic acid sequence encoding a fusion protein TAT-GG-SUMO1-hFXN has a sequence as set forth in SEQ ID NO: 62. In one embodiment, the nucleic acid sequence encoding a fusion protein TAT-GG-Ubiquitin-hFXN has a sequence as set forth in SEQ ID NO: 63. In one embodiments, the nucleic acid sequence encoding a fusion protein TAT-GG-DEVD-hFXN has a sequence as set forth in SEQ ID NO: 64. In one embodiment, the nucleic acid sequence encoding a fusion protein TAT-GG-EPLFAERK-hFXN has a sequence as set forth in SEQ ID NO: 65. In one embodiment, the nucleic acid sequence encoding a fusion protein TAT-GG-LLVY-hFXN has a sequence as set forth in SEQ ID NO: 66. In one embodiment, the nucleic acid sequence encoding a fusion protein TAT-GG-hFXN-NES1 has a sequence as set forth in SEQ ID NO: 67. In one embodiment, the nucleic acid sequence encoding a fusion protein TAT-GG-hFXN-NES2 has a sequence as set forth in SEQ ID NO: 68. In one embodiment, the nucleic acid sequence encoding a fusion protein TAT-GG-Ubiquitin-PARKIN has a sequence as set forth in SEQ ID NO: 86. In one embodiment, the nucleic acid sequence encoding a fusion protein TAT-GG-EPLFAERK-PARKIN has a sequence as set forth in SEQ ID NO: 87. In one embodiment, the nucleic acid sequence encoding a fusion protein TAT-GG-PARKIN-NES1 has a sequence as set forth in SEQ ID NO: 88.

The present disclosure also provides an expression vector for producing a fusion protein as defined herein in a cell, e.g., a mammalian cell, a bacterial cell or a fungal cell. The expression vector of the present disclosure may comprise a nucleic acid encoding a fusion protein of the present disclosure, e.g., any one of SEQ ID NOS. 62-68. By way of example, the expression vector may be a retroviral vector, a DNA vector, a plasmid, an RNA vector, an adenoviral vector, an adenovirus associated vector, a lentiviral vector, a phagemid, a baculovirus, or any combination thereof.

Vectors

Vectors may enable the integration of DNA fragments or nucleic acid sequences into the genome of the host or enable expression of genetic elements that are not integrated. Vectors are typically self-replicating DNA or RNA constructs containing the desired nucleic acid sequences, and operably linked genetic control elements that are recognized in a suitable host cell and effect the translation of the desired spacers. Generally, the genetic control elements may include a prokaryotic promoter system or a eukaryotic promoter expression control system. Such system typically includes a transcriptional promoter and transcription enhancers to elevate the level of RNA expression. Vectors usually contain an origin of replication that allows the vector to replicate independently of the host cell. Accordingly, the term control and regulatory elements include promoters, terminators and other expression control elements. Such regulatory elements are described in the art and known to the skilled artisan. For instance, any of a wide variety of expression control sequences that control the expression of a DNA sequence when operatively linked to it may be used in these vectors to express DNA sequences encoding any desired fusion protein as described herein.

A vector may additionally include appropriate restriction sites, antibiotic resistance or other markers for selection of vector-containing cells. Plasmids are the most commonly used form of vector but other forms of vectors which serve an equivalent function, and which are, or become, known in the art are suitable for use herein.

A vector may also be referred to as a construct, or as recombinant nucleic acid. As referred to herein, the term "recombinant DNA", "recombinant nucleic acid sequence" or "recombinant gene" refers to a nucleic acid comprising an open reading frame (ORF) encoding a fusion protein as described herein. A construct comprising an ORF encoding a fusion protein as described herein may optionally further comprise additional elements such as promoters, regulatory and control elements, translation, expression and other signals, operably linked to the nucleic acid sequence described herein. The term "operatively-linked", as used herein, is intended to mean attached in a manner which allows for transgene transcription. The term "encoding", as used herein, is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell.

According to some embodiments, recombinant DNA encoding a fusion protein of the present disclosure may be cloned into a vector, e.g., lentiviral vector plasmid capable of integration into a cell. According to some embodiments, recombinant DNA encoding the one or more fusion proteins may be cloned into a plasmid DNA construct encoding a selectable trait, such as an antibiotic resistance gene. According to some embodiments, recombinant DNA encoding the fusion proteins may be cloned into a plasmid construct that is adapted to stably express a fusion protein in a cell.

Conjugate

The present disclosure also provides a conjugate for intracellular delivery of a protein of interest to a non-nuclear organelle. The conjugate of the disclosure may comprise a fusion protein as defined in the disclosure, and at least one of a label, for example a radioactive, fluorescent, chromophore, enzymatic, peptide or protein label, a small molecule, or a polymer (such as polyethylene glycol, PEG, for example).

Cell

The present disclosure also provides a cell comprising any one of a fusion protein, a nucleic acid, a vector, a conjugate, or any combination thereof, as described herein. In some aspects, the cell may be a stem cell or an iPS cell. In other aspects, a cell may be selected from the group consisting of a muscle progenitor cell, a neuron progenitor cell, a bone marrow stem cell, a bacterial cell, or a yeast cell. By way of example, a cell may be any one of a muscle or muscle progenitor cell, a fibroblast, an epidermal cell, a cardiac cell, a stem cell, an embryonic stem cell, a pluripotent cell, a neuron, a bone marrow stem cell, and including yeast or bacteria cell lines.

In certain embodiments, the cell comprising a fusion protein, a nucleic acid, a vector, a conjugate, or any combination thereof, may be selected from the group consisting of a long term hematopoietic stem cell, a short term hematopoietic stem cell, a multipotent progenitor cell, a lineage restricted progenitor cell, a lymphoid progenitor cell, a myeloid progenitor cell, a common myeloid progenitor cell, an erythroid progenitor cell, a megakaryocyte erythroid progenitor cell, a retinal cell, a photoreceptor cell, a rod cell, a cone cell, a retinal pigmented epithelium cell, a trabecular meshwork cell, a cochlear hair cell, an outer hair cell, an inner hair cell, a pulmonary epithelial cell, a bronchial epithelial cell, an alveolar epithelial cell, a pulmonary epithelial progenitor cell, a striated muscle cell, a cardiac muscle cell, a muscle satellite cell, a neuron, a neuronal stem cell, a mesenchymal stem cell, an induced pluripotent stem (iPS) cell, an embryonic stem cell, a fibroblast, a monocyte-derived macrophage or dendritic cell, a megakaryocyte, a neutrophil, an eosinophil, a basophil, a mast cell, a cell, a B cell, e.g., a progenitor B cell, a Pre B cell, a Pro B cell, a memory B cell, a plasma B cell, a gastrointestinal epithelial cell, a biliary epithelial cell, a pancreatic ductal epithelial cell, an intestinal stem cell, a hepatocyte, a liver stellate cell, a Kupffer cell, an osteoblast, an osteoclast, an adipocyte, a preadipocyte, a pancreatic islet cell (e.g., a beta cell, an alpha cell, a delta cell), a pancreatic exocrine cell, a Schwann cell and an oligodendrocyte.

In some embodiments, the cell comprising the fusion protein is a dividing cell. In other embodiments, the cell comprising the fusion protein is a non-dividing cell.

In some embodiments, the cell comprising the fusion protein of the present disclosure may be in a subject, such as a subject who is administered the fusion protein, e.g., for treating a pathological condition, e.g., a genetic disorder. In some examples, the pathological condition may be a non-nuclear organelle associated disorder. In one specific example, the pathological condition is Friedrich's Ataxia.

In one specific example, the subject may be administered a fusion protein of the present disclosure, e.g., any of SEQ ID NOS. 55-61, for treating Friedrich's Ataxia. In other examples, the subject may be administered a fusion protein of the present disclosure for treating a mitochondrial disorder, e.g., mitochondrial myopathy, diabetes mellitus and deafness, Leber's hereditary optic neuropathy, neuropathy, retinitis pigmentosa, ptosis (NARP), myoneurogenic gastrointestinal encephalopathy, myoclonic epilepsy, Alzheimer's disease, muscular dystrophy, Lou Gehrig's disease, and cancer. In yet other examples, the subject may be administered the fusion protein of the present disclosure for treating a lysosomal disorder, such as a lipid storage disease of the group of sphingolipoidoses disease (e.g., a Niemann-Pick disease, Fabry disease, Krabbe disease, Gaucher disease, Tay-Sachs disease or metachromatic leukodystrophy), Hunter syndrome, I-cell disease, multiple sulfatase deficiency, mucolipidosis type II and IIIA, galactosialidosis, GM2-AP deficiency, SAP deficiency and Salla disease. In yet other examples, the subject may be administered the fusion protein provided by the present disclosure, e.g., any of SEQ ID NOS. 69-71, for treating Parkinson's Disease.

In other embodiments, the cell comprising the fusion protein of the present disclosure may be a cell that has been engineered to express the fusion protein. In some examples, such engineered cell may be obtained, e.g., isolated, from a subject. Methods for engineering a cell to express fusion protein of the disclosure are known to one of ordinary skill in the art and include methods described herein below, in a section entitled "Method for Intracellular Delivery".

Pharmaceutical Composition

Also provided by the present disclosure is a pharmaceutical composition comprising a fusion protein or a conjugate as described above, and a pharmaceutically acceptable diluent, carrier, additive and/or excipient.

Preparation of pharmaceutical compositions is discussed in, for example, in Hoover, John E. (eds.) Remington's Pharmaceutical Sciences, Mack Publishing Co., Easton, Pa. 18$^{th}$ edition (1990), and in Liberman, H. A. and Lachman, L. (eds.) Pharmaceutical Dosage Forms, Marcel Decker, New York, N.Y. (1989), the entire contents of each of which are hereby incorporated herein by reference.

A pharmaceutical composition may be delivered to cells in vitro, for example by contacting the cells with the pharmaceutical composition. Alternatively, for delivery in vivo, the pharmaceutical composition provided in the present disclosure may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques.

Injectable pharmaceutical compositions, for example, sterile injectable aqueous or oleaginous suspensions, may be formulated according to the techniques known in the art using suitable dispersing or wetting agents and suspending agents. The sterile injectable pharmaceutical composition may also be a sterile injectable solution or a suspension in a nontoxic parenterally acceptable diluent or solvent, for example, 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids, such as oleic acid, are useful in the preparation of injectables. Dimethyl acetamide, surfactants including ionic and non-ionic detergents, and polyethylene glycols can be used. Mixtures of solvents and wetting agents such as those discussed above are also useful.

Pharmaceutical compositions for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The fusion proteins or compositions can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration may include pharmaceutically acceptable emulsions, solutions, suspensions, syrups, and elixirs containing inert diluents commonly used in the art, such as water. Such pharmaceutical compositions may also comprise adjuvants, such as wetting agents, emulsifying and suspending agents, and sweetening, flavoring, and perfuming agents.

Solid dosage forms for oral administration may include capsules, tablets, pills, powders, and granules. In such solid dosage forms, a fusion protein may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as can be provided in a dispersion of active compound in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings.

Suppositories for rectal administration of the fusion proteins discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

The fusion protein of the present disclosure may be administered by a variety of methods, including, for example, orally, enterally, mucosally, percutaneously, or parenterally. Parenteral administration is preferred, especially by intravenous, intramuscular, subcutaneous, intracutaneous, intraarticular, intrathecal, and intraperitoneal infusion or injection, including continuous infusions or intermittent infusions with pumps available to those skilled in the art. Alternatively, the fusion protein may be administered by means of micro-encapsulated preparations, for example based on liposomes.

Methods for Intracellular Delivery

In some embodiments, the present disclosure also provides methods for intracellular delivery of a protein of interest to a non-nuclear organelle in a cell. The method comprises contacting the cell with a fusion protein, a nucleic acid, a vector or a conjugate as described herein above. In one example, the non-nuclear organelle is mitochondria. In one example, the protein of interest is FXN, e.g., human FXN.

Contacting the cell with a fusion protein of the present disclosure may occur in the context of administering a fusion protein, a nucleic acid, a vector, a conjugate, a pharmaceutical composition for the present disclosure, or any combination thereof, to a subject, e.g., a human. The subject may have a pathological condition, e.g., a genetic disorder, such as a non-nuclear organelle associated disorder. In one specific example, the pathological condition is Friedrich's Ataxia.

In some embodiments, the method for intracellular delivery of a protein of interest to a non-nuclear organelle may comprise contacting a cell, e.g., an isolated cell, by contacting the cell with a nucleic acid encoding a fusion protein of the present disclosure or with a vector comprising the nucleic acid of the present disclosure. In some aspects, the cell is stem cell or an iPS cell. In other aspects, a cell may be selected from the group consisting of a muscle progenitor cell, a neuron progenitor cell, a bone marrow stem cell, a bacterial cell, or a yeast cell. In some aspects, the cell may be a muscle progenitor cell, a neuron progenitor cell, a bone marrow stem cell, a bacterial cell line, or a yeast cell line, with a nucleic acid encoding a fusion protein of the disclosure. The methods may further comprise additional steps for facilitating delivery of a nucleic acid or a vector of the present disclosure into the cell, e.g., electroporation, chemical or polymeric transfection, viral transduction, mechanical membrane disruption, or other method know to a skilled artisan.

In some embodiments, the present disclosure also provides methods for increasing an amount of protein of interest delivered to a cell. As demonstrated by certain experimental data included in the present disclosure, e.g., in Example 6, cells treated with fusion proteins comprising a protein of interest, CPP and TES contained significantly higher amounts of the protein of interest than cells treated with a fusion protein comprising a protein of interest and CPP, but not TES. Thus, the experimental data indicates that TES facilitates delivery to and/or accumulation of a protein of interest in a cell. Accordingly, introducing TES into a fusion protein comprising CPP and a protein of interest can significantly increase the amount of protein of interest in a cell.

Without wishing to be bound by a specific theory, it is believed that cleavage of TES by endogenous proteases in a cell facilitates removal of the CPP from the fusion protein and prevents the CPP from facilitating diffusion of the protein of interest across the plasma membrane and out of the cell. This allows the protein of interest to accumulate in the cell, resulting in increased amounts of protein of interest delivered to a cell.

In some embodiments, the cell may be in a subject, e.g., a human. Thus, methods for increasing an amount of protein of interest delivered to a cell may allow to decrease a dose of a fusion protein to be delivered to a subject as a part of therapy, e.g., for treating a non-nuclear organelle associated disorder.

In some embodiments, the protein of interest may be FXN. Therefore, in some embodiments, the fusion protein may comprise CPP (e.g., SEQ ID NO: 11 or SEQ ID NO: 83), TES and FXN (e.g., SEQ ID NO: 1 or SEQ ID NO: 2), and the subject may have a disorder associated with FXN deficiency, e.g., Friedreich's Ataxia. In other embodiments, the fusion protein may comprise CPP (e.g., SEQ ID NO: 11 or SEQ ID NO: 83), TES and FXN (e.g., SEQ ID NO: 1 or SEQ ID NO: 2), and the subject may have a disorder that is not associated with FXN deficiency, e.g., Leigh Syndrome, French Canadian Type.

In some embodiments, the protein of interest may be PARKIN. Therefore, in some embodiments, the fusion protein may comprise CPP (e.g., SEQ ID NO: 11 or SEQ ID NO: 83), TES and PARKIN (e.g., SEQ ID NO: 7), and the subject may have Parkinson's disease associated with a mutation in PARK2 gene encoding PARKIN. In other embodiments, the fusion protein may comprise CPP (e.g., SEQ ID NO: 11 or SEQ ID NO: 83), TES and PARKIN (e.g., SEQ ID NO: 7), and the subject may have Parkinson's disease not associated with a mutation in PARK2 gene encoding PARKIN, e.g., Parkinson's disease associated with a mutation in PINK1 (PARK6) gene.

In some aspects, methods for increasing an amount of protein of interest delivered to a cell provided by the present disclosure comprise modifying sequence of a fusion protein comprising the protein of interest and a cell penetrating peptide (CPP) by introducing into the fusion protein a target enhancing sequence (TES), thereby producing a modified fusion protein; and contacting a cell with the modified fusion protein, thereby increasing the amount of the protein of interest delivered to the cell.

The CPP may be located at the N-terminus of the modified fusion protein and the TES may be fused at the C-terminus of the CPP. For example, the modified fusion protein may comprise, starting at the N-terminus: CPP; TES and a protein of interest. In another example, the modified fusion protein may comprise, starting at the N-terminus: CPP, TES, OTS and a protein of interest.

The CPP may also be located at the C-terminus of the modified fusion protein and the TES may be fused at the N-terminus of the CPP. For example, the modified fusion protein may comprise, starting at the N-terminus: protein of interest, TES and CPP. In another example, the modified fusion protein may comprise, starting at the N-terminus: protein of interest, OTS, TES and CPP. In yet another example, the modified fusion protein may comprise, starting at the N-terminus: OTS, protein of interest, TES and CPP.

In some embodiments, the protein of interest may be any protein of interest as described herein, e.g., any protein of interest listed in Table 2 herein. For example, the protein of interest may be selected from the group consisting of Frataxin (FXN), Tafazin, Pyruvate Dehydrogenase (PDH), SLIRP, LRPPC, PARK2 protein, PARK6 protein, PARK7 protein, and a variant or derivative thereof. In one example, the protein of interest is Frataxin (FXN) or a variant or derivative thereof. In another example, the protein of interest is PARK2 protein (PARKIN) or a variant or derivative thereof.

In some embodiments, the CPP may be any CPP as described herein, e.g., any CPP listed in Table 4 herein. For example, the CPP may comprise a peptide selected from the group of CPPs listed in the Database of Cell-Penetrating Peptides CPPsite 2.0. For example, the CPP may comprise a peptide selected from the group consisting of HIV-TAT, galanin, mastoparan, transportan, penetratin, polyarginine, VP22, and a variant or derivative thereof. In one embodiment, the CPP may comprise HIV-TAT or a variant or derivative thereof.

In some embodiments, the TES included in the modified fusion protein may be any TES described herein. For example, the TES may be a nuclear export signal peptide, e.g., comprising a sequence having at least 85%, at least 90%, at least 95% or at least 99% sequence identity to any one of SEQ ID NOs. 36-43. In some examples, the nuclear export signal peptide may comprise a peptide selected from the group consisting of NES1, NES2, NES3, NES4, NES5, NES6, NES7, NES8, and a variant or derivative thereof. In one example, the nuclear export signal peptide may comprise NES1 or a variant or derivative thereof. In another example, the nuclear export signal peptide may comprise NES or a variant or derivative thereof.

The TES included in the modified fusion protein may also be a protease sensitive peptide. For example, the TES may comprise a ubiquitin-like modifier, e.g., may comprise a sequence having at least 85%, at least 90%, at least 95%, or at least 99% sequence identity to any one of SEQ ID NOs. 18-31.

In other examples, the TES may comprise a protease sensitive peptide selected from the group consisting of ubiquitin, a caspase cleavage domain, a calpain cleavage domain, SUMO1, SUMO2, SUMO3, SUMO4, ISG15, Atg8, Atg12, NEDD8, and a variant or derivative thereof.

In some examples, the modified fusion protein may comprise an amino acid sequence having at least 85%, at least 90%, at least 95% or at least 99% sequence identity to any of SEQ ID NOs. 55-61 and 69-71.

Methods of Treatment

Provided herein is a therapeutic compound for treating a non-nuclear organelle associated disorder in a subject in need thereof. The therapeutic compound, in some embodiments, may comprise a fusion protein, a nucleic acid, a vector, or a conjugate of the present disclosure. Non-limiting examples of a non-nuclear organelle associated disorder may include, in some embodiments, a mitochondrial disorder and a lysosomal disorder. In some embodiments, the non-nuclear organelle associated disorder is a genetic disorder.

Also provided in the present disclosure are methods for treating a non-nuclear organelle associated disorder that comprise administering to a subject in need thereof a fusion protein, a nucleic acid, a vector, a conjugate, a cell, or a pharmaceutical composition as described herein. In some embodiments, the non-nuclear organelle associated disorder is a mitochondrial disorder. In one specific example, the mitochondrial disorder is Friedrich's Ataxia.

In some examples, the non-nuclear organelle associated disorder may be a lysosomal disorder, i.e., a disorder associated with a dysfunction of lysosomes.

In some examples, the non-nuclear organelle associated disorder may be selected from the group consisting of Friedreich's Ataxia (FRDA), Barth Syndrome, Parkinson's Disease, Leigh Syndrome, such as Leigh Syndrome, French Canadian Type, and Pyruvate Dehydrogenase Deficiency.

Subjects suffering from or who may be at risk of developing any one or more of the disorders disclosed herein may be selected for treatment based on multiple factors, including symptom presentation, and/or the identification of a marker that predisposes the subject to the disease or disorder (such as a genetic mutation).

As used herein, the term "subject" includes a human or non-human animal, preferably a vertebrate, and more preferably a mammal. A subject may also include a transgenic organism. Most preferably, the subject is a human, such as a human suffering from or predisposed to developing a non-nuclear organelle associated disorder, such as Friedrich's Ataxia or Parkinson's Disease.

As used herein, the term "treating a non-nuclear organelle associated disorder" comprises reducing, ameliorating, or eliminating one or more symptom(s) associated with the non-nuclear organelle associated disorder, e.g., Friedreich's Ataxia or Parkinson's Disease. The term "treating a non-nuclear organelle associated disorder" also comprises achieving, partially or substantially, one or more of the following: ameliorating or improving a symptom or an indicator associated with a non-nuclear organelle associated disorder; arresting the progression or worsening of at least one symptom of the non-nuclear organelle associated disorder. The term "treating a non-nuclear organelle associated disorder" also comprises preventing the development or delaying the appearance of at least one symptom of a non-nuclear organelle associated disorder, or developing at least one symptom of the non-nuclear organelle associated disorder that is of a lesser severity than the same symptom that would develop without treatment.

Methods of Treating Friedreich's Ataxia (FRDA)

In one embodiment, the present disclosure provides methods for treating Friedreich's Ataxia (FRDA) that comprise administering to a subject in need thereof a fusion protein of the disclosure. For example, the present disclosure provides methods for treating FRDA that comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) any TES as described herein.

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating FRDA comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating FRDA comprise administering to a subject in need thereof a fusion protein comprising or consisting of an amino acid sequence selected from the group consisting of SEQ ID NO: 56, SEQ ID NO: 57, SEQ ID NO: 58, SEQ ID NO: 59, SEQ ID NO: 60, SEQ ID NO: 61 and SEQ ID NO: 81.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 56.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 57.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 58.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 59.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 60.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 61.

In one embodiment, methods for treating FRDA comprise administering to a subject in need thereof a fusion protein comprising or consisting of an amino acid sequence having at least about 85%, about 90%, about 95% or about 99% sequence identity to SEQ ID NO: 81.

The term "FRDA", as used herein, encompasses any disease, disorder or condition associated with a frataxin deficiency. The term "FRDA-associated disease, disorder or condition", as used herein, encompasses a disease, disorder or condition secondary to and/or caused by FRDA, i.e., when present in a subject, it accompanies FRDA and is not present in a subject in the absence of FRDA. Non-limiting examples of an FRDA-associated disease, disorder, or condition, include FRDA-associated pneumonia, FRDA-associated hypertrophic cardiomyopathy and FRDA-associated diabetes. Other non-limiting examples of an FRDA-associated disease, disorder or condition include an FRDA-associated disease, disorder or condition characterized by, without limitation:

(1) a neurological deficiency including, without limitation, one or more of the following: loss of proprioception, loss of reflexes, loss of ability to walk, loss of ability to hold gaze with eyes;
(2) impaired swallowing and/or a progressive loss of the ability to swallow; progressive loss of hearing;
(3) progressive loss of vision due to retinal degeneration from lack of FXN;
(4) progressive loss of speech;
(5) metabolic syndrome including, without limitation, elevated triglycerides, low high-density lipoprotein (HDL) cholesterol, and elevated low-density lipoprotein (LDL) cholesterol;
(6) scoliosis that requires surgery to correct; and/or combinations thereof.

In some embodiments, administration of a fusion protein of the present disclosure to a subject may treat FRDA, including, e.g., an FRDA-associated disease, disorder or condition. "Treating FRDA", as used herein, encompasses ameliorating, improving or achieving a reduction in the severity of FRDA, including, e.g., an FRDA-associated disease, disorder or condition. For example, "treating FRDA" encompasses ameliorating, improving or achieving a reduction in at least one symptom or indicator associated with FRDA. "Treating FRDA", as used herein, also encompasses delaying progression of FRDA, including, e.g., an FRDA-associated disease disorder or condition, e.g., delaying appearance of at least one symptom or indicator associated with FRDA or preventing an increase in the severity of at least one symptom or indicator associated with FRDA, in a subject.

In some embodiments, the term "treating FRDA" also encompasses achieving increased survival (e.g., survival time) of a subject, e.g., a human, with FRDA, including, e.g., an FRDA-associated disease, disorder or condition. For example, treatment of FRDA may result in an increased life expectancy of a subject, e.g., a human, with FRDA, including, e.g., an FRDA-associated disease disorder or condition. In some embodiments, treatment of FRDA in the context of the present disclosure may result in an increased life expectancy of a subject of greater than about 10%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, or greater than about 200% or more, as compared to the average life expectancy of one or more control individuals with similar disease without treatment.

In some embodiments, treatment of FRDA, including, e.g., an FRDA-associated disease, disorder or condition, in the context of the present disclosure may result in an increased life expectancy of a subject by greater than about 6 months, greater than about 8 months, greater than about 10 months, greater than about 12 months, greater than about 2 years, greater than about 4 years, greater than about 6 years, greater than about 8 years, or greater than about 10 years or more, as compared to the average life expectancy of one or more control individuals with similar disease without treatment. In some embodiments, treatment of FRDA, including, e.g., an FRDA-associated disease, disorder or condition in the context of the present disclosure may result in a long-term survival of a subject, e.g., a human, with FRDA, including, e.g., an FRDA-associated disease, disorder or condition. The term "long-term survival", as used herein, refers to a survival time or life expectancy longer than about 40 years, 45 years, 50 years, 55 years, 60 years, or longer.

Clinical assessments known to one of ordinary skill in the art may be used to assess FRDA, including, e.g., an FRDA-associated disease, disorder or condition, to determine the severity of the FRDA and/or to determine the effect of administration to a subject of a fusion protein of the present disclosure. Examples of methods of clinical assessment of FRDA, including assessments of the severity of FRDA, are described, e.g., in Paap et al., "Standardized Assessment of Hereditary Ataxia Patients in Clinical Studies", *Mov Disord Clin Pract*. 2016, 3(3):230-240 and Patel et al., "Progression of Friedreich ataxia: quantitative characterization over 5 years", *Ann Clin Transl Neurol* 2016, 3(9):684-694, the entire contents of each of which are hereby incorporated herein by reference.

Timed 25-Foot Walk (T25-FW) is a quantitative mobility and leg function performance test that measures the time needed to complete a 25-foot walk. In some embodiments, administration to a subject of a fusion protein of the present disclosure may result in a decrease in the severity of FRDA as measured, e.g., by the time needed to complete a 25-foot walk. For example, administration to a subject of a fusion protein of the disclosure may result in a decrease in the time needed to complete a 25-foot walk, e.g., a decrease of at least about 5%, at least about 10%, at least about 25%, or at least about 50% in the time needed to complete a 25-foot walk, as compared to the time needed to complete a 25-foot walk measured in the subject prior to administration of a fusion protein of the disclosure, or as compared to a baseline value. A baseline value may be the time needed to complete a 25-food walk measured prior to administration of a fusion protein of the present disclosure.

In other embodiments, administration to a subject of a fusion protein of the present disclosure may delay progression of FRDA in the subject as measured, e.g., by the time needed to complete a 25-foot walk. For example, administration to a subject of a fusion protein of the present disclosure may result in a substantially similar time needed to complete a 25-foot walk, or a lack of a substantial increase in the time needed to complete a 25-foot walk (e.g., less than a 20%, less than a 10%, or less than a 5% increase in the time needed to complete a 25-foot walk), as compared to the baseline value, i.e., time needed to complete a 25-foot walk measured in the subject prior to administration of a fusion protein of the present disclosure.

The Modified Friedreich's Ataxia Rating Scale (mFARS) is an examination-based rating scale for assessing the severity of FRDA as described, e.g., in Burk et al., "Monitoring progression in Friedreich ataxia (FRDA): the use of clinical scales", *J of Neurochemistry* 2013, 126(suppl. 1):118-124 and Rummey et al., "Psychometric properties of the Friedreich's Ataxia Rating Scale", *Neurol Genet* 2019, 5:e371, the entire contents of each of which are hereby incorporated herein by reference.

In some embodiments, the mFARS score may comprise at least one of the following subscores: a) a score based on the Functional Disability Rating Scale (FARS-FDS; 0-6 scale; assessment usually made by a neurologist; b) a score based on the Activities of Daily Living Scale (FARS-ADL, 0-36 scale; assessment made by a patient or caregiver); and c) a score based on the Neurological Rating Scale (FARS-neuro) 0-125 scale; assessment made by a neurologist). In some examples, the FARS_ADL score is a FARS rating scale assessing subject ability to complete ADLs (e.g., speech, cutting food, dressing, and personal hygiene), with scores ranging from 0 to 36 points. The respondent may be the subject; a combination of the subject and family; or a family member, spouse or caregiver for those subjects unable to complete the test.

In some embodiments, the score based on the Neurological Rating Scale may include modified scoring of the neurological rating scale involving direct subject participation and targeting specific areas impacted by FRDA, such as bulbar, upper limb, lower limb, and upright stability (mFARS-neuro, 0-99 scale). The mFARS-neuro excludes subscale D (peripheral nervous system) and the first 2 questions of subscale A (bulbar) from the neurological rating scale of the FARS questionnaire.

In some embodiments, the mFARS score may be based on two subscores derived from the full FARS questionnaire: mFARS-neuro as described above and the FARS_ADL as described above.

In some embodiments, administration to a subject of a fusion protein of the present disclosure may result in a decrease in the severity of FRDA as measured, e.g., by an mFARS score, or at least one mFARS subscore as described herein. For example, administration to a subject of a fusion protein of the present disclosure may result in a decrease in an mFARS score or at least one mFARS subscore, as compared to a baseline value, i.e., the mFARS score or the at least one mFARS subscore measured in the subject prior to administration of a fusion protein of the present disclosure.

In other embodiments, administration to a subject of a fusion protein of the present disclosure may delay progression of FRDA in the subject as measured, e.g., by an mFARS score or at least one mFARS subscore as disclosed herein. For example, administration to a subject of a fusion protein of the present disclosure may result in a substantially similar mFARS score or at least one mFARS subscore, or a substantial lack of an increase in an mFARS score or at least one mFARS subscore, as compared to a baseline value, i.e., the mFARS score or the at least one mFARS subscore measured in the subject prior to administration of a fusion protein of the present disclosure, or as compared to a baseline value.

The Nine-Hole Peg Test (9HPT) may be used to measure finger dexterity in subjects with FRDA. In this test, a subject is asked to take pegs from a container, one by one, and place them into the nine holes on the board as quickly as possible. The subject must then remove the pegs from the holes, one by one, and replace them back into the container. Scores are based on the time taken to complete the test activity, recorded in seconds.

In some embodiments, administration to a subject of a fusion protein of the present disclosure may result in a decrease in the severity of FRDA as measured, e.g., by a 9HPT score. For example, administration to a subject of a fusion protein of the present disclosure may result in an decrease in a 9HPT score expressed as time to complete the test activity (e.g., at least an about 5%, 10%, 25%, or 50% decrease in a 9HPT score expressed as time to complete the test activity), as compared to a baseline value, i.e., the 9HPT score measured in the subject prior to administration of a fusion protein of the present disclosure.

In other embodiments, administration to a subject of a fusion protein of the present disclosure may delay progression of FRDA in the subject as measured, e.g., by a 9HPT score. For example, administration to a subject of a fusion protein of the present disclosure may result in a substantially similar 9HPT score, or a lack of a substantial increase in a 9HPT score expressed as time to complete the test activity, as compared to a baseline value, i.e., the 9HPT score measured in the subject prior to administration of a fusion protein of the present disclosure.

In some embodiments, administration to a subject of a fusion protein of the present disclosure results in an increase in the level of hFXN in at least one tissue or biological fluid of the subject, as compared to a baseline level, i.e., the hFXN level in the at least one tissue or biological fluid of the subject prior to administration of a fusion protein of the present disclosure. In some embodiments, the increase in the level of hFXN in the at least one tissue or biological fluid of a subject resulting from administration of a fusion protein of the present disclosure to the subject is sufficient to have a therapeutic effect, i.e., sufficient to treat FRDA in the subject.

In some embodiments, administration of a fusion protein of the present disclosure to a subject with FRDA may result in a level of hFXN in at least one tissue or biological fluid of the subject that is lower than the level of hFXN in the at least one tissue or biological fluid of a subject who does not have FRDA (e.g., a normal, healthy subject), but is still sufficient to have a therapeutic effect, i.e., sufficient to treat FRDA in the subject. For example, after administration of a fusion protein of the present disclosure to a subject with FRDA, the level of hFXN in at least one tissue or a biological fluid of the subject may be about 10% to about 50%, about 20% to about 60%, or about 30% to about 80% of the level of hFXN in the at least one tissue or a biological fluid of a subject who does not have FRDA (e.g., a normal, healthy subject), but the level of hFXN is still sufficient to have a therapeutic effect, i.e., sufficient to treat FRDA in the subject.

In some embodiments, administration to a subject with FRDA of a fusion protein of the present disclosure may result in an increase of at least about 5%, about 10%, about 25%, about 50%, about 100%, about 150%, about 200%, about 300%, about 400%, about 500%, or about 600% in the level of hFXN in at least one tissue or biological fluid of the subject, as compared to the hFXN level in the at least one tissue or biological fluid of the subject prior to administration of a fusion protein of the present disclosure, or as compared to a baseline level.

In some embodiments, administration to a subject with FRDA of a fusion protein of the present disclosure may result in an increase of about 5% to about 30%, about 10% to about 50%, about 25% to about 100%, about 50% to about 150%, about 100% to about 300%, about 50% to about 250%, about 150% to about 500% or about 200% to about 700% in the level of hFXN in at least one tissue or biological fluid of the subject, as compared to the hFXN level in the at least one tissue or biological fluid of the subject prior to administration of a fusion protein of the present disclosure, or as compared to a baseline level. In some embodiments, administration to a subject of a fusion protein of the present disclosure may result in an increase of at least about 2-fold, about 3-fold, about 4-fold, about 5-fold in the level of hFXN in at least one tissue or biological fluid of the subject, as compared to the hFXN level in the at least one tissue or biological fluid of the subject prior to administration of a fusion protein of the present disclosure, or as compared to a baseline level. In some embodiments, administration to a subject of the disclosed TAT-FXN fusion polypeptide and/or a pharmaceutical composition comprising the disclosed TAT-FXN fusion polypeptide may result in an increase of between about 2-fold and about 5-fold, or between about 2-fold and about 10-fold, in the level of hFXN in at least one tissue or biological fluid of the subject, as compared to the hFXN level in the at least one tissue or biological fluid of the subject prior to administration of a fusion protein of the present disclosure, or as compared to a baseline level.

In some embodiments, the tissue of a subject in which the level of hFXN may be measured and/or increased may be any tissue that is capable of being biopsied. In some embodiments, the tissue may comprise bronchoalveolar tissue (which may be sampled by, e.g., bronchoalveolar brushing), a mucous membrane (e.g., nasal mucous membrane, which may be sampled by, e.g., nose brushing), a hair follicle, skin tissue, or buccal tissue. In some embodiments, the tissue comprises skin tissue or buccal tissue.

In some embodiments, the biological fluid of a subject in which the level of hFXN may be measured and/or increased may be blood or a component thereof (e.g., serum, plasma, platelets, or any other blood component), urine, or saliva.

FRDA-Associated Pneumonia

Subjects diagnosed with FRDA suffer neurodegeneration of the dorsal root ganglia causing progressive ataxia. This typically leads to the progressive loss of an ability to walk, feed oneself, talk, swallow, and pulmonary aspiration. The event of pulmonary aspiration can lead to pneumonia, frequent hospitalizations, and, eventually, death over a period of 10-15 years from the date of diagnosis.

Accordingly, administration of a fusion protein of the present disclosure can be effective as a protein replacement therapy in FXN-deficient subjects diagnosed with FRDA to prevent pulmonary aspiration, thereby preventing the pneumonia that follows pulmonary aspiration. Accordingly, the present disclosure provides methods of treating an FRDA-associated pneumonia in a subject, comprising administering to a subject in need thereof a fusion protein of the present disclosure, thereby treating the FRDA-associated pneumonia in the subject.

FRDA-Associated Hypertrophic Cardiomyopathy

Hypertrophic cardiomyopathy is a condition in which the muscles of the heart thicken, making it difficult for the heart to pump blood through the circulatory system. It can be caused by a deficiency in FXN in the mitochondria of the heart cells. In subjects diagnosed with FRDA, progressive hypertrophic cardiomyopathy about 50% of the time progresses to heart failure and death. Protein replacement therapy with a fusion protein of the present disclosure can replace the FXN deficiency underlying hypertrophic cardiomyopathy.

Administration of a fusion protein of the present disclosure can, therefore, be effective as a protein replacement therapy in FXN-deficient subjects diagnosed with both FRDA and hypertrophic cardiomyopathy. Accordingly, the present disclosure provides methods of treating an FRDA-associated hypertrophic cardiomyopathy in a subject, comprising administering to a subject in need thereof a fusion protein of the present disclosure, thereby treating the FRDA-associated hypertrophic cardiomyopathy in the subject.

Diabetes

The hallmark of diabetes is an inability to properly regulate blood levels of glucose, resulting in elevated blood glucose levels. In subjects diagnosed with FRDA, diabetes often shows up as a consequence of FXN-deficient mitochondria in the pancreas. Protein replacement therapy with a fusion protein of the present disclosure can replace the FXN deficiency underlying diabetes.

Administration of a fusion protein of the present disclosure, can, therefore, be effective as a protein replacement therapy in FXN-deficient subjects diagnosed with diabetes. Accordingly, the present disclosure provides methods of treating an FRDA-associated diabetes in a subject, comprising administering to a subject in need thereof a fusion protein of the present disclosure, thereby treating the FRDA-associated diabetes in the subject.

Other FRDA-Associated Diseases/Disorders

Subjects diagnosed with FRDA often experience other disorders associated with FXN deficiency. Such FRDA-associated disorders can include, without limitation: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low high-density lipoprotein (HDL) cholesterol, and elevated low-density lipoprotein (LDL) cholesterol; scoliosis that requires surgery to correct; and/or combinations thereof. Protein replacement therapy with a fusion protein of the present disclosure can replace the FXN deficiency underlying these FRDA-associated diseases/disorders.

Administration of a fusion protein of the present disclosure can, therefore, be effective as a protein replacement therapy in FXN-deficient subjects diagnosed with FRDA and experiencing neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; scoliosis that requires surgery to correct; and/or combinations thereof.

Accordingly, the present disclosure provides methods of treating an FRDA-associated disease, disorder or condition, comprising administering to a subject in need thereof a fusion protein of the present disclosure, wherein the FRDA-associated disease, disorder or condition is selected from: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; and scoliosis that requires surgery to correct.

In certain embodiments, treatment of a subject in need thereof with a fusion protein, a pharmaceutical composition or a therapeutic compound of the present disclosure, e.g., a fusion protein comprising FXN, increases cellular levels of FXN in a subject. In some embodiments, the methods of the present disclosure increase the cellular levels of FXN by at least about 10%, e.g., about 20%, about 25%, about 30%, about 40%, about 50%, about 60%, about 70%, about 75%, about 80%, about 85%, about 90%, about 95%, or more, relative to the levels of FXN in the subject prior to treatment. In another embodiment, the methods of the present disclosure increase the cellular levels of FXN by at least about two-fold, at least about three-fold, at least about four-fold, at least about five-fold, at least about six-fold, at least about seven-fold, at least about eight-fold, at least about nine-fold, or at least about ten-fold. In some embodiments, the increase is measured by comparing the cellular levels of FXN in a subject before and after administration of the fusion protein of the disclosure.

Before, during, and after the administration of the fusion protein, pharmaceutical composition and/or therapeutic compound of the disclosure, the cellular levels of FXN in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of a fusion protein disclosed herein to increase the cellular levels of FXN in a subject. In some embodiments, the methods may include administration of the fusion protein disclosed herein to increase the cellular levels of FXN by more than about 1%, 2%, 5%, 10%, 20%, 25%, 30%, 40%, 50%, 60%, 70%, 75%, 80%, 85%, 90%, or 95% of the subject's cellular levels of FXN prior to treatment. Cellular levels of FXN may be measured by methods known in the art. For example, cellular levels of FXN may be measured by collecting samples, such as skin biopsies (punch) buccal swab, platelets and analyzing them for FXN using ELISA, Hybrid LBA-LC-MS/MS or other mass spectrometry related methods.

Methods for Treating Leigh Syndrome, French Canadian Type (LSFC)

The present disclosure also provides methods of treating Leigh Syndrome, French Canadian Type (LSFC) that comprise administering to a subject in need thereof a fusion protein of the disclosure, such that the LSFC in the subject is treated. It was surprisingly discovered that the mitochondrial impairment in LRPPRC-deficient cells, as evidenced by acidification of cell growth media, is reduced by treatment of the cells with hFXN fusion proteins of the present disclosure. It was also surprisingly discovered that the amount of CYR61 protein secreted by the LRPPRC-deficient cells into the cell growth media is reduced by treatment of the cells with hFXN fusion proteins of the present disclosure. Further, it was also surprisingly discovered that the hFXN fusion proteins of the present disclosure comprising TES are more potent in reducing acidification of the media and secretion of CYR61 from LRPPRC-deficient cells than the hFXN fusion protein that does not comprise TES.

The above described discoveries indicate that certain molecular and cellular changes associated with deficiencies in LRPPRC may be mitigated and/or reversed by administering a hFXN fusion protein of the present disclosure. The above described discoveries also indicate that LSFC, which is associated with a deficiency in LRPPRC, may be treated by administering a hFXN fusion protein of the present disclosure. Further, the above described discoveries indicate that hFXN fusion proteins of the present disclosure comprising TES are more potent in treating LSFC and/or lactic acidosis in a subject with LSFC than hFXN fusion proteins that do not comprise TES.

In some embodiments, the present disclosure provides methods for treating LSFC in a subject in need thereof that comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) any TES as described herein.

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating LSFC comprise administering to a subject in need thereof a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating LSFC comprise administering to a subject in need thereof a fusion protein comprising or consisting of an amino acid sequence selected from the group consisting of SEQ ID NO: 56, SEQ ID NO: 57, SEQ ID NO: 58, SEQ ID NO: 59, SEQ ID NO: 60, SEQ ID NO: 61 and SEQ ID NO: 83.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 56.

In one embodiment, methods for treating LSFC comprise administering to a subject in need thereof a fusion protein comprising an amino acid sequence having at least about 85%, about 90%, about 95% or about 99% sequence identity to SEQ ID NO: 57.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 58.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 59.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 60.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 61.

In one embodiment, methods for treating LSFC comprise administering to a subject in need thereof a fusion protein comprising or consisting of an amino acid sequence having at least about 85%, about 90%, about 95% or about 99% sequence identity to SEQ ID NO: 83.

In some embodiments, the present disclosure provides methods for lactic acidosis in a subject with LSFC that comprise administering to a subject in need thereof a fusion protein of the disclosure, such that lactic acidosis in the subject is treated. For example, the present disclosure provides methods for treating lactic acidosis in a subject with LSFC that comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) any CPP as described herein; and 3) any TES as described herein.

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) any TES as described herein.

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating lactic acidosis in a subject with LSFC comprise administering to the subject a fusion protein comprising: 1) an amino acid sequence having at least 85%, at least 90%, at least 95%, or at least 99% sequence identity to full-length hFXN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating lactic acidosis in a subject with LSFC comprise administering to the subject a fusion protein comprising or consisting of an amino acid sequence selected from the group consisting of SEQ ID NO: 56, SEQ ID NO: 57, SEQ ID NO: 58, SEQ ID NO: 59, SEQ ID NO: 60, SEQ ID NO: 61 and SEQ ID NO: 83.

In one embodiment, for treating lactic acidosis in a subject with LSFC comprise administering to the subject a fusion protein comprising or consisting of an amino acid sequence having at least about 85%, about 90%, about 95% or about 99% sequence identity to SEQ ID NO: 56.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 57.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 58.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 59.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 60.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 61.

In one embodiment, methods for treating lactic acidosis in a subject with LSFC comprise administering to the subject a fusion protein comprising or consisting of an amino acid sequence having at least about 85%, about 90%, about 95% or about 99% sequence identity to SEQ ID NO: 83.

The term "treating LSFC", as used herein, encompasses ameliorating, improving or achieving a reduction in the severity of LSFC, e.g., ameliorating, improving or achieving a reduction in at least one symptom or indicator associated with LSFC in a subject. "Treating LSFC", as used herein, also encompasses delaying progression of LSFC, e.g., delaying appearance of at least one symptom or indicator associated with LSFC, or preventing an increase in the severity of at least one symptom or indicator associated with LSFC in a subject. In some embodiments, the at least one symptom or indicator associated with LSFC may be selected from the group consisting of developmental delay, ataxia, hypotonia, brain lesions, coma, abnormal breathing patterns, seizures, stroke-like episodes and lactic acidosis.

Methods of Treating Parkinson's Disease

In one embodiment, the present disclosure provides methods for treating Parkinson's Disease (PD) that comprise administering to a subject in need thereof a fusion protein of the disclosure. For example, the present disclosure provides methods for treating Parkinson's Disease that comprise administering to a subject in need thereof a fusion protein of the disclosure. For example, the present disclosure provides methods for treating Parkinson's Disease that comprise administering to a subject in need thereof a fusion protein comprising: 1) an amino acid sequence having at least 85%, at least 90%, at least 95%, or at least 99% sequence identity to PINK1 (SEQ ID NO: 8) as protein of interest; 2) any CPP as described herein; and 3) any TES as described herein.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PINK1 (SEQ ID NO: 8) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

In some embodiments, methods for treating Parkinson's Disease comprise administering to a subject in need thereof a fusion protein comprising: 1) an amino acid sequence having at least 85%, at least 90%, at least 95%, or at least 99% sequence identity to PINK1 (SEQ ID NO: 8) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In one embodiment, the present disclosure provides methods for treating Parkinson's Disease that comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) any CPP as described herein; and 3) any TES as described herein.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11); and 3) any TES as described herein.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to Ubiquitin (SEQ ID NO: 18).

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 7) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to a calpain cleavage domain of SEQ ID NO: 20.

In some embodiments, methods for treating Parkinson's Disease comprise administering to a subject in need thereof a fusion protein comprising: 1) an amino acid sequence having at least 85%, at least 90%, at least 95%, or at least 99% sequence identity to PARKIN (SEQ ID NO: 1) as protein of interest; 2) an amino acid sequence having at least 85%, at least 90%, at least 95% or at least 99% to TAT-HIV (SEQ ID NO: 11); and 3) an amino acid sequence having at least 85%, at least 90%, at least 95% or at least 99% to any one of SEQ ID NO 19, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31, SEQ ID NO: 32, SEQ ID NO: 33, SEQ ID NO: 34 and SEQ ID NO: 35.

In some embodiments, methods for treating Parkinson's Disease comprise administering to a subject in need thereof a fusion protein comprising or consisting of an amino acid sequence selected from the group consisting of SEQ ID NO: 69, SEQ ID NO: 70 and SEQ ID NO: 71.

In one embodiment, methods for treating Parkinson's Disease comprise administering to a subject in need thereof a fusion protein comprising or consisting of an amino acid sequence having at least about 85%, about 90%, about 95% or about 99% sequence identity to SEQ ID NO: 69.

In one embodiment, methods for treating Parkinson's Disease comprise administering to a subject in need thereof a fusion protein comprising or consisting of an amino acid sequence having at least about 85%, about 90%, about 95% or about 99% sequence identity to SEQ ID NO: 70.

In one embodiment, methods for treating Parkinson's Disease comprise administering to a subject in need thereof a fusion protein comprising or consisting of an amino acid sequence having at least about 85%, about 90%, about 95% or about 99% sequence identity to SEQ ID NO: 71.

As used herein, the term "Parkinson's Disease" encompasses both sporadic form of Parkinson's Disease and familial form of Parkinson's Disease. Familial form of Parkinson's Disease account for about 5-10% of Parkinson's Disease cases, and mutations in approximately 20 genes are implicated in Parkinson's Disease. In some embodiments, familial form of Parkinson's Disease may be associated with mutations in one or more genes selected from the group consisting of PARK2 (PRKN), PINK1 (PRKN6), PARK7, SNCA and LRRK2. In one embodiment, the familial form of Parkinson's Disease may be associated with a mutation in PARK2 (PRKN). In another embodiment, the familial form of Parkinson's Disease may be associated with a mutation in PINK1 (PRKN6). In one embodiment, the Parkinson's Disease is not a sporadic form of Parkinson's Disease.

In one embodiment, the present disclosure provides methods for treating Parkinson's Disease associated with a mutation in PARK2 gene that comprises administering to a subject in need thereof a fusion protein of the present disclosure comprising PARKIN (SEQ ID NO: 7), e.g., a fusion protein comprising an amino acid sequence having at least about 85%, about 90%, about 95% or about 99% sequence identity to any one of SEQ ID NO: 69, SEQ ID NO: 70 or SEQ ID NO: 71.

In one embodiment, the present disclosure provides methods for treating Parkinson's Disease associated with a mutation in PINK1 (PRKN6) gene that comprises administering to a subject in need thereof a fusion protein of the present disclosure comprising PARKIN (SEQ ID NO: 7), e.g., a fusion protein comprising an amino acid sequence having at least about 85%, about 90%, about 95% or about 99% sequence identity to any one of SEQ ID NO: 69, SEQ ID NO: 70 or SEQ ID NO: 71.

In some embodiments, Parkinson's Disease is characterized by at least one symptoms selected from of the following:

a) a tremor, or shaking, which usually begins in a limb, often hand or fingers. The tremor associated with Parkinson's Disease may include a back-and-forth rubbing of the thumb and forefinger, known as a pill-rolling tremor, and a tremor of the hand when it is relaxed (at rest);
b) slowed movement (bradykinesia);
c) rigid muscles;
d) impaired posture and balance;
e) loss of automatic movements;

In addition, "non-motor symptoms" or "dopamine-non-responsive" signs or symptoms, are also common in subjects with Parkinson's Disease and may include any of the following:
f) cognitive impairment;
g) mood disorders, e.g., depression and anxiety;
h) sleeping problems, including REM Sleep Disorder, where individuals act out their dreams;
i) low blood pressure when standing;
j) constipation;
k) speech and swallowing problems; and
l) unexplained pains, drooling and smell loss.

The term "treating Parkinson's Disease", as used herein, encompasses reduction, alleviation or amelioration of one or more signs or symptoms of Parkinson's Disease as described above; diminishing the extent of Parkinson's Disease, maintaining stability (i.e., not worsening) of Parkinson's Disease, amelioration or palliation of the disease state. Treatment of Parkinson's Disease may include one or more of reduction, alleviation or amelioration of the cardinal or non-motor symptoms of PD as described above, e.g., reduction, alleviation or amelioration of tremor, bradykinesia, muscle rigidity, reduction in speech and swallowing problems, etc. In one embodiment, the treatment may also include inhibiting and slowing the progression of Parkinson's Disease.

Treatment does not need to be curative. Treatment outcomes need not be determined quantitatively. However, in certain embodiments, treatment outcomes can be quantitated by following the longitudinal course of Parkinson's Disease, using, e.g., the Unified Parkinson's Disease Rating Scale (UPDRS), or a revised UPDRS, knowns as MDS-UPDRS. The UPDRS is a scoring system most commonly used for clinical evaluation of Parkinson's disease. It contains 42 items that are evaluated by interview with the subject and clinical observation. A total of 199 point are possible on the UPDRS scale, with 199 representing the worst disability and 0 representing no disability. UPDRS comprises the following sections:
Part I: evaluation of mentation, behavior, and mood;
Part II: self-evaluation of the activities of daily life (ADLs) including speech, swallowing, handwriting, dressing, hygiene, falling, salivating, turning in bed, walking, and cutting food;
Part III: clinician-scored monitored motor evaluation;
Part IV: complications of therapy;
Part V: Hoehn and Yahr staging of severity of Parkinson's disease; and
Part VI: Schwab and England ADL scale.

These are evaluated by interview and clinical observation. Some sections require multiple grades assigned to each extremity. The revised UPDRS retains the four-scale structure of the original UPDRS, with a reorganization of the various subscales. The scales are titled; (1) nonmotor experiences of daily living (13 items), (2) motor experiences of daily living (13 items), (3) motor examination (18 items), and (4) motor complications (six items). Each subscale has 0-4 ratings, where 0=normal, 1=slight, 2=mild, 3=moderate, and 4=severe.

The UPDRS or MDS-UPDRS may be used to follow the progression of a person's Parkinson's disease or to measure benefits from a therapy, e.g., a therapy that comprises administering a fusion protein of the present disclosure.

In some embodiments, administering a fusion protein of the present disclosure to a subject in accordance with the methods described herein results in inhibition or in slowing down the Parkinson's Disease progression in the subject. Specifically, in some embodiments, administering a fusion protein of the present disclosure to a subject results in a substantially no increase of the UPDRS score in the subject over a period of time, e.g., over 1 week, 2 weeks, 3 weeks, 1 month, 2 months, 3 months, 6 months, 9 months, 1 year, 2 years, 3 years or 5 years. In some embodiments, administering of fusion protein of the disclosure to a subject results in a decrease of the UPDRS score in the subject over a period of time, e.g., over 1 week, 2 weeks, 3 weeks, 1 month, 2 months, 3 months, 6 months, 9 months, 1 year, 2 years, 3 years or 5 years.

Methods for Treating Barth Syndrome and Familial Isolated Dilated Cardiomyopathy In one embodiment, the present disclosure provides methods for treating Barth Syndrome and Familial Isolated Dilated Cardiomyopathy that comprise administering to a subject in need thereof a fusion protein of the disclosure. For example, the present disclosure provides methods for treating Barth Syndrome and Familial Isolated Dilated Cardiomyopathy that comprise administering to a subject in need thereof a fusion protein comprising: 1) an amino acid sequence having at least 85%, at least 90%, at least 95%, or at least 99% sequence identity to Tafazzin (SEQ ID NO: 3) as protein of interest; 2) any CPP as described herein; and 3) any TES as described herein.

In some embodiments, methods for treating Barth Syndrome and Familial Isolated Dilated Cardiomyopathy comprise administering to a subject in need thereof a fusion protein comprising: 1) an amino acid sequence having at least 85%, at least 90%, at least 95%, or at least 99% sequence identity to Tafazzin (SEQ ID NO: 3) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

Methods for Treating Pyruvate Dehydrogenase E1-Beta Deficiency

In one embodiment, the present disclosure provides methods for treating Pyruvate Dehydrogenase E1-Beta Deficiency that comprise administering to a subject in need thereof a fusion protein of the disclosure. For example, the present disclosure provides methods for treating Pyruvate Dehydrogenase E1-Beta Deficiency that comprise administering to a subject in need thereof a fusion protein comprising: 1) an amino acid sequence having at least 85%, at least 90%, at least 95%, or at least 99% sequence identity to PDHB (SEQ ID NO: 4) as protein of interest; 2) any CPP as described herein; and 3) any TES as described herein.

In some embodiments, methods for treating Pyruvate Dehydrogenase E1-Beta Deficiency comprise administering to a subject in need thereof a fusion protein comprising: 1) an amino acid sequence having at least 85%, at least 90%, at least 95%, or at least 99% sequence identity to PDHB (SEQ ID NO: 4) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

Methods for Treating Leigh Syndrome, French Canadian Type

In one embodiment, the present disclosure provides methods for treating Leigh Syndrome, French Canadian Type that comprise administering to a subject in need thereof a fusion protein of the disclosure. For example, the present disclosure provides methods for treating Leigh Syndrome, French Canadian Type that comprise administering to a subject in need thereof a fusion protein comprising: 1) an amino acid sequence having at least 85%, at least 90%, at least 95%, or at least 99% sequence identity to LRPPRC (SEQ ID NO: 5) or SLIRP (SEQ ID NO: 6) as protein of interest; 2) any CPP as described herein; and 3) any TES as described herein.

In some embodiments, methods for treating Leigh Syndrome, French Canadian Type comprise administering to a subject in need thereof a fusion protein comprising: 1) an amino acid sequence having at least 85%, at least 90%, at least 95%, or at least 99% sequence identity to LRPPRC (SEQ ID NO: 5) or SLIRP (SEQ ID NO: 6) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20).

Methods for Treating PLA2G6-Associated Neurodegeneration (PLAN)

In one embodiment, the present disclosure provides methods for treating PLA2G6-associated neurodegeneration (PLAN). In some embodiments, the term "PLA2G6-associated neurodegeneration (PLAN)" may comprise one or more of the following disorders: infantile neuroaxonal dystrophy (INAD), atypical neuroaxonal dystrophy (ANAD), Parkinsonian Syndrome which contains adult onset dystonia parkinsonism (DP) and autosomal recessive early-onset parkinsonism (AREP).

In some embodiments, the methods for treating PLAN comprise administering to a subject in need thereof a fusion protein comprising: 1) an amino acid sequence having at least 85%, at least 90%, at least 95%, or at least 99% sequence identity to any variant 1-9 of Phospholipase A2, Group VI as described in Table 2 (SEQ ID NOS: 72-80) as protein of interest; 2) any CPP as described herein; and 3) any TES as described herein.

In some embodiments, methods for treating PLAN comprise administering to a subject in need thereof a fusion protein comprising: 1) an amino acid sequence having at least 85%, at least 90%, at least 95%, or at least 99% sequence identity to any variant 1-9 of Phospholipase A2, Group VI as described in Table 2 (SEQ ID NOS: 72-80) as protein of interest; 2) an amino acid sequence having at least 85%, at least 90%, at least 95% or at least 99% to TAT-HIV (SEQ ID NO: 11); and 3) any TES as described herein, e.g., Ubiquitin (SEQ ID NO: 18) or calpain cleavage domain (SEQ ID NO: 20). Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The terms "administer", "administering" or "administration", as used herein, include any method of delivery of a fusion protein, a pharmaceutical composition or a therapeutic compound of the disclosure. In certain embodiments, the fusion protein, the pharmaceutical composition or a therapeutic compound of the present disclosure may be administered parenterally, e.g., intravenously, intramuscularly or subcutaneously. In one specific embodiment, the fusion protein, the pharmaceutical composition or a therapeutic compound of the present disclosure may be administered subcutaneously. Administering a fusion protein, a pharmaceutical composition or a therapeutic compound can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, etc.

EXAMPLES

Example 1. Comparison of Subcellular Localizations of hFXN and TAT-GG-hFXN Fusion Protein Determining the Subcellular Localization of hFXN in Rat L6 Myoblasts Following Treatment with TAT-GG-hFXN Fusion Protein by Immunofluorescence Staining.

The human frataxin protein (hFXN$_{1-210}$) is encoded in the nucleus and is synthesized as a 210 amino acid precursor protein, having the amino acid sequence as indicated in SEQ ID NO. 1 (Table 1). Following its expression, full-length hFXN$_{1-210}$ is directed to the mitochondria by its N-terminal 80 aa mitochondrial targeting sequence (MTS), where it is actively imported and proteolytically processed to yield the 130 aa mature form, or active fragment, of the protein (hFXN$_{81-210}$), with a predicted molecular weight of 14.2 kDa and a sequence as provided in SEQ ID NO. 2 (Table 1). The FXN mature form ultimately resides in the mitochondrial matrix.

```
SEQ ID NO. 1:
MWTLGRRAVA GLLASPSPAQ AQTLTRVPRP

AELAPLCGRR GLRTDIDATC TPRRASSNQR

GLNQIWNVKK QSVYLMNLRK SGTLGHPGSL

DETTYERLAE ETLDSLAEFF EDLADKPYTF

EDYDVSFGSG VLTVKLGGDL GTYVINKQTP

NKQIWLSSPS SGPKRYDWTG KNWVYSHDGV

SLHELLAAEL TKALKTKLDL SSLAYSGKDA

SEQ ID NO. 2:
SGTLGHPGSL DETTYERLAE ETLDSLAEFF

EDLADKPYTF EDYDVSFGSG VLTVKLGGDL

GTYVINKQTP NKQIWLSSPS SGPKRYDWTG

KNWVYSHDGV SLHELLAAEL TKALKTKLDL

SSLAYSGKDA
```

A TAT-GG-hFXN fusion protein was developed for use in a protein replacement therapy for the treatment of Friedreich's Ataxia (FRDA). The TAT-GG-hFXN fusion protein has been shown to rescue disease phenotypes associated with FRDA in cells and animals. It is believed that the TAT-GG-hFXN fusion protein, when inside a cell, is localized to mitochondria.

Figure 3:
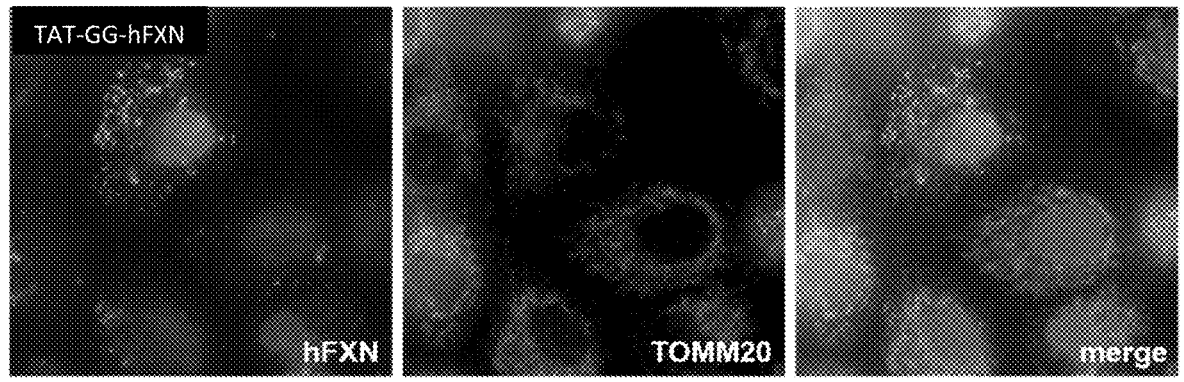
FIG. 3 is a panel of photographs of rat L6 myoblasts after treatment with a TAT-GG-hFXN fusion protein (5 µM) and immunofluorescent labeling with anti-hFXN antibodies (left panel) or mitochondria-specific anti-TOMM20 antibodies (middle panel). The right panel shows the merge of the anti-hFXN and anti-TOMM20 labels.

Subcellular localization of hFXN in rat L6 myoblasts following treatment with TAT-GG-hFXN fusion protein was evaluated through immunofluorescence microscopy (FIG. 3). Briefly, rat L6 myoblasts were treated with TAT-GG-hFXN fusion protein (5 µM) in serum-free medium for 2 hours. After 2 hours, the serum-free medium containing TAT-GG-hFXN fusion protein was replaced with complete medium, and the cells were incubated. As shown in FIG. 3, hFXN was strongly detected within small punctate intracellular vesicles as well as within the nucleus (FIG. 3, see panels "hFXN" and "merge"). The observed intracellular vesicles containing hFXN do not significantly overlap with the mitochondrial membrane marker TOMM20 (shown in FIG. 3, panel "merge"). These vesicles may represent trafficking of the TAT-GG-hFXN fusion protein through the endosomal/lysosomal system following its uptake by the cells, but further studies are required to prove this hypothesis. Together, these data demonstrate that hFXN can be detected in cells and that hFXN is strongly detected in the nucleus following treatment with the TAT-GG-hFXN fusion protein. Although low levels of hFXN may be present in the mitochondria following treatment with the TAT-GG-hFXN fusion protein under the described conditions, mitochondrial hFXN is practically undetectable in rat L6 myoblasts by immunofluorescence staining.

Figure 4:
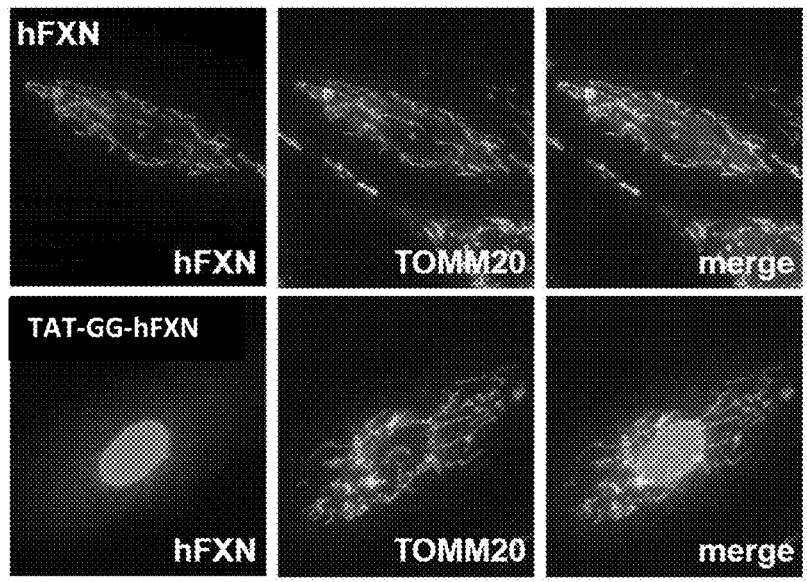
FIG. 4 is a panel of photographs of rat L6 myoblasts transfected with plasmids encoding hFXN (top panel) or a TAT-GG-hFXN fusion protein (bottom panel) after immunofluorescent labelling. The myoblasts were labelled with anti-hFXN antibodies (left panels) or anti-TOMM20 antibodies (middle panels). The right panels shows the merge of the two labels.

Comparison Between Subcellular Localization of hFXN in Rat L6 Myoblasts Following Transfection with hFXN or TAT-GG-hFXN Fusion Protein Under the above-described conditions, hFXN was detected mostly in the nucleus of rat L6 myoblasts following treatment with TAT-GG-hFXN fusion protein (FIG. 3). It is possible that the N-terminal TAT-GG sequence appended to full-length hFXN may direct the therapeutic protein into the nucleus following its internalization into cells. To more carefully assess this effect of TAT-GG on hFXN, subcellular localization of intracellularly expressed TAT-GG-hFXN fusion protein compared to hFXN in rat L6 myoblasts was detected and compared by immunofluorescence microscopy. Rat L6 myoblasts were transfected with expression plasmids containing genetic constructs encoding TAT-GG-hFXN fusion protein or $hFXN_{1-210}$ using lipid-based transfection reagents known to the person skilled in the art of transfections, such as for example the L6 Cell Avalanche™ system (from EZ Biosystems). After 24 hours, transfected cells were fixed using 4% paraformaldehyde and stained using antibodies against hFXN or the mitochondrial membrane marker TOMM20, as well as the Hoechst 33342 nuclear stain. As expected, rat L6 myoblasts transfected with the $hFXN_{1-210}$ construct were positive for the presence of mitochondrial hFXN, as evidenced by clear co-localization with the mitochondrial membrane marker TOMM20 (FIG. 4, top panel, "merge"). In contrast, rat L6 myoblasts transfected with TAT-GG-hFXN fusion protein stained positively for hFXN throughout the cell cytosol and strongly within the nucleus (FIG. 4, bottom panel, "merge"). In a very low percentage of cells transfected with TAT-GG-hFXN fusion protein, hFXN was detected in the mitochondria as well (very scarce co-localization staining in FIG. 4, bottom panel, "merge"). Taken together, these data demonstrate that TAT-GG-hFXN fusion protein subcellular localization is different from hFXN's native subcellular localization, going from predominantly mitochondrial (hFXN) to cytosolic and strongly nuclear (TAT-GG-hFXN fusion protein).

Example 2. Design of Novel TAT-GG-hFXN Constructs for Enhanced Delivery of hFXN to the Mitochondria The described fluorescence co-localization results shown in Example 1, FIG. 3 and FIG. 4 indicate that the great majority of TAT-GG-hFXN fusion protein molecules in the cells do not specifically localize to the mitochondria, and this may be due to the presence of the appended TAT-GG sequence at the amino-terminus of the molecule. In order to overcome this hurdle, several novel frataxin fusion proteins were designed and tested for their mitochondria delivery yields. Improved yields of mitochondrial delivery of therapeutic fusion proteins which act in the mitochondria will also provide better treatment of mitochondrial diseases, such as, for example, FRDA. To achieve this goal, novel fusion proteins were designed, and a schematic of the proteins is presented in FIG. 5, panels a-c.

One group of proteins was designed to include protease-cleavable domains, and a library of constructs encoding "protease activatable" cell-permeant hFXN fusion proteins was generated. These constructs comprised a sequence encoding a cell penetrating peptide (CPP), such as HIV-TAT (YGRKKRRQRRR; SEQ ID NO. 11) peptide, fused to an amino acid sequence that can be cleaved by an endogenous intracellular protease, and immediately followed by the protein of interest, in the present case full-length precursor hFXN. A di-peptide GG was used as a linker between the CPP and the proteolytic cleavage domain. Cleavage of TAT-GG from the fusion protein in the cytosol will result in a TAT-free hFXN protein which can then be imported into the mitochondria by virtue of its endogenous MTS. By way of example, cleavable intracellular protease-sensitive proteins used were SUMO-1 (cleaved by SUMO protease) and ubiquitin (cleaved by ubiquitinase), and proteolytically-sensitive peptides were DEVD (caspase cleavage site, SEQ ID NO: 19), EPLFAERK (SEQ ID NO: 20), and LLVY (calpain cleavage sites, SEQ ID NO: 21).

An alternative group of proteins was designed to include a nuclear exportation signal (NES), and in that way avoid accumulation of the protein of interest in the cellular nucleus. Thus, constructs were designed to include a CPP, linked to the protein of interest, linked to a NES. By way of example, the carboxyl-terminus of TAT-GG-hFXN fusion constructs was directly fused to a nuclear exportation signal (NES), such as NES domains derived from PKIα (NES1) and MAPKK (NES2).

Figure 5:
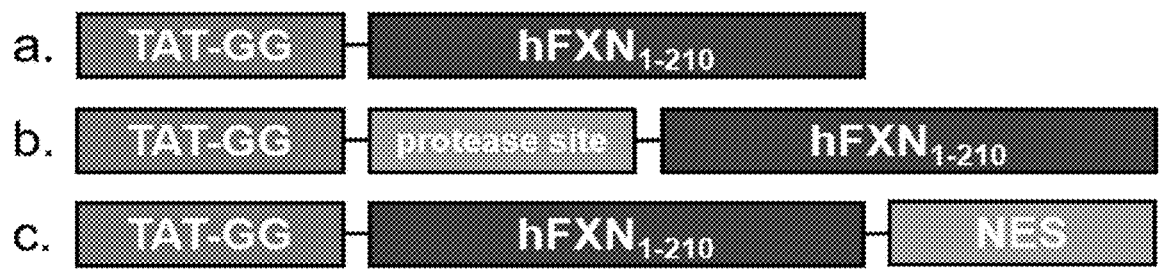
FIG. 5, Panels A-C present a schematic illustrating the design of the exemplary fusion proteins of the present disclosure comprising hFXN. Panel A shows TAT-GG fused to the amino-terminus of $hFXN_{1-210}$ (a TAT-GG-hFXN fusion protein). Panel B shows TAT-GG fused to a proteolytically-sensitive amino acid sequence followed by $hFXN_{1-210}$. Panel C shows TAT-GG fused to $hFXN_{1-210}$ and followed by a nuclear exportation signal (NES); in accordance with an embodiment of the disclosure.

A schematic of the fusion proteins is provided in FIG. 5, panels a-c, and a summary of the fusion protein constructs is provided in Table 11.

TABLE 11

Novel TAT-FNX fusion proteins.

| Fusion Protein | SEQ ID NO. | CPP | Protease cleavable domain or NES | Protease responsible for cleavage | Protein of interest |
|---|---|---|---|---|---|
| TAT-GG-SUMO1-hFXN | 55 | TAT | Sumo1 | SUMO | FXN |
| TAT-GG-Ubiquitin-hFXN | 56 | TAT | Ubiquitin | Deubiquitinase | FXN |

TABLE 11-continued

Novel TAT-FNX fusion proteins.

| Fusion Protein | SEQ ID NO. | CPP | Protease cleavable domain or NES | Protease responsible for cleavage | Protein of interest |
|---|---|---|---|---|---|
| TAT-GG-DEVD-hFXN | 57 | TAT | DEVD (SEQ ID NO: 19) | Caspase | FXN |
| TAT-GG-EPLFAERK-hFXN | 58 | TAT | EPLFAERK (SEQ ID NO: 20) | Calpain1 | FXN |
| TAT-GG-LLVY-hFXN | 59 | TAT | LLVY (SEQ ID NO: 21) | Calpain | FXN |
| TAT-GG-hFXN-NES1 | 60 | TAT | NES1 | not relevant | FXN |
| TAT-GG-hFXN-NES2 | 61 | TAT | NES2 | not relevant | FXN |

Example 3. Intracellular Expression of hFXN Fusion Proteins—Preliminary Screen for Mitochondrial Transport Genetic constructs encoding the various hFXN variants hFXN, TAT-GG-hFXN (TAT-hFXN fusion protein), TAT-GG-SUMO1-hFXN, TAT-GG-Ubiquitin-hFXN, TAT-GG-DEVD-hFXN, TAT-GG-EPLFAERK-hFXN, TAT-GG-LLVY-hFXN, TAT-GG-hFXN-NES1 and TAT-GG-hFXN-NES2 were cloned into expression vectors. By way of example, plasmid vector pcDNA3.1(+) (Genscript®, Piscataway, NJ) was used. All protein-encoding sequences were codon optimized for mammalian (human) expression. Amino acid sequences of the variants and their respective encoding nucleic acid sequences are provided in Tables 9 and 10 elsewhere in this disclosure.

Rat L6 myoblasts were transfected with the expression plasmids using lipid-based transfection reagents known to the person skilled in the art of transfections, e.g., using the L6 Cell Avalanche™ system (from EZ Biosystems). hFXN subcellular localization was detected by immunofluorescence microscopy, performed as described in Example 1. Transfected cells were cultured for 24 hours, after which cells were fixed using 4% paraformaldehyde and stained using antibodies against hFXN and the mitochondrial membrane marker TOMM20. In addition, the nuclei of the cells were stained using the Hoechst 33342 nuclear stain.

Figure 6:
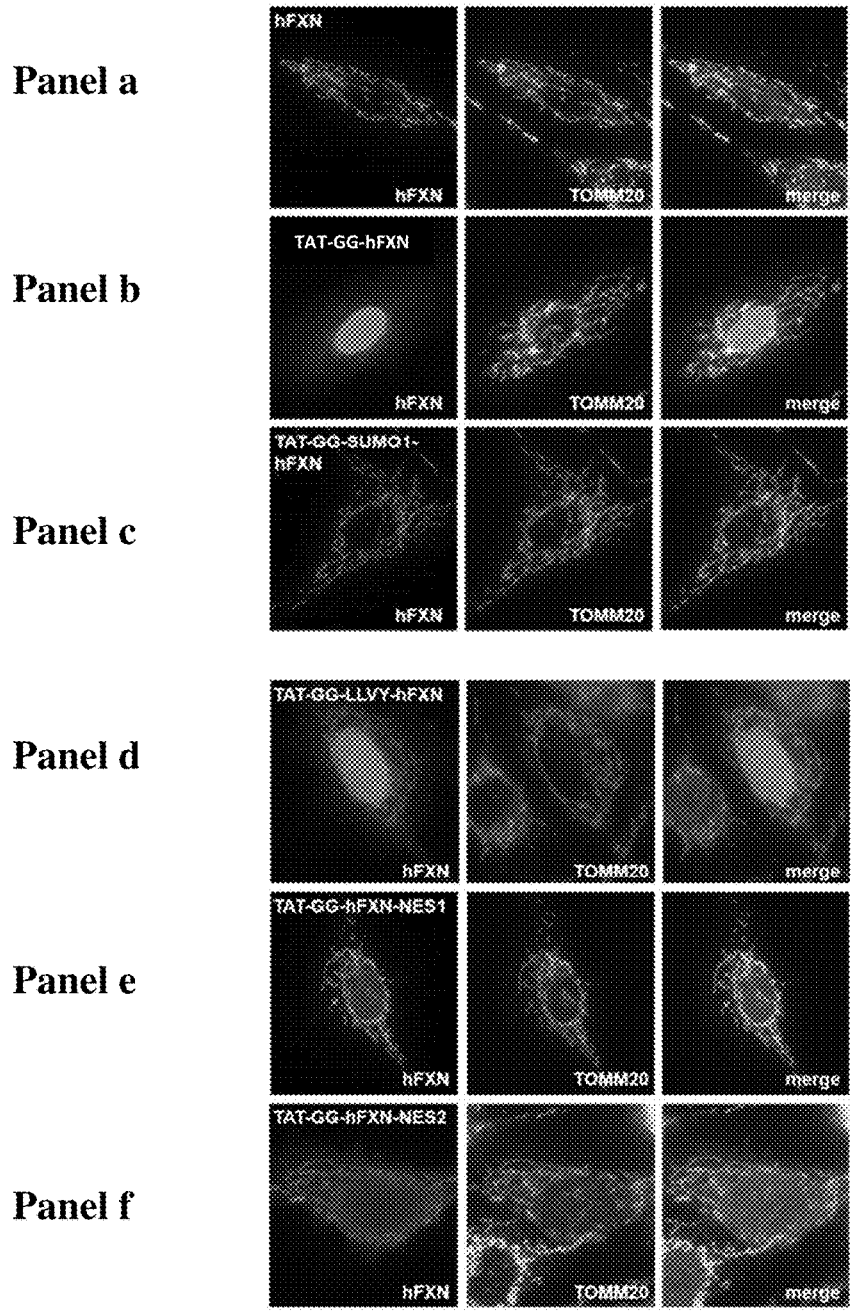
FIG. 6, Panels A-I are photographs of immunofluorescently labeled rat L6 myoblasts transfected with plasmids encoding hFXN (FIG. 4A), a TAT-GG-hFXN fusion protein (FIG. 4B), TAT-GG-SUMO1-hFXN (FIG. 4C), TAT-GG-LLVY-hFXN (FIG. 4D), TAT-GG-hFXN-NES1 (FIG. 4E), TAT-GG-hFXN-NES2 (FIG. 4F), TAT-GG-Ubiquitin-hFXN (FIG. 4G), TAT-GG-DEVD-hFXN (FIG. 4H), and TAT-GG-EPLFAERK-hFXN (FIG. 4I). For immunofluorescent labeling, the L6 myoblasts were stained with antibodies against hFXN (left panel) and TOMM20 (middle panel). The right panel shows the merge of the two labels.
Figure 6:
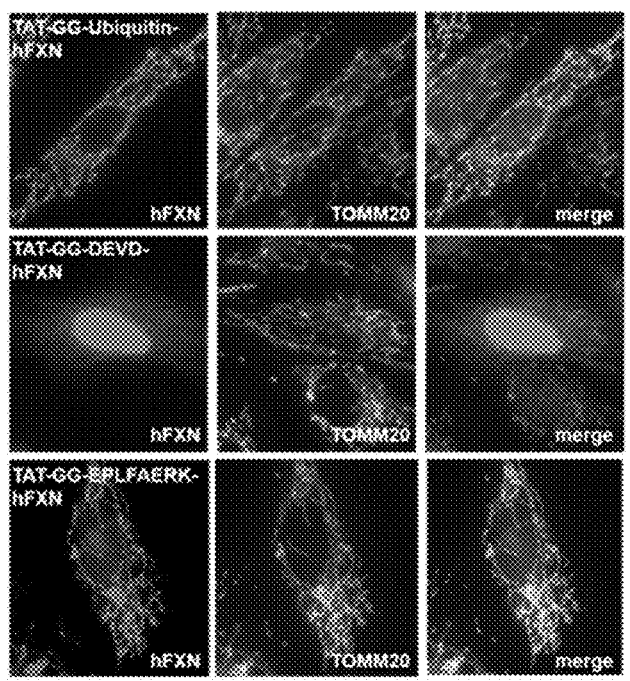

The results of the immunolabeling are presented in FIG. 6, Panels a-i and summarized in Table 12.

TABLE 12

Localication of hFXN and FXN fusion protein variants.

| Construct | Intracellular Localization |
|---|---|
| hFXN | Mitochondria |
| TAT-GG-hFXN fusion protein | Nucleus (mostly) |
| TAT-GG-SUMO1-hFXN | Mitochondria |
| TAT-GG-Ubiquitin-hFXN | Mitochondria |
| TAT-GG-DEVD-hFXN | Cytosol and nucleus |
| TAT-GG-EPLFAERK-hFXN | Mitochondria, cytosol and nucleus |
| TAT-GG-LLVY-hFXN | Mitochondria, cytosol and nucleus |
| TAT-GG-hFXN-NES1 | Mitochondria, cytosol and nucleus |
| TAT-GG-hFXN-NES2 | Mitochondria, cytosol and nucleus |

As demonstrated in Example 1, when expressed in rat L6 myoblasts, hFXN localized to the mitochondria, whereas TAT-GG-hFXN fusion protein was predominantly detected in the cytosol and nucleus. In cells transfected with TAT-GG-SUMO1-hFXN and TAT-GG-Ubiquitin-hFXN, hFXN was detected in the mitochondria. In cells transfected with TAT-GG-DEVD-hFXN, hFXN was detected in the cytosol and nucleus, and no significant mitochondrial localization was observed. In cells transfected with TAT-GG-EPLFAERK-hFXN and TAT-GG-LLVY-hFXN, hFXN was detected in the mitochondria as well as within the cytosol and nucleus. Taken together, these data demonstrate that intracellular SUMO proteases, deubiquitinases, as well as intracellular calpains were able to cleave the fusion proteins at their respective cleavage sites and to yield a variant of hFXN that localizes to the mitochondria. Similar to TAT-GG-hFXN fusion protein, TAT-GG-DEVD-hFXN was not detected in mitochondria, suggesting that caspase-mediated cleavage of DEVD (SEQ ID NO: 19) was inefficient under the current conditions.

In cells transfected with TAT-GG-hFXN-NES1 and TAT-GG-hFXN-NES2, hFXN was detected in the mitochondria as well as within the cytosol and nucleus. Together, these data demonstrate that nuclear exportation of hFXN fusion proteins results in improved mitochondrial import of hFXN.

Example 4: Assessment of hFXN Maturation by Western Blot Analysis

In its native state, full-length $hFXN_{1-210}$ is directed to the mitochondria by its N-terminal mitochondrial targeting sequence (MTS), where it is imported and proteolytically processed in two steps to yield the mature form of the protein, the hFXN$_{81-210}$ fragment. In order to evaluate the extent of hFXN maturation by proteolytic processing of the novel hFXN variants, Western blot analysis was performed in hFXN variants generated in rat L6 myoblasts transfected with the respective expression plasmids containing genes encoding hFXN, TAT-GG-hFXN fusion protein, TAT-GG-SUMO1-hFXN, TAT-GG-Ubiquitin-hFXN, TAT-GG-EPL-FAERK-hFXN, TAT-GG-LLVY-hFXN, TAT-GG-hFXN-NES1, and TAT-GG-hFXN-NES2. Cells were harvested 72 hours after transfection, lysed in ice-cold radioimmunoprecipitation assay (RIPA) buffer supplemented with protease inhibitors and EDTA. The cell lysates were separated by SDS-PAGE (sodium dodecyl sulfate polyacrylamide gel electrophoresis), transferred onto a nitrocellulose membrane, and analyzed by Western Blot using a commercial antibody against hFXN (purchased from AbCam), as well as an antibody against β-Actin as a loading control.

Figure 7:
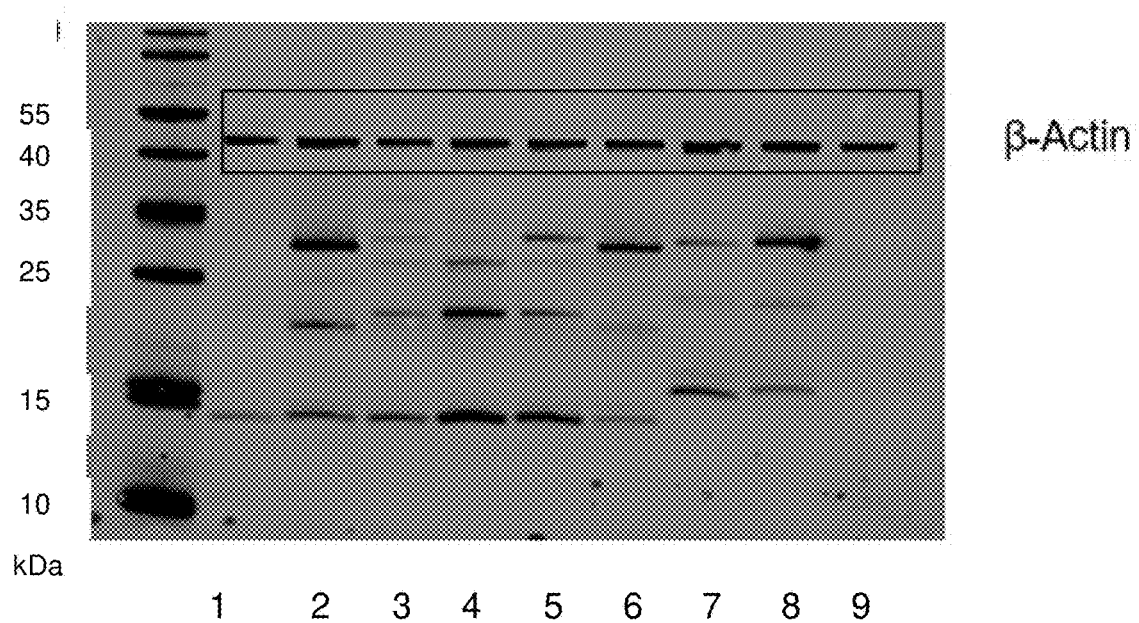
FIG. 7 is a photograph of a Western blot analysis of cell lysates from rat L6 myoblasts transfected with hFXN variants hFXN (Lane 1), a TAT-GG-hFXN fusion protein (Lane 2), TAT-GG-SUMO1-hFXN (Lane 3), TAT-GG-Ubiquitin-hFXN (Lane 4), TAT-GG-EPLFAERK-hFXN (Lane 5), TAT-GG-LLVY-hFXN (Lane 6), TAT-GG-hFXN-NES1 (Lane 7), TAT-GG-hFXN-NES2 (Lane 8) and Mock (Lane 9). The blot was labelled with anti-hFXN antibody and β-actin was used as a control.

The results are presented in FIG. 7. Fully mature hFXN (lane 1, band below 15 kDa marker, ~14.2 kDa) was detected in lysate obtained from cells transfected with hFXN construct. A band corresponding to mature hFXN (~14.2 kDa) was also detected in lysate obtained from cells transfected with a plasmid encoding TAT-GG-hFXN fusion protein (lane 2) and TAT-GG-SUMO1-hFXN (lane 3). Mature hFXN was detected in higher amounts in lysates obtained from cells transfected with TAT-GG-Ubiquitin-hFXN (lane 4), TAT-GG-EPLFAERK-hFXN (lane 5), and TAT-GG-hFXN-NES1 (lane 7, where hFXN-NES1 migrated slower by SDS-PAGE as the appended NES1 increases the molecular weight by ~1 kDa). A band corresponding to mature hFXN was also detected in TAT-GG-LLVY-hFXN (lane 6), and TAT-GG-hFXN-NES2 (lane 8). These results indicate that the novel constructs TAT-GG-Ubiquitin-hFXN, TAT-GG-EPLFAERK-hFXN, and TAT-GG-hFXN-NES1 are proteolytically processed in cells and yield higher amounts of mature hFXN than TAT-GG-hFXN fusion protein.

Example 5. Transduction of Schwann Cells with hFXN Fusion Proteins

The goal of this experiment was to determine and compare the ability of different hFXN fusion proteins to transduce cells.

Figure 8:
FIG. 8 is a schematic representation of the structure of hFXN fusion proteins of the present disclosure tested for their cell transduction ability in Example 5.
Figure 8:
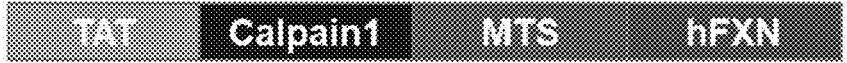
Figure 8:
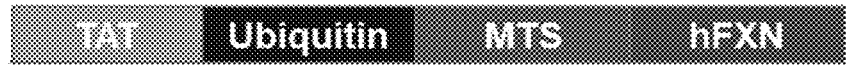
Figure 8:

This experiment utilized the TAT-GG-hFXN fusion protein described in Example 1 and the novel TAT-FXN fusion proteins: TAT-GG-Ubiquitin-hFXN (SEQ ID NO: 56) and TAT-GG-EPLFAERK-hFXN (SEQ ID NO: 58). In TAT-GG-EPLFAERK-hFXN (SEQ ID NO: 58), EPLFAERK (SEQ ID NO: 20) is a Calpain1 sensitive sequence. The schematic structure of the fusion proteins used in the experiment is shown in FIG. 8.

The experiment utilized Schwann cells because these cells grow relatively fast, and are easy to transduce. Also, endogenous levels of hFXN in these cells are below the detection limit and, therefore, are not expected to interfere with the signal produced by the TAT-GG-hFXN fusion proteins.

Schwann cells were plated at a seeding density of 8,000 cells per well in a 96-well plate 20 (Corning 3904) and incubated overnight at 37° C. On day 1, solutions were prepared containing 1.25 µM, 1 µM and 0.5 µM of each TAT-GG-hFXN fusion protein in transduction media containing DMEM, 1% heat inactivated FBS and 20 mM glycerol. Cells were washed with 150 µL of PBS per well, and then 60 µL of TAT-GG-hFXN solution or transduction media alone for negative control were added per well. The cells were incubated at 37° C. for 2 hours, after which 60 µL of complete media containing DMEM, 10% FBS and 1% antibiotic:antimycotic (Gemini bioprodut 400-101) were added per well, and the cells were incubated overnight at 37° C.

The same treatment was repeated on day 2. On day 3, cells in each well were washed with 150 µL of PBS, after which the cells were trypsinized by adding 50 µL of TrypLE (Gibco™ 12604021) to each well and incubating at 37° C. for 5 minutes. After this, the trypsinization reaction was quenched by addition to each well of 50 µL of complete medium. The cells were re-suspended and transferred to a fibronectin-coated glass-bottom plate (Corning 4584) containing 40 µL of complete DMEM per well. The cells were allowed to settle overnight at 37° C.

On day 4, the cells were washed with PBS, after which 50 µL of freshly prepared 4% paraformaldehyde solution was added to each well, and the cells were incubated at room temperature for 10 minutes. Subsequently, the cells were washed twice with 150 µL PBS per well and then 50 µL of blocking buffer (0.3% Triton-X 100, 5% normal goat serum in PBS) was added per well. The cells were incubated at room temperature for 1 hour, after which the blocking buffer was removed, and 50 µL of primary antibody diluted in blocking buffer (Anti-Frataxin Antibody ab110328 from abcam and anti-TOMM20 antibody ab78547 from abcam) was added to each well. The Anti-Frataxin antibody was diluted 1:600, while the TOMM20 antibody was diluted 1:300. The cells were incubated overnight at 4° C.

On day 5, the cells were washed twice with 120 µL of PBS per well, and 50 µL of secondary antibody diluted in blocking buffer was added to each well (Anti-Mouse IgG AlexaFluor594, ab150116 from abcam and Anti-rabbit igG Alexafluor488, ab150077 from abcam). Each antibody was diluted 1:1000. The cells were incubated at room temperature for one hour, washed with 150 µL of PBS per well, and were stained by adding 50 µL of 300 nM Hoescht 33342 stain per well and incubating for 3 minutes at room temperature. Subsequently, the cells were washed with PBS.

The cells were imaged using a Lionheart microscope. Human FXN was detected using an Alexa-594-labeled goat anti-mouse IgG secondary antibody that bound to the mouse anti-hFXN monoclonal primary antibody. Mitochondrial membrane was detected using an Alexa-488-labelled goat anti-rabbit IgG secondary antibody that bound to the anti-TOMM20 polycolonal primary antibody.

Figure 9:
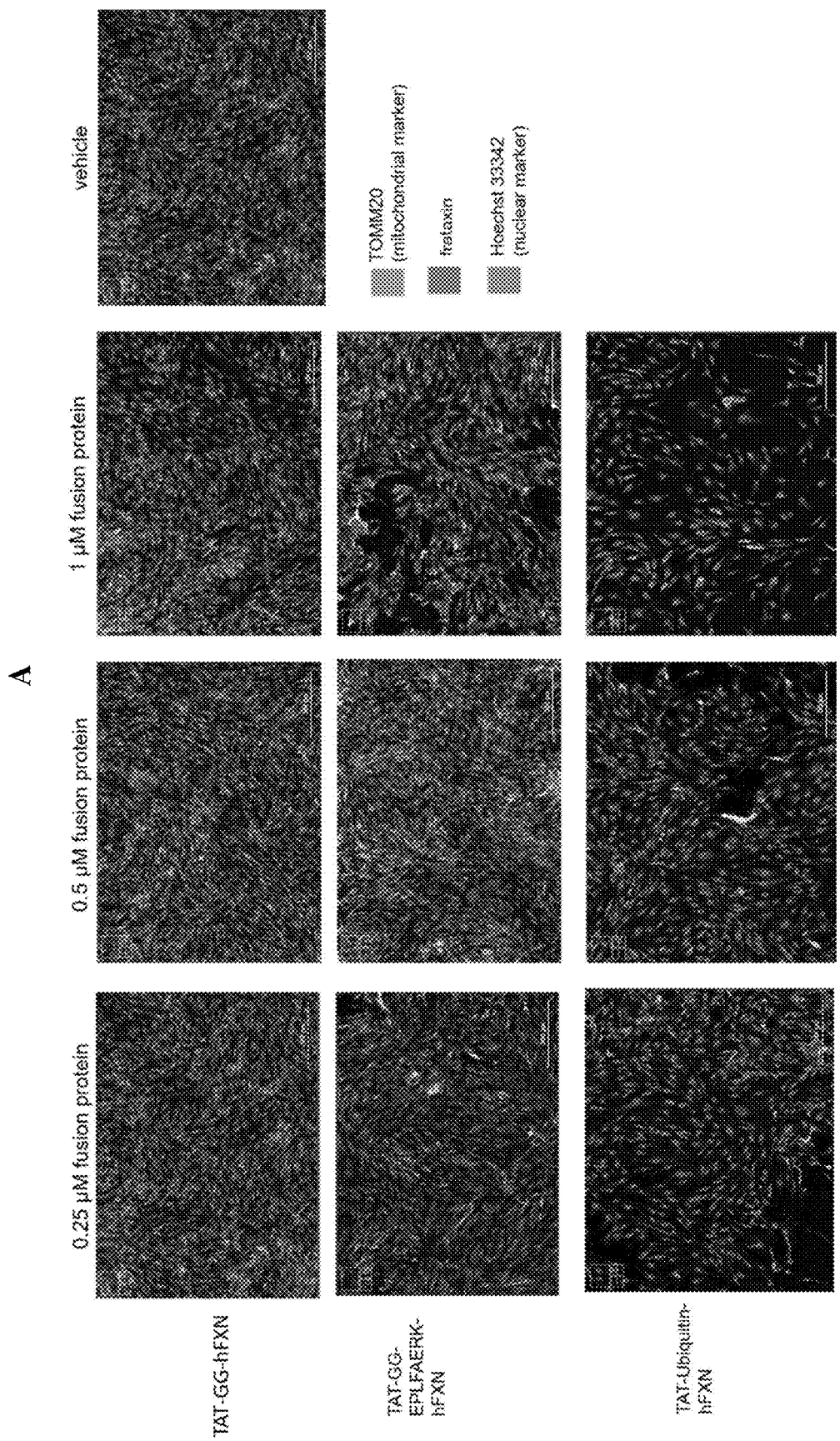
FIG. 9, Panel A is a series of photographs of Schwann cells treated with 0.25 µM, 0.5 µM and 1 µM TAT-GG-hFXN, TAT-GG-EPLFAERK-hFXN, TAT-GG-Ubiquitin-hFXN and vehicle as a negative control. In the photographs, the green color corresponds to the TOMM20 signal as a mitochondrial marker, the red color corresponds to hFXN signal and the blue color corresponds to the Hoechst 33342 dye signal as a nuclear marker.
Figure 9:
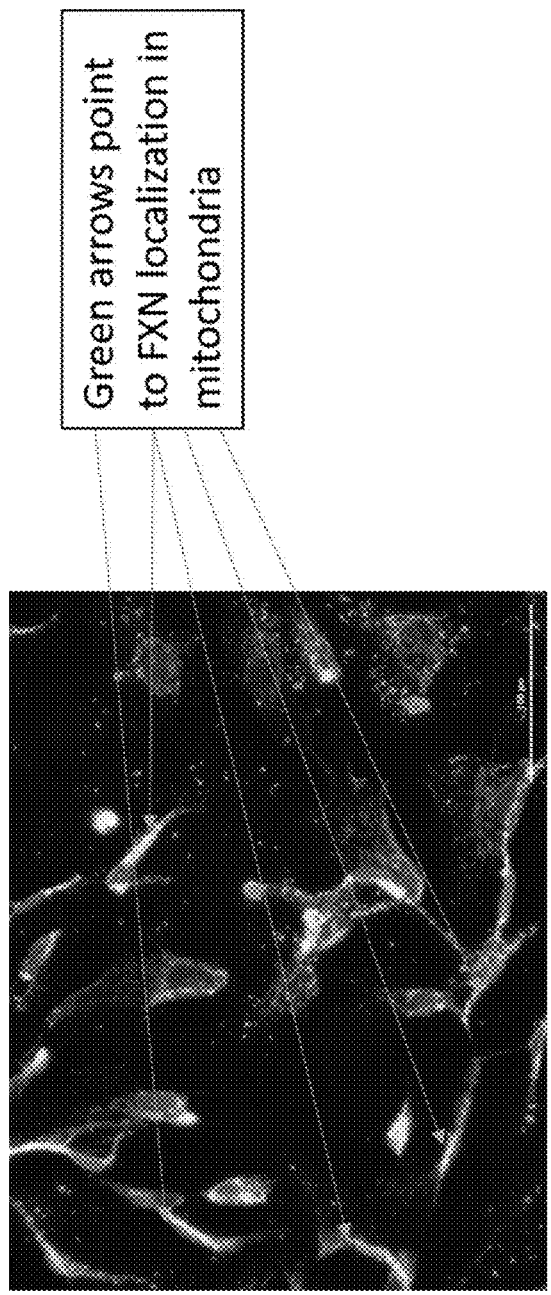
Figure 9:
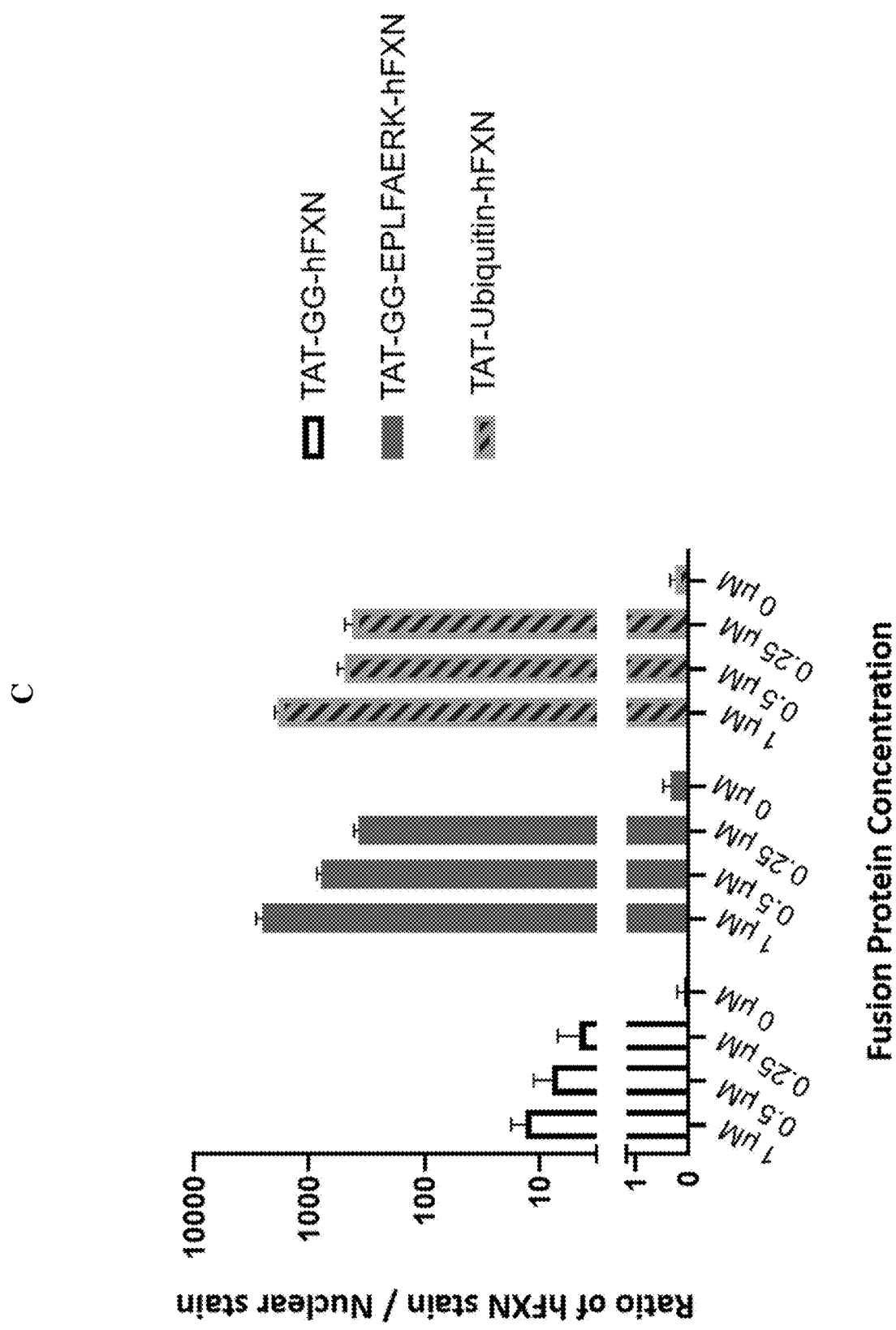
Figure 9:
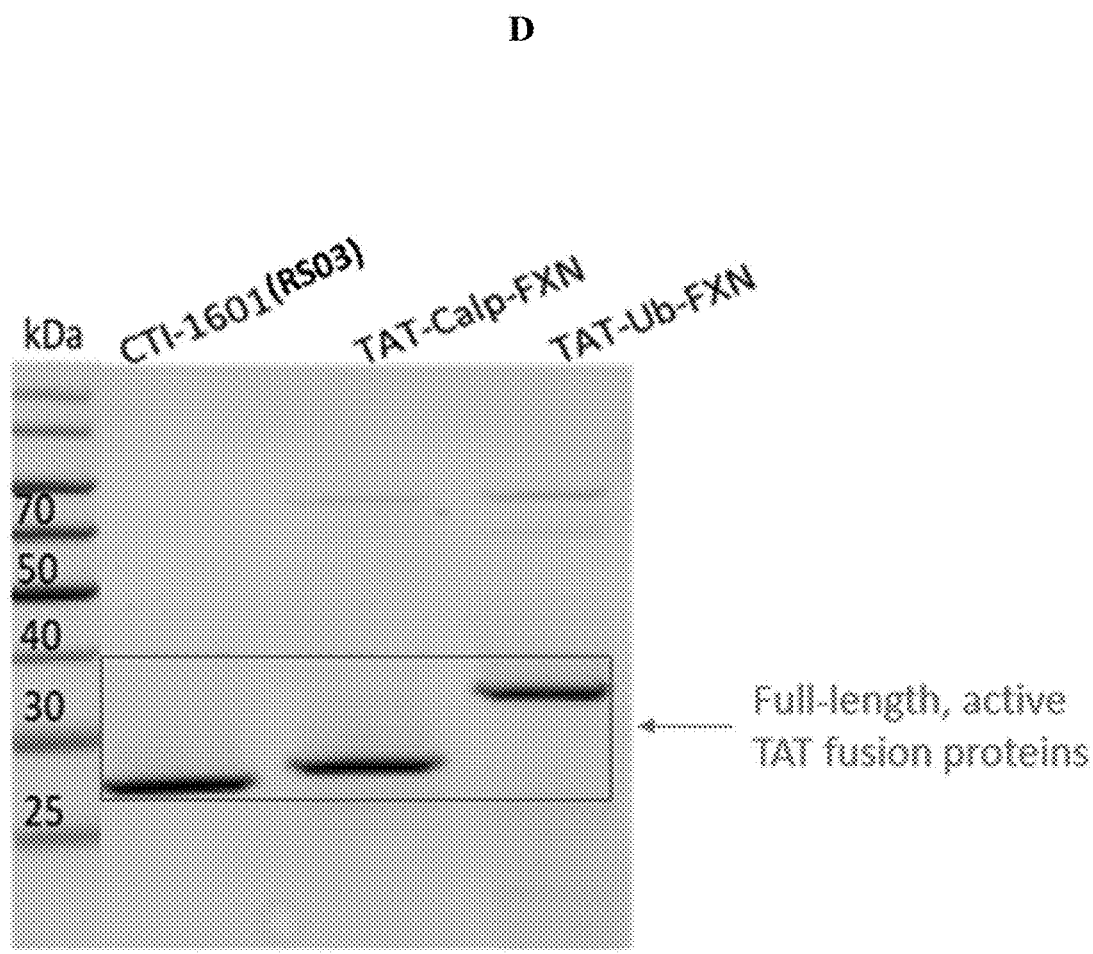

The results of the experiment are presented in FIG. 9. Specifically, FIG. 9, Panel A is a series of photographs of Schwann cells treated with 0.25 µM, 0.5 µM and 1 µM TAT-GG-hFXN, TAT-GG-EPLFAERK-hFXN, TAT-GG-Ubiquitin-hFXN and vehicle as a negative control. In the photographs, the green color corresponds to the TOMM20 signal as a mitochondrial marker, the red color corresponds to hFXN signal and the blue color corresponds to the Hoechst 33342 dye signal as a nuclear marker. Under the imaging conditions, endogenous frataxin levels are not detectable in the Schwann cells. As demonstrated by FIG. 9, Panel A, cells transduced with vehicle showed only nuclear and mitochondrial staining, but not hFXN staining. Cells transduced with TAT-GG-hFXN showed some hFXN staining. In contrast, cells transduced with TAT-GG-EPLFAERK-hFXN and TAT-GG-Ubiquitin-hFXN showed higher levels of hFXN staining at corresponding concentrations.

FIG. 9, Panel B is a high magnification image of cells treated with TAT-GG-Ubiquitin-hFXN fusion protein. This image shows the details of hFXN stain and its localization to mitochondria. This image indicates that in cells treated with novel hFXN fusion proteins, hFXN localizes to mitochondria.

The amount of hFXN signal in the photographs presented in FIG. 9 was quantified by determining the mean intensity of Texas red channel used to detect the signal associated with Alexa 594. The amount of the nuclear signal was quantified by determining the mean intensity of the DAPI channel used to detect the signal associated with the Hoechst 33342 dye.

FIG. 9, Panel C is a bar graph showing the ratios of mean hFXN stain signal to the mean nuclear stain signal for cells treated with various concentrations of TAT-GG-hFXN, TAT-GG-EPLFAERK-hFXN and TAT-GG-Ubiquitin-hFXN. The results presented in FIG. 9, Panel C indicate that the amount of hFXN detected in cells treated with novel fusion proteins of the present disclosure, i.e., TAT-GG-EPLFAERK-hFXN and TAT-GG-Ubiquitin-hFXN, is more than 2 orders of magnitude higher than the amount of hFXN detected in cells treated with TAT-GG-hFXN, at all concentrations studied.

To further ensure accuracy of quantification of hFXN in the microscopy experiments, the purified recombinant hFXN fusion proteins used in for cell transduction experiments were separated on an SDS-PAGE gel and transferred onto a nitrocellulose membrane. The membrane was stained with a total protein stain and visualized.

FIG. 9, Panel D is a picture of a nitrocellulose membrane following transfer from an SDS-PAGE gel loaded with samples of TAT-GG-hFXN, TAT-GG-EPLFAERK-hFXN, and TAT-GG-Ubiquitin-hFXN used for transduction experiments and stained for total protein. The results presented in FIG. 9, Panel D demonstrate that similar amounts of TAT-GG-hFXN, TAT-GG-EPLFAERK-hFXN and TAT-GG-Ubiquitin-hFXN are found in samples used for transfection. These results demonstrate a lack of fusion protein degradation and confirm that the same amount of each fusion protein was used in transduction experiments. These results also demonstrate that the quantification results seen in the microscopy experiments in FIG. 9, Panels A and B are not due to the differences in the amounts of hFXN fusion proteins added to the cells.

The results presented in FIG. 9, Panels A-D demonstrate that the amount of protein of interest, e.g., hFXN, detected in cells following transduction of cells with novel fusion proteins of the present disclosure comprising CPP and TES is significantly higher than the amount of protein of interest, e.g., hFXN, detected in cells following transduction of cells with fusion protein that comprises CPP but does not comprise TES. The results indicate that introducing TES into a fusion protein comprising CPP, such that the TES is located between CPP and the protein of interest, can significantly increase the amount of protein of interest in a cell.

Example 6. Transduction of Schwann Cells and H9C2 Cells with hFXN Fusion Proteins The goal of this experiment was to determine and compare the ability of hFXN to localize to mitochondria after transduction of cells with different hFXN fusion proteins.

This experiment utilized Schwann cells and H9C2 myoblast cells and the same hFXN fusion proteins used in Example 5 and illustrated in FIG. 8, i.e., TAT-GG-hFXN, TAT-GG-EPLFAERK-hFXN and TAT-GG-Ubiquitin-hFXN. The experiment utilized the same procedure described in Example 5 to treat the cells with the hFXN fusion proteins at fusion protein concentration of 0, 0.0625 µM, 0.125 µM, 0.25 µM, 0.5 µM. The cells were subsequently stained using an anti-FXN stain, nuclear stain and mitochondrial stain, and analyzed using microscopy as described in Example 5.

Figure 10:
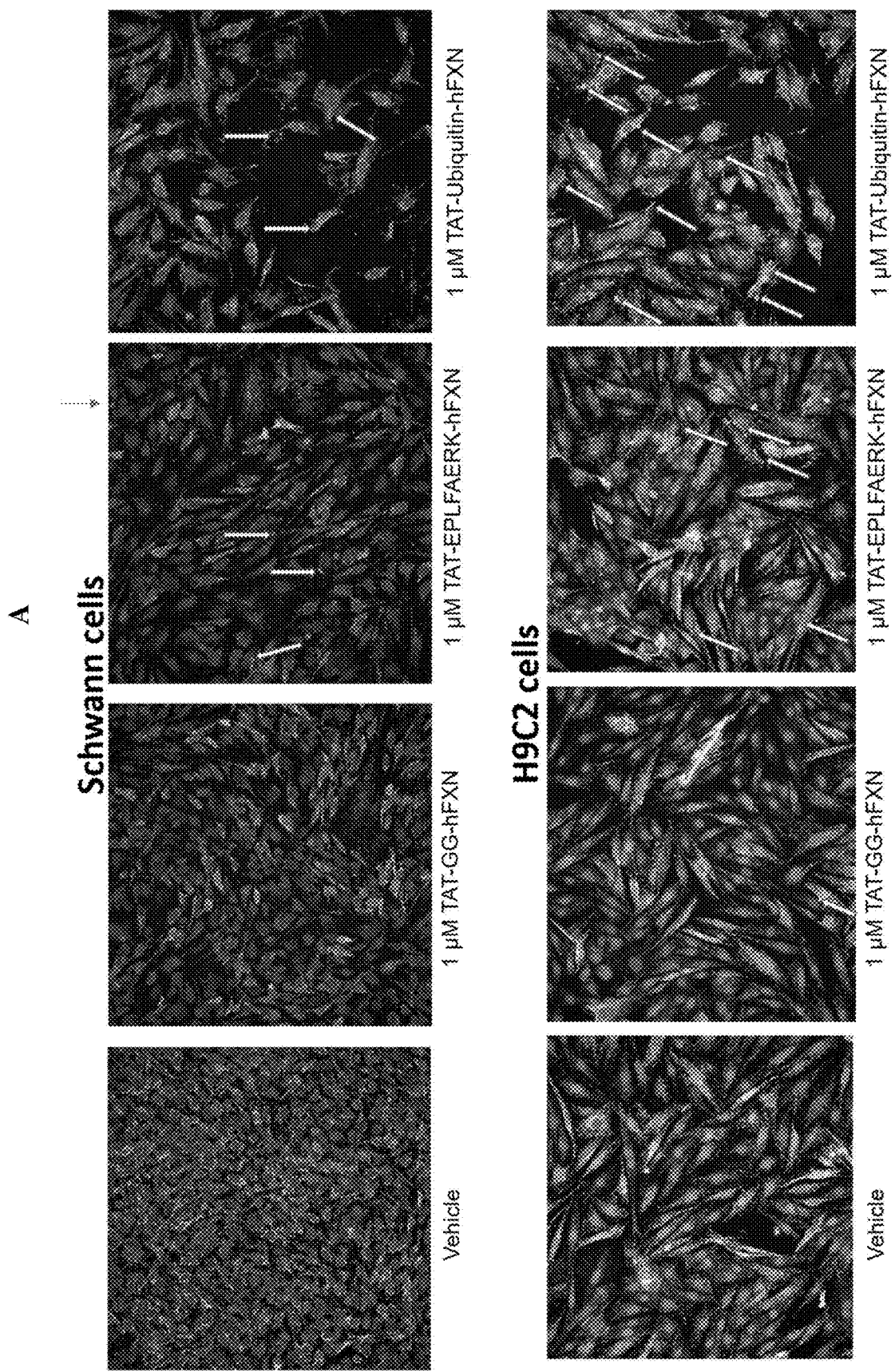
FIG. 10, Panel A is a series of representative photographs of Schwann and H9C2 cells treated with 1 μM hFXN fusion proteins TAT-GG-hFXN, TAT-GG-EPLFAERK-hFXN and TAT-GG-Ubiquitin-hFXN and stained with mitochondrial, nuclear and anti-FXN stains. The white errors show representative localication of hFXN to mitochondria.
Figure 10:
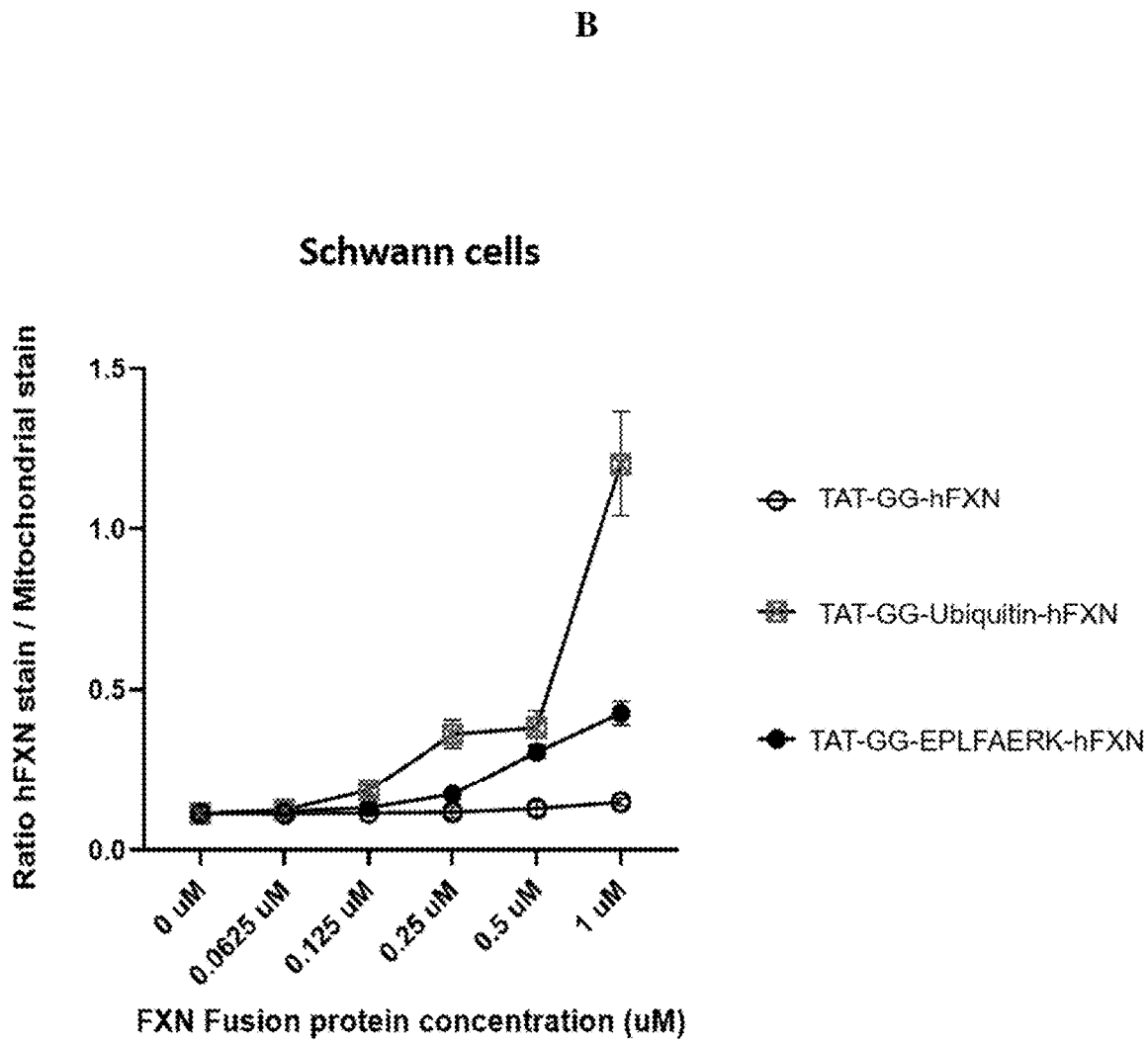
Figure 10:
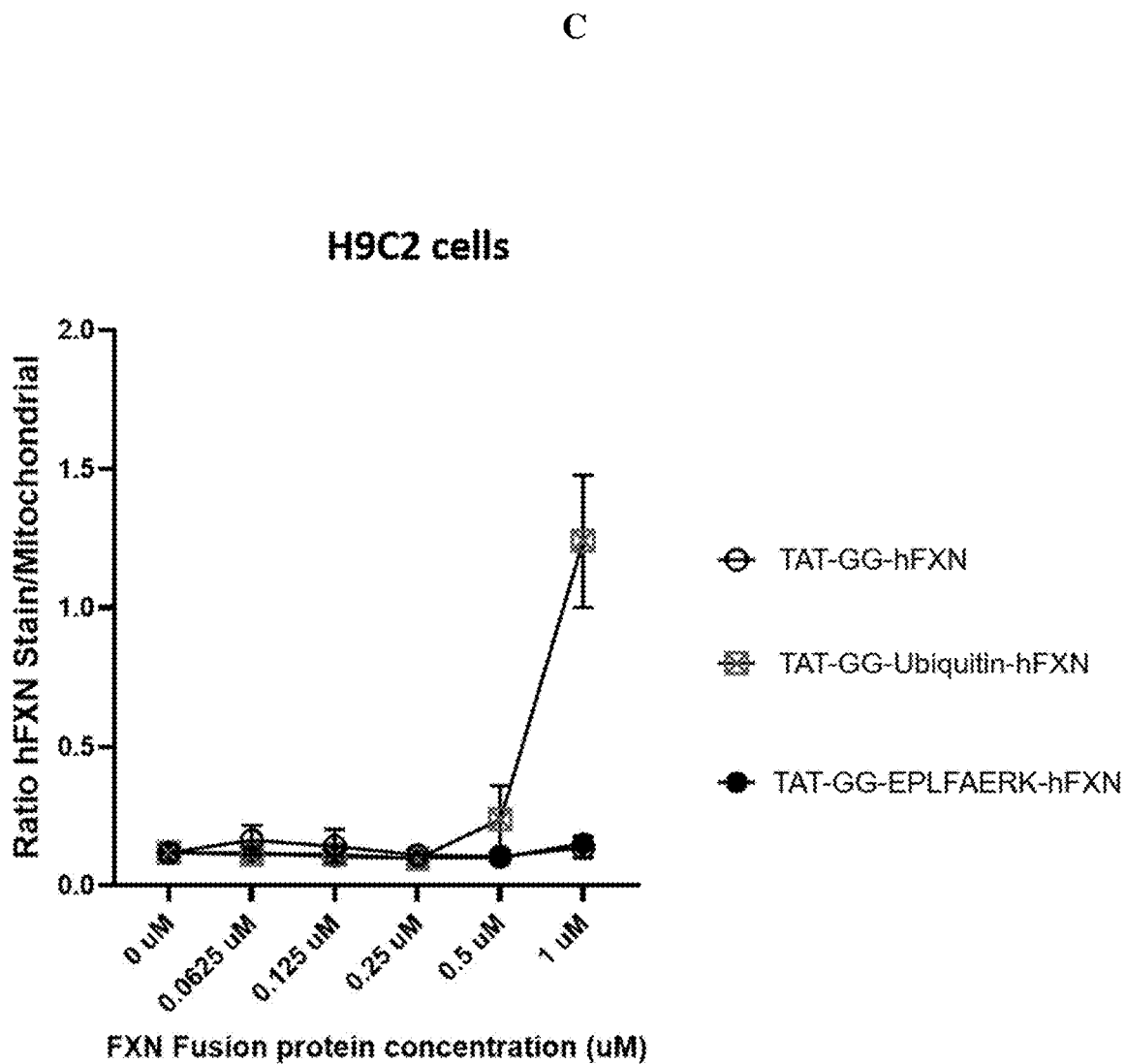
Figure 10:
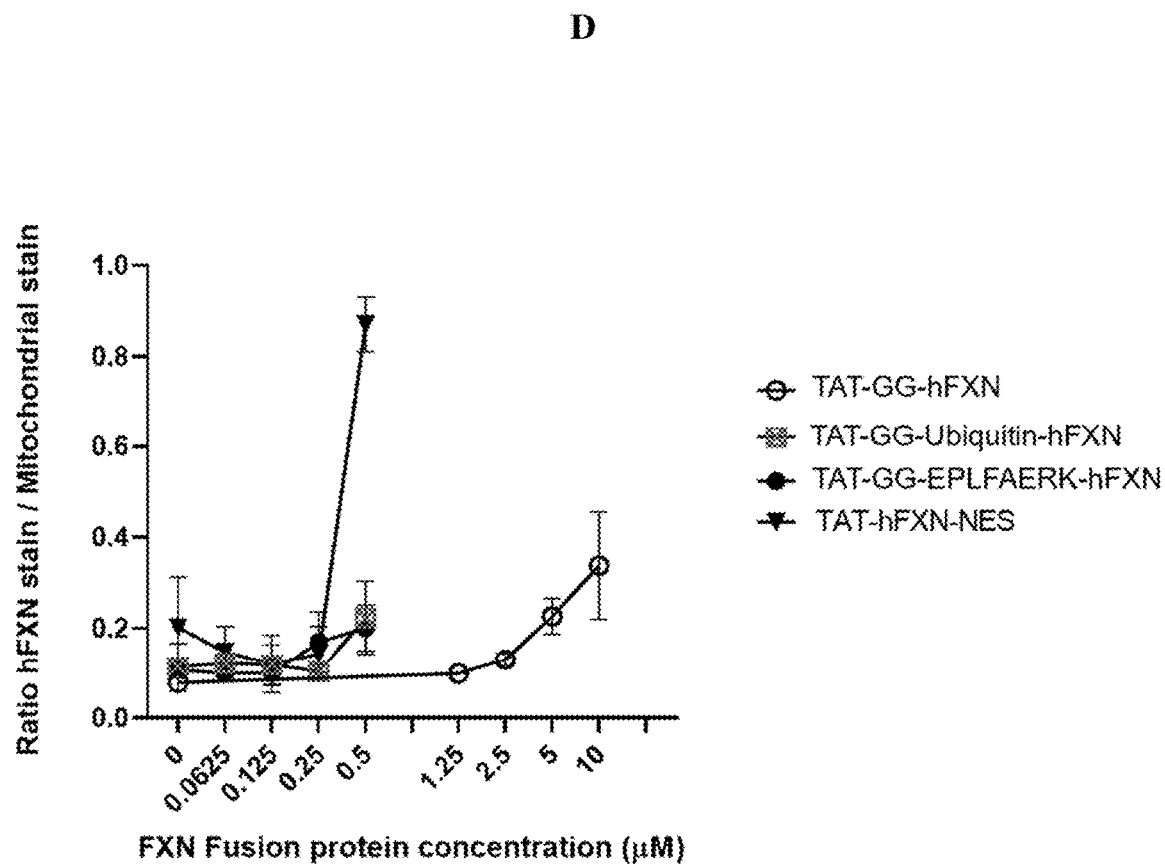

FIG. 10, Panel A is a series of representative photographs of Schwann and H9C2 cells treated with 1 µM hFXN fusion proteins and stained with mitochondrial, nuclear and anti-FXN stains. The white arrows show high level of representative localication of hFXN to mitochondria. The results shown in FIG. 10, Panel A indicate that the amount of hFXN in cells treated with 1 µM TAT-GG-EPLFAERK-hFXN and TAT-GG-Ubiquitin-hFXN is higher than the amount of hFXN in cells treated with TAT-GG-hFXN. The results also indicate that in cells treated with 1 µM TAT-GG-EPLFAERK-hFXN and TAT-GG-Ubiquitin-hFXN, hFXN localizes to mitochondria (see white arrows), while less mitochondrial localization of hFXN is observed in cells treated with 1 µM TAT-GG-hFXN.

The mean anti-FXN stain signal and the mean anti-mitochondrial stain signal were determined for each sample, and the ratio of the mean anti-FXN stain signal to the mean anti-mitochondrial stain signal (TOMM20) was calculated. FIG. 10, Panel B presents the ratio of the mean anti-FXN stain signal to the mean anti-mitochondrial stain signal graphed as a function of hFXN fusion protein concentration in Schwann cells. FIG. 10, Panel C presents the ratio of the mean anti-FXN stain signal to the mean anti-mitochondrial stain signal graphed as a function of hFXN fusion protein concentration in H9C2 cells. The results presented in FIG. 10, Panels B and C demonstrate that higher amounts of hFXN localize to mitochondria in Schwann cells and H9C2 cells treated with GG-EPLFAERK-hFXN and TAT-GG-Ubiquitin-hFXN, as compared to Schwann cells and H9C2 cells treated with TAT-GG-hFXN. Further, the amount of mitochondrial localization in cells treated with GG-EPLFAERK-hFXN and TAT-GG-Ubiquitin-hFXN is dose-dependent.

Another cell transfection experiment was conducted using Schwann cells and hFXN fusion proteins which included: TAT-GG-hFXN, TAT-GG-EPLFAERK-hFXN, TAT-GG-Ubiquitin-hFXN, and TAT-GG-hFXN NES1 (SEQ ID NO: 60 and depicted in FIG. 8). The experimental protocol used for the experiment was the same as described above. FIG. 10, Panel D presents the ratio of the mean anti-FXN stain signal to the mean anti-mitochondrial stain signal graphed as a function of hFXN fusion protein concentration in Schwann cells. The results presented in FIG. 10, Panel D demonstrate that higher amounts of hFXN localize to mitochondria in Schwann cells cells treated with TAT-GG-EPLFAERK-hFXN, TAT-GG-Ubiquitin-hFXN and TAT-GG-hFXN-NES1, as compared to Schwann cells and H9C2 cells treated with TAT-GG-hFXN. The results also demonstrate that at the fusion protein concentration of 0.5 µM, the amount of hFXN localized to mitochondria after treatment with TAT-GG-hFXN-NES1 is significantly higher than the amount of hFXN localized to mitochondria after treatment with TAT-GG-EPLFAERK-hFXN, TAT-GG-Ubiquitin-hFXN. Further, the amount of mitochondrial localization in cells treated with the novel hFXN fusion proteins is dose-dependent.

The results presented in FIG. 10, Panels A-D indicate that higher amounts of hFXN are detected in cells treated with novel fusion proteins of the disclosure, i.e., TAT-GG-EPLFAERK-hFXN, TAT-GG-Ubiquitin-hFXN and TAT-GG-hFXN-NES1, as compared to cells treated with TAT-GG-hFXN. The results also indicate that hFXN in cells treated with novel hFXN fusion proteins of the disclosure localize to mitochondria.

Example 7. Confirmation of Intracellular Processing of Novel hFXN Fusion Proteins The goal of this experiment was to confirm that the novel hFXN fusion proteins of the present disclosure are correctly processed by cellular machinery to yield the mature FXN protein. This experiment utilized L6 rat myoblast cells and the same hFXN fusion proteins used in Example 5 and illustrated in FIG. 8, i.e., TAT-GG-hFXN, TAT-GG-EPL-FAERK-hFXN and TAT-GG-Ubiquitin-hFXN. This experiment also utilized two additional hFXN fusion proteins as follows: TAT-GG-hFXN-NES1 (SEQ ID NO: 60) and TAT-GG-SUMO-hFXN (SEQ ID NO: 81). The amino acid sequence of TAT-GG-SUMO-hFXN (SEQ ID NO: 81) is shown below:

MYGRKKRRQRRRGGSDSEVNQEAKPEVKPEVKPETHINLKVSDGSSEIF

FKIKKTTPLRRLMEAFAKRQGKEMDSLRFLYDGIRIQADQTPEDLDMED

NDIIEAHREQIGGMWTLGRRAVAGLLASPSPAQAQTLTRVPRPAELAPL

CGRRGLRTDIDATCTPRRASSNQRGLNQIWNVKKQSVYLMNLRKSGTLG

HPGSLDETTYERLAEETLDSLAEFFEDLADKPYTFEDYDVSFGSGVLTV

KLGGDLGTYVINKQTPNKQIWLSSPSSGPKRYDWTGKNWVYSHDGVSLH

ELLAAELTKALKTKLDLSSLAYSGKDA.

For the experiment, L6 cells were transfected with DNA vectors encoding the hFXN fusion proteins, and the cells were incubated for 24 hours. The cells were collected and processed to isolate total protein which was then separated on an SDS-PAGE gel. After SDS-PAGE separation, frataxin in the gel was analyzed using Western blotting with anti-FXN antibody and anti-β actin antibodies for control.

Figure 11:
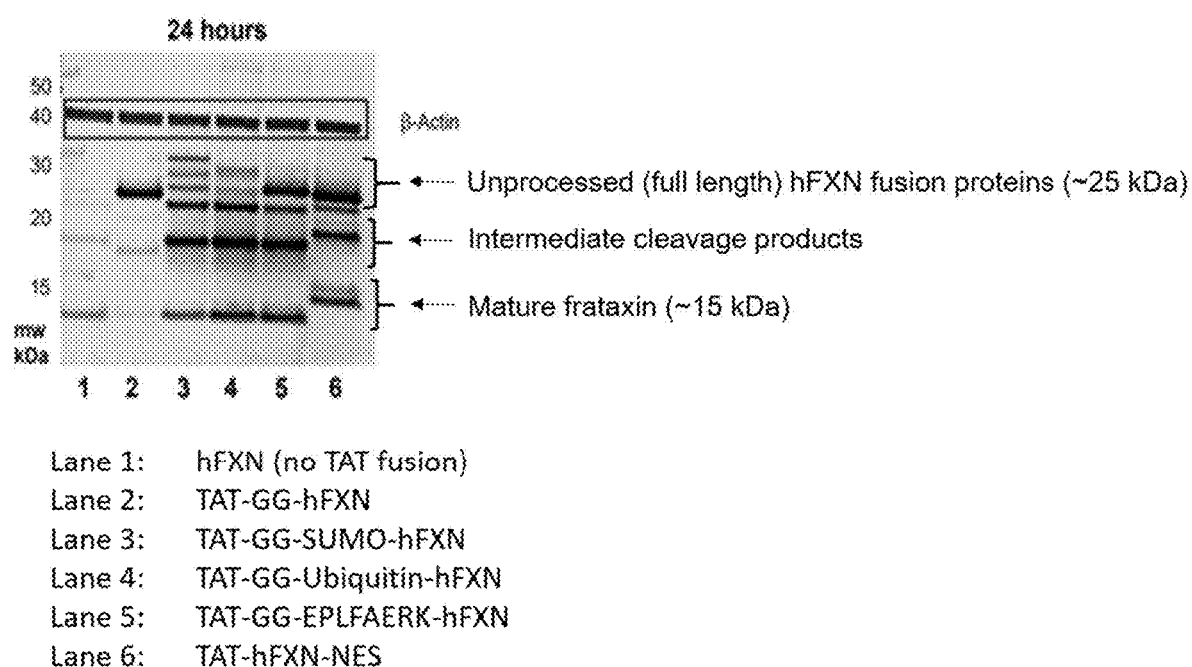
FIG. 11 is a photograph of the Western blot of total protein samples isolated from cells transfected with various hFXN fusion proteins and analyzed using anti-FXN antibody.

FIG. 11 is a photograph of the Western blot of total protein samples isolated from cells transfected with various hFXN fusion proteins and analyzed using anti-FXN antibody. Lane 1 contains a sample of cells transfected with a construct encoding hFXN control without TAT fusion. In this sample, a band of about 15 kDa corresponds to mature, processed hFXN resulting after double cleavage of the MTS sequence by endogenous mitochondrial α- and β-MPP proteases.

Lane 2 corresponds to a sample of cells transfected with a construct encoding TAT-GG-hFXN fusion protein. In this sample, a small amount of hFXN appears as a processed, mature frataxin, however, the majority of hFXN exists as a full length unprocessed fusion protein of about 25 kDa.

Lanes 3, 4 and 5 correspond to samples of cells transfected with constructs encoding, respectively, TAT-SUMO-hFXN, TAT-GG-Ubiquitin-hFXN and TAT-GG-EPL-FAERK-hFXN. Under the same experimental conditions, these samples contain higher amounts of mature hFXN than the samples in lanes 1 and 2. Also present in lanes 3-5 are the intermediate cleavage products corresponding to incomplete hFXN processing and to various SUMO cleavages (lane 3).

Lane 6 contains a sample of cells transfected with constructs encoding TAT-GG-hFXN-NES. This sample also contains higher amounts of mature hFXN than samples in lanes 1 and 2. Also present in lane 6 are the intermediate cleavage products corresponding to incomplete hFXN processing. It is noted that the molecular weight of mature hFXN and intermediate cleavage products is higher than the the molecular weight of mature hFXN and intermediate cleavage products in other samples because NES is not cleaved by processing and remains a part of the fusion protein after MTS cleavage.

The results presented in FIG. 11 demonstrate that the novel hFXN fusion proteins of the present disclosure, i.e., TAT-SUMO-hFXN, TAT-GG-Ubiquitin-hFXN, TAT-GG-EPLFAERK-hFXN, and TAT-GG-hFXN-NES are processed in cells to yield mature hFXN. The results also demonstrate that the processing of the novel hFXN fusion proteins to yield mature hFXN is more efficient than processing of TAT-GG-hFXN fusion protein. The more efficient processing of the novel hFXN fusion proteins as compared to processing of TAT-GG-hFXN may, at least partially, be explained by the fact that lower amounts of the novel hFXN fusion proteins localize to the nucleus, as compared to the TAT-GG-hFXN fusion proteins, as shown in FIGS. 4 and 6.

Example 8. Functional Characterization of hFXN Fusion Proteins

The goal of this experiment was to characterize the function of the novel hFXN fusion proteins. Applicant has previously shown that cells deficient in LRPPRC exhibit high levels of cell media acidification and secretion of SYR61 protein into the media. Applicant has also previously shown that treatment of LRPPRC-deficient cells caused a decrease in both cell media acidification and the amount of secreted SYR61 protein (see, e.g., WO 2021/011929, the entire contents of which are hereby incorporated herein by reference). Thus, cell media acidification and the amount of secreted SYR61 protein may be used as a measure of FXN activity in cells.

The present experiment utilized cell line HEK 293 LRPPRC KD (clone 21C), which was previously described, e.g., in WO 2021/011929. Briefly, this cell line is an LRPPRC knockdown cell line, generated by transferring HEK293 cells with LRPPRC shRNA, resulting in gene silencing of LRPPRC. A control cell line transfected with a scramble sequence (Scr-5) was also used in the experiment. This experiment also utilized the same hFXN fusion proteins used in Example 5 and illustrated in FIG. 8, i.e., TAT-GG-hFXN, TAT-GG-EPLFAERK-hFXN and TAT-GG-Ubiquitin-hFXN.

For the experiment, the LRPPRC KD cells and Scr-5 cells were plated at a seeding density of 50,000 cells per well in a 24 well plate in complete DMEM (DMEM, 10% FBS and 1% antibiotic:antimycotic). On day 1, the cells were treated with vehicle, TAT-GG-hFXN, TAT-GG-EPLFAERK-hFXN, or TAT-GG-Ubiquitin-hFXN for 3 hours at 37° C. Treatment of cells with TAT-GG-hFXN fusion protein was conducted at the fusion protein concentrations of 2.5 µM, 5 µM and 10 µM. Treatment of cells with TAT-GG-EPLFAERK-hFXN and TAT-GG-Ubiquitin-hFXN was conducted at the fusion protein concentrations of 0.25 µM, 0.5 µM and 1 µM. After three hours, complete media was added to each well, and the cells were incubated overnight at 37° C.

The same treatment was repeated on day 2, and the cells were incubated overnight at 37° C. On day 3, the cells were incubated in complete medium for additional 48 hours.

After 48 hours, the media was collected. Analysis of CYR61 levels was performed by CYR61 Elisa using Human Cyr61/CCN1 Quantikine ELISA Kit (R & D Systems catalogue #DCYR10). Lactate levels in the media were determined using lactate glo kit (#J5021 Promega Corporation) according to the manufacturer's protocol.

Figure 12:
FIG. 12, Panel A shows a picture of culture plate containing samples of LRPPRC KD cells and Scr-5 cells treated with hFXN fusion proteins of the disclosure.
Figure 12:
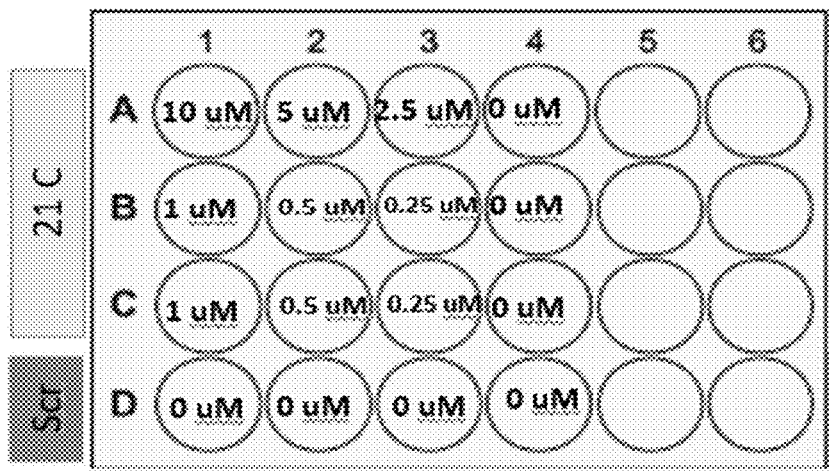
Figure 12:
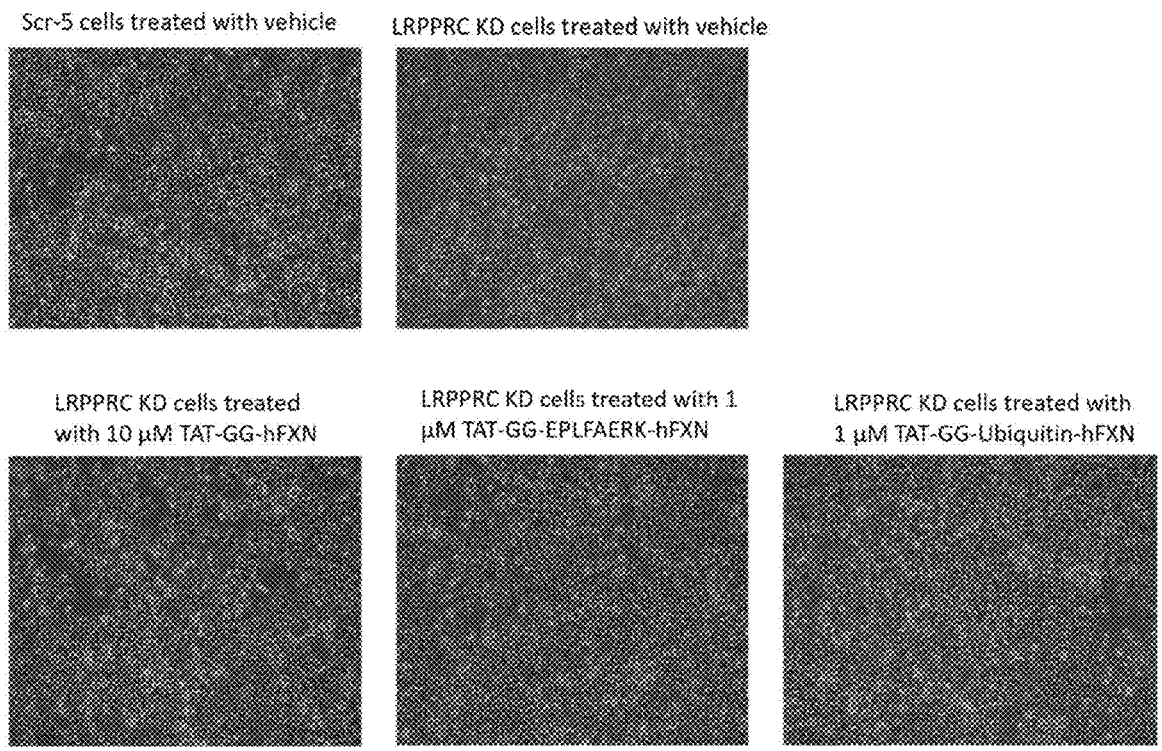
Figure 12:
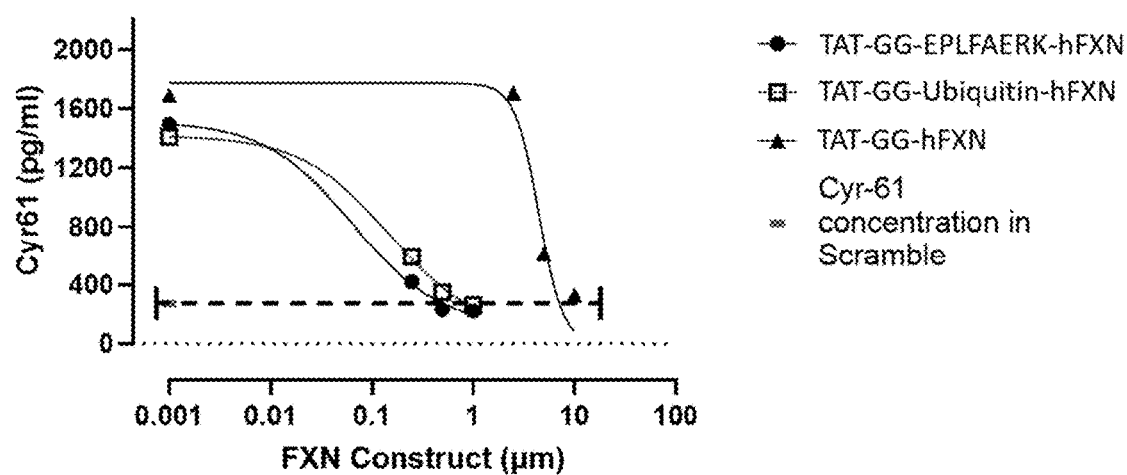
Figure 12:
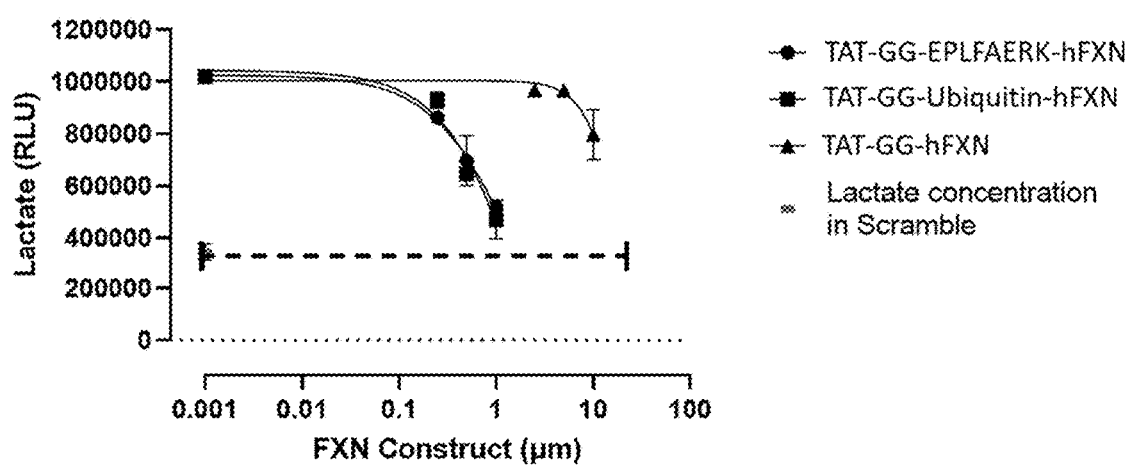

FIG. 12, Panel A shows a picture of a culture plate containing samples of LRPPRC KD cells and Scr-5 cells treated with hFXN fusion proteins of the disclosure. Acidification of the cell culture media is reflected by the changing color of phenol red in the culture media from pink (low acidification) to yellow (high acidification). FIG. 12, Panel A also shows a schematic representation of samples in the cell culture plate shown in the picture.

The results in FIG. 12, Panel A demonstrate that LRPPRC KD cells induce cell media acidification (as demonstrated by the yellow media in the wells of column 4, rows 1-3, of the plate), and that the extent of media acidification decreases in a dose-dependent manner after treatment with the tested hFXN fusion proteins (as demonstrated by: the orange media in the wells in column 3, rows 1-3; the pink media in the wells in column 2, rows 1-3; and the darker pink/red media in the wells in column 1, rows 1-3, of the plate). The results also demonstrate that TAT-GG-hFXN can prevent media acidification at a concentration of 10 µM, while each of TAT-GG-EPLFAERK-hFXN and TAT-GG-Ubiquitin-hFXN can prevent media acification at a significantly lower concentration of 1 µM than TAT-GG-hFXN.

FIG. 12, Panel B is a series of photographs of the LRPPRC KD and Scr-5 control cells treated with the highest tested concentration of each hFXN fusion protein or vehicle. The results in FIG. 12, Panel B demonstrate that acidification of the cell culture media was not due to cell death.

FIG. 12, Panel C is a graph showing the amount of CYR61 in the media of LRPPRC KD cells treated with hFXN fusion proteins. The results in FIG. 12, Panel C demonstrate concentration-dependent inhibition of CYR61 secretion by the LRPPRC KD cells after treatment with hFXN fusion proteins. The results also demonstrate that the inhibitory effect on CYR61 secretion is seen at significantly lower concentrations of TAT-GG-EPLFAERK-hFXN and TAT-GG-Ubiquitin-hFXN as compared to TAT-GG-hFXN. This effect is also reflected in the lower $IC_{50}$ values for CYR61 inhibition of TAT-GG-EPLFAERK-hFXN and TAT-GG-Ubiquitin-hFXN as compared to the $IC_{50}$ value of TAT-GG-hFXN, presented in the table in FIG. 12, Panel C.

FIG. 12, Panel D is a graph showing the amount of lactate in the media of LRPPRC KD cells treated with hFXN fusion proteins. The results in FIG. 12, Panel D demonstrate concentration-dependent inhibition of lactate production by the LRPPRC KD cells after treatment with hFXN fusion proteins. The results also demonstrate that the inhibitory effect on lactate production is seen at significantly lower concentrations of TAT-GG-EPLFAERK-hFXN and TAT-GG-Ubiquitin-hFXN as compared to TAT-GG-hFXN. This effect is also reflected in the lower $IC_{50}$ values for inhibition of lactate production of TAT-GG-EPLFAERK-hFXN and TAT-GG-Ubiquitin-hFXN as compared to the $IC_{50}$ value of TAT-GG-hFXN, presented in the table in FIG. 12, Panel D.

The results presented in FIG. 12, Panels A-D demonstrate that TAT-GG-EPLFAERK-hFXN and TAT-GG-Ubiquitin-hFXN are characterized by higher activity than TAT-GG-hFXN, as measured by the inhibition of lactate production and CYR61 secretion. The results indicate that introducing TES into a fusion protein enhances function of the fusion protein.

Example 9. Design and Synthesis of Novel PARKIN Fusion Constructs

The goal of this experiment was to synthesize novel fusion proteins according to the present disclosure comprising human PARKIN protein (SEQ ID NO: 7).

The design of the PARKIN fusion proteins was similar to the design of the hFXN fusion constructs described in Example 2. Some PARKIN fusion proteins comprised a sequence encoding a cell penetrating peptide (CPP), such as HIV-TAT (YGRKKRRQRRR; SEQ ID NO: 11) peptide, fused to TES, e.g., an amino acid sequence that can be cleaved by an endogenous intracellular protease, and immediately followed by PARKIN as the protein of interest. A di-peptide GG was used as a linker between the CPP and the proteolytic cleavage domain. Cleavage of TAT-GG from the fusion protein in the cytosol will result in a TAT-free PARKIN protein. The proteolytic cleavage domains used in the PARKIN fusion proteins were ubiquitin (SEQ ID NO: 18) and EPLFAERK (SEQ ID NO: 45).

An alternative PARKIN fusion protein was designed to include a nuclear exportation signal (NES), and in that way avoid accumulation of PARKIN in the cellular nucleus. The construct was designed to include a CPP, linked to PARKIN as a protein of interest, linked to a NES.

Figure 13:
FIG. 13 is a schematic representation of the structure of PARKIN fusion proteins of the present disclosure.
Figure 13:
Figure 13:
Figure 13:

A schematic of the PARKIN fusion proteins is provided in FIG. 13, and a summary of the fusion protein constructs is provided in Table 13.

TABLE 13

Novel TAT-PARKIN fusion proteins.

| Fusion Protein | SEQ ID NO. | CPP | Protease cleavable domain or NES | Protease responsible for cleavage | Protein of interest |
|---|---|---|---|---|---|
| татАТ-GG-Ubiquitin-PARKIN | 69 | TAT | Ubiquitin | Deubiquitinase | PARKIN |
| TAT-GG-EPLFAERK-PARKIN | 70 | TAT | EPLFAERK (SEQ ID NO: 20) | Calpain1 | PARKIN |
| TAT-GG-PARKIN-NES1 | 71 | TAT | NES1 | not relevant | PARKIN |
| His6-SUMO-TAT-GG-PARKIN | 82 | TAT | SUMO | SUMO | PARKIN |

The amino acid sequence of His6-SUMO-TAT-GG-PARKIN (SEQ ID NO: 82), which was used as a control, is shown below:

HHHHHHSDSEVNQEAKPEVKPEVKPETHINLKVSDGSSEIFFKIKKTTP

LRRLMEAFAKRQGKEMDSLRFLYDGIRIQADQTPEDLDMEDNDIIEAHR

EQIGGMYGRKKRRQRRRGGMIVFVRFNSSHGFPVEVDSDTSIFQLKEVV

AKRQGVPADQLRVIFAGKELRNDWTVQNCDLDQQSIVHIVQRPWRKGQE

MNATGGDDPRNAAGGCEREPQSLTRVDLSSSVLPGDSVGLAVILHTDSR

KDSPPAGSPAGRSIYNSFYVYCKGPCQRVQPGKLRVQCSTCRQATLTLT

-continued

```
QGPSCWDDVLIPNRMSGECQSPHCPGTSAEFFFKCGAHPTSDKETSVAL

HLIATNSRNITCITCTDVRSPVLVFQCNSRHVICLDCFHLYCVTRLNDR

QFVHDPQLGYSLPCVAGCPNSLIKELHHFRILGEEQYNRYQQYGAEECV

LQMGGVLCPRPGCGAGLLPEPDQRKVTCEGGNGLGCGFAFCRECKEAYH

EGECSAVFEASGTTTQAYRVDERAAEQARWEAASKETIKKTTKPCPRCH

VPVEKNGGCMHMKCPQPQCRLEWCWNCGCEWNRVCMGDHWFDV.
```

It is noted that in the control fusion protein, His6-SUMO-TAT-GG-PARKIN, the His6-SUMO portion is present solely for the ease of purification. Following purification using the His6 tag (SEQ ID NO: 85), the His6 tag (SEQ ID NO: 85) is removed by the protease-mediated cleavage of the SUMO sequence. Thus, the control fusion protein of SEQ ID NO: 82 does not contain a TES sequence.

Example 10. Transduction Ability of PARKIN Fusion Proteins

The goal of this experiment was to determine the ability of PARKIN fusion proteins to transduce cells and to localize to the mitochondria.

The experiment utilized L6 rat myoblast cells because these cells have low endogenous PARKIN levels and therefore do not interfere with the signal produced by the TAT-GG-hFXN fusion proteins. The experiment also utilized the PARKIN fusion proteins described in Example 9.

For the experiment, L6 cells were plated at a seeding density of 8,000 cells per well in a 96 well plate (coming 3904) in complete DMEM medium (DMEM, 10% FBS and 1% antibiotic:antimycotic) and incubated overnight at 37° C. On day 1, the cells were treated with 0.0625 µM, 0.125 µM, 0.25 µM, 0.5 µM and 1 µM of each PARKIN fusion protein for 2 hours at 37° C. After two hours, same amount of complete media was added per well and incubated overnight at 37° C. The same treatment was repeated on day 2.

On day 3, the cells were washed with PBS, trypsinized, resuspended in the complete cell culture medium, transferred to a fibronectin-coated glass-bottom plate allowed to settle overnight at 37° C. On day 4, the cells were washed with PBS and treated with freshly prepared 4% paraformaldehyde solution at room temperature for 10 minutes. After 10 minutes, the cells were washed twice PBS, and then 50 µL of blocking buffer (0.3% Triton-X 100, 5% normal goat serum in PBS) was added per well and incubated at room temperature for 1 hour. After 1 hour, blocking buffer was aspirated and 50 µL of primary antibody diluted in blocking buffer (Anti-Parkin Antibody, 12235-1-AP (1:100) and anti-TOMM20 antibody, EMD Millipore MABT166 (1:500), was added per well and incubated overnight at 4° C.

On day 5, the cells were washed twice with PBS and 50 µL of secondary antibody diluted in blocking buffer (Anti-Mouse IgG AlexaFluor594, ab150116 abcam (1:1000), Anti-rabbit IgG Alexafluor488, ab150077 abcam (1:1000)) was added to each well. The cells were incubated at room temperature for one hour, after which they were gently washed with PBS, mixed with 50 µL of 300 nM Hoescht 33342 stain and allowed to stand at room temperature for 3 minutes. Subsequently, the cells were washed twice with PBS and imaged. The ratio of PARKIN protein colocolizing with mitochondria was evaluated using Harmony software from Operetta (High Content Imager from Perkin Elmer and plotted as a function of the ratio of PARKIN localizing to mitochondria to concentration of proteins (µM). Specifically, the ratio of the amount of AlexaFluor488 staining (corresponding to PARKIN) to the amount of AlexaFluor 594 staining (corresponding to mitochondria) was calculated and plotted on a graph to compare the transduction efficiency of various PARKIN fusion proteins.

Figure 14:
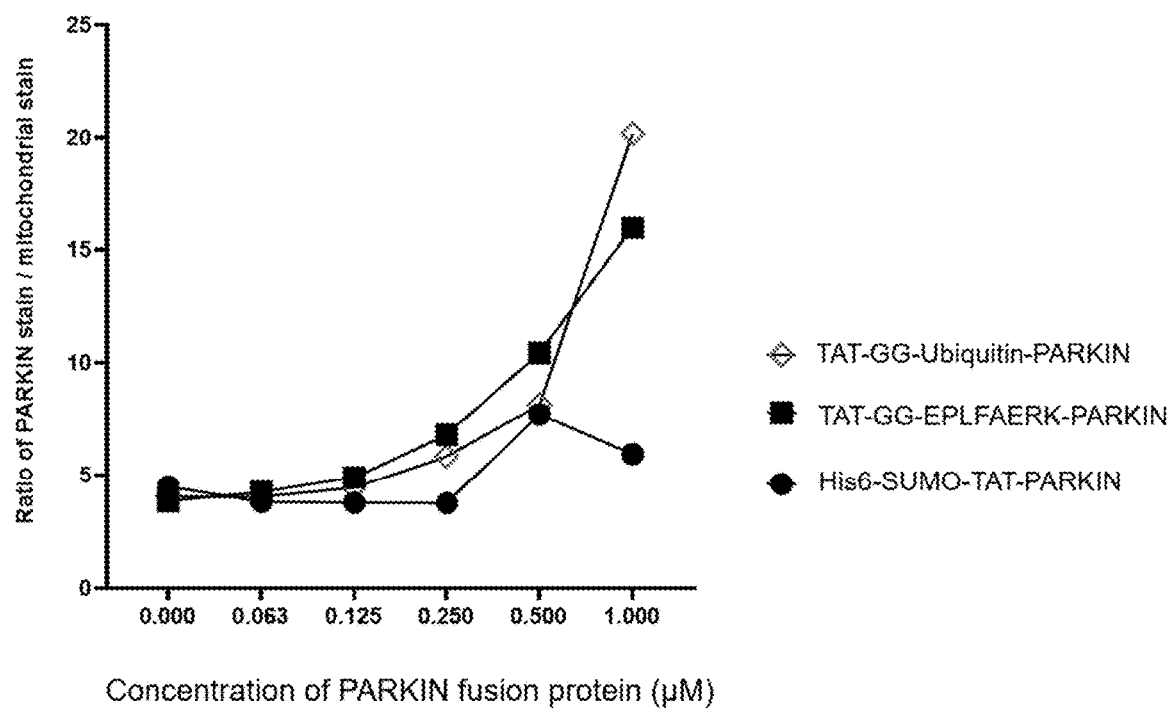
FIG. 14 is a graph showing the ratio of PARKIN stain to the mitochondrial stain as a function of PARKIN fusion protein concentration for cells treated with different concentrations of His6-SUMO-TAT-GG-PARKIN, TAT-GG-EPLFAERK-PARKIN and TAT-GG-Ubiquitin-PARKIN.

The results of the experiment are presented in FIG. 14. Specifically, FIG. 14 is a graph showing the ratio of PARKIN stain to the mitochondrial stain as a function of PARKIN fusion protein concentration for cells treated with different concentrations of His6-SUMO-TAT-GG-PARKIN, TAT-GG-EPLFAERK-PARKIN and TAT-GG-Ubiquitin-PARKIN. The results presented in FIG. 14 demonstrate that transduction of cells with the PARKIN fusion proteins occurs in a dose dependent manner, with higher ratios indicating higher mitochondria localization. The results indicate that PARKIN fusion proteins containing TES, i.e., TAT-GG-EPLFAERK-PARKIN and TAT-GG-Ubiquitin-PARKIN, have more mitochondrial localization at 1 µM concentration than the control PARKIN fusion protein without TES, His6-SUMO-TAT-GG-PARKIN. The results of this experiment indicate that PARKIN fusion proteins containing TES are transduced into cells and correctly localize to mitochondria in higher amounts than the control His6-SUMO-TAT-PARKIN fusion protein.

Example 11. Activity of PARKIN Fusion Proteins

The goal of this experiment was to test the activity of PARKIN in cells treated with the novel PARKIN fusion proteins. Specifically, the goal of the experiment was to determine if, after treatment of cells with the novel PARKIN fusion proteins, PARKIN localizes to mitochondria to induce mitophagy in the presence of mitochondrial uncoupler, carbonyl cyanide m-chlorophenyl hydrazone (CCCP).

For the experiment, L6 rat myoblast cells were treated with 0 µM, 0.5 µM and 1 µM His6-SUMO-TAT-GG-PARKIN, TAT-GG-EPLFAERK-PARKIN, orTAT-GG-Ubiquitin-PARKIN in the presence and absence of 10 µM CCCP. Immunostaining and microscopy were then performed essentially as described in Example 10.

Figure 15:
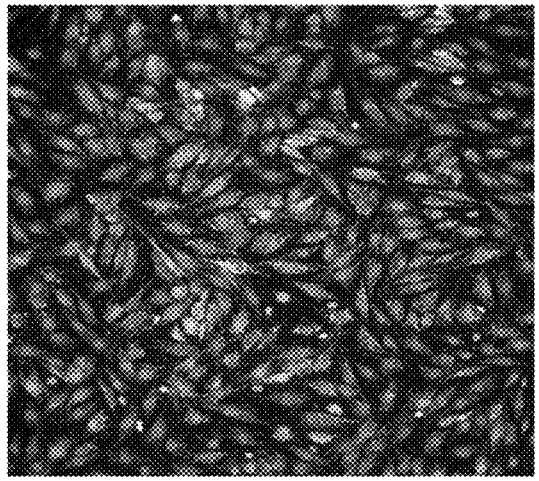
FIG. 15 is a series of phographs of L6 rat myoblast cells treated with 0 μM or 0.5 μM TAT-GG-EPLFAERK-PARKIN in the absence or presence of 10 μM CCCP.
Figure 15:
Figure 15:
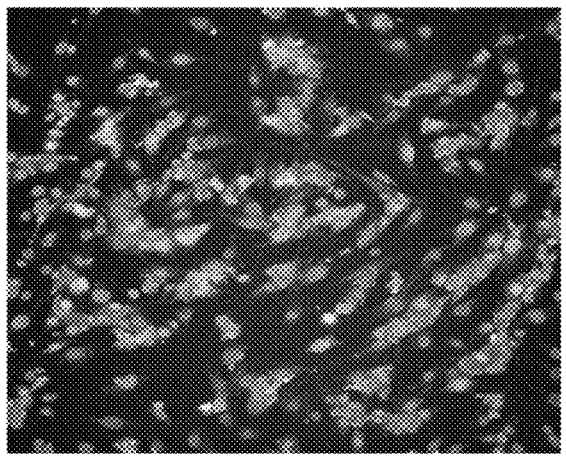
Figure 15:
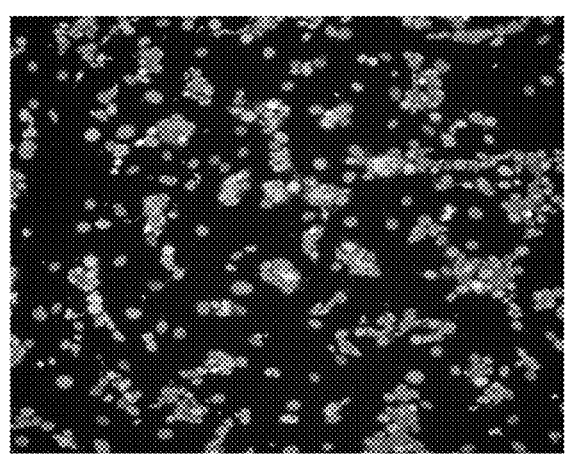

The results of the experiment for TAT-GG-EPLFAERK-PARKIN are shown in FIG. 15. Specifically, FIG. 15 is a series of phographs of L6 rat myoblast cells treated with 0 µM or 0.5 µM TAT-GG-EPLFAERK-PARKIN in the absence or presence of 10 µM CCCP. The results presented in FIG. 15 demonstrate that control L6 rat myoblast cells do not show any morphological differences in the absence or presence of CCCP. Also, FIG. 15 shows that, in the absence of treatment with PARKIN fusion proteins, endogenous PARKIN remains undetectable in L6 cells. The results presented in FIG. 15 also show that in L6 rat myoblast cells treated with TAT-GG-EPLFAERK-PARKIN, localization of PARKIN to mitochondria is observed in the presence of CCCP. This observation is consistent with the known role of endogenous PARKIN in mitophagy which involves PARKIN mitochondrial relocalization to the mitochondria upon mitochondrial membrane depolarization.

The invention claimed is:

1. A fusion protein, comprising:
a protein of interest to be delivered to a cell;
a cell penetrating peptide (CPP); and
a target enhancing sequence (TES); wherein:
the protein of interest comprises an amino acid sequence having at least 85% sequence identity to SEQ ID NO: 1;
the CPP comprises an amino acid sequence having at least 85% sequence identity to SEQ ID NO: 11; and
the TES is a protease-sensitive peptide selected from the group consisting of: Ubiquitin, a caspase cleavage domain, a calpain cleavage domain, a TEV protease cleavage sequence, a Factor Xa protease cleavage sequence, a Thrombin cleavage sequence, and a SUMO having an amino acid sequence having at least 85% sequence identity to SEQ ID NOs: 32, 33 or 35; and
wherein the CPP is located at the N-terminus of the fusion protein and wherein the TES is fused at the C-terminus of the CPP, or
wherein the CPP is located at the C-terminus of the fusion protein and wherein the TES is fused at the N-terminus of the CPP.

2. The fusion protein of claim 1, wherein the protein of interest comprises the amino acid sequence of SEQ ID NO: 1 (Frataxin).

3. The fusion protein of claim 1, wherein the CPP comprises the amino acid sequence of SEQ ID NO: 11 (HIV-TAT).

4. The fusion protein of claim 1, wherein the TES comprises the amino acid sequence selected from the group consisting of SEQ ID NOs: 18-21, 25, 28, 30, 32 (SUMO1), 33 (SUMO2) and 35 (SUMO4).

5. A conjugate for intracellular delivery of proteins to non-nuclear organelles comprising the fusion protein of claim 1 and a moiety linked to said fusion protein, wherein said moiety is selected from a group consisting of a radioactive label, a fluorescent label, a small molecule, and a polymeric molecule.

6. A cell comprising the fusion protein of claim 1, 2, or 3.

7. A pharmaceutical composition comprising the fusion protein of claim 1, 2, or 3.

8. A method of delivering a protein of interest to a cell, said method comprising contacting said cell with the fusion protein of claim 1, 2, or 3.

9. A method of intracellular delivery of a protein of interest to a non-nuclear organelle in a cell, said method comprising contacting said cell with the fusion protein of claim 1, 2, or 3.

10. The method of claim 9, wherein said non-nuclear organelle is mitochondria.

11. A method for treating a non-nuclear organelle associated disorder, said method comprising administering to a subject in need thereof the fusion protein of claim 1, 2, or 3.

12. The method of claim 11, wherein the non-nuclear organelle associated disorder is Friedreich's Ataxia (FRDA).

13. The method of claim 11, wherein said subject is a human.

* * * * *